(12) United States Patent
Checcone et al.

(10) Patent No.: US 11,696,918 B2
(45) Date of Patent: Jul. 11, 2023

(54) VIRAL PROPHYLAXIS TREATMENT METHODS AND PRE-EXPOSURE PROPHYLAXIS KITS

(71) Applicant: ELIAN LLC, Monrovia, CA (US)

(72) Inventors: Emidio A. Checcone, Arcadia, CA (US); Christina Ramirez, Los Angeles, CA (US)

(73) Assignee: ELIAN LLC, Monrovia, CA (US)

( * ) Notice: Subject to any disclaimer, the term of this patent is extended or adjusted under 35 U.S.C. 154(b) by 426 days.

(21) Appl. No.: 16/800,813

(22) Filed: Feb. 25, 2020

(65) Prior Publication Data
US 2020/0397791 A1 Dec. 24, 2020

Related U.S. Application Data

(60) Provisional application No. 62/810,074, filed on Feb. 25, 2019.

(51) Int. Cl.
| | | |
|---|---|---|
| *A61K 31/52* | (2006.01) | |
| *A61K 31/522* | (2006.01) | |
| *A61P 31/22* | (2006.01) | |
| *A61K 9/00* | (2006.01) | |
| *A61K 9/70* | (2006.01) | |
| *A61K 45/06* | (2006.01) | |

(52) U.S. Cl.
CPC .......... *A61K 31/522* (2013.01); *A61K 9/0036* (2013.01); *A61K 9/7023* (2013.01); *A61K 31/52* (2013.01); *A61K 45/06* (2013.01); *A61P 31/22* (2018.01)

(58) Field of Classification Search
CPC .................................................... A61K 31/52
USPC ..................................... 514/262, 264, 262.1
See application file for complete search history.

(56) References Cited

U.S. PATENT DOCUMENTS

| | | |
|---|---|---|
| 6,107,303 A | 8/2000 | Demarco |
| 7,253,175 B2 | 8/2007 | Liberman et al. |

OTHER PUBLICATIONS

R. M. Mays, et al., Current Developments in Viral Skin Diseases, Current Dermatology Reports. Current Medicine Group LLC, US (Jan. 1, 2021) vol. 1, No. 1, pp. 1-3.
P. Wutzler, et al., Antiviral Efficacies Of Famciclovir, Valaciclovir, And Brivudin in Disseminated Herpes Simplex Virus Type 1 Infection in Mice, Antiviral Research, Elsevier BV, NL (Jan. 1, 1996) vol. 30, No. 1, p. A48.
IPRP dated Aug. 25, 2001 in International Application No. PCT/US2020/019700.

*Primary Examiner* — Raymond J Henley, III
(74) *Attorney, Agent, or Firm* — Duane Morris LLP; Thomas J. Kowalski; Deborah L. Lu

(57) ABSTRACT

The present disclosure provides compositions and methods for the prevention of HSV infection in an HSV seronegative individual and for the treatment and prevention of recurrence in an HSV seropositive individual.

46 Claims, 23 Drawing Sheets

VIRAL PROPHYLAXIS TREATMENT METHODS AND PRE-EXPOSURE PROPHYLAXIS KITS

CROSS-REFERENCE TO RELATED APPLICATIONS

This application claims priority to U.S. provisional patent application Ser. No. 62/810,074, filed on Feb. 25, 2019.

Reference is made to U.S. Provisional Application No. 62/021,589 filed Jul. 7, 2014, U.S. application Ser. No. 14/793,550, filed Jul. 7, 2015, issued as U.S. Pat. No. 10,052,329, and U.S. application Ser. No. 16/044,276, filed Jul. 24, 2018, pending, which are incorporated by reference herein in their entireties.

All documents cited herein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates generally to a combination of compounds with antiviral activity and, more specifically, with anti-herpes properties. This invention provides a composition of matter and a method of use for preventing and treating human herpes virus infections, which, in turn, can cause other disease states.

BACKGROUND OF THE INVENTION

The hallmark of alpha, beta and gamma human herpes viruses is that they all establish latent infections. These viral infections have widespread, worldwide prevalence. Consequences of these infections range from asymptomatic disease (i.e., sero-positivity) to repeated and/or severe episodes of symptoms caused by the active form of the disease. Some of these herpes virus infections have devastating consequences, such life-threatening encephalitis in neonates and immuno-compromised patients. Classic nucleoside analogs are useful for the treatment of herpes virus related diseases such as HSV-1 and HSV-2, as well as varicella zoster virus (i.e., VZV), and, to a lesser extent, Epstein Barr virus (i.e., EBV) and cytomegalovirus (i.e., CMV).

As with all herpes viruses, once a patient is infected, the virus establishes a latent infection that is not cleared by the immune system even with the help of antiviral drugs, such as valacyclovir, famciclovir, or the like. These antiviral drug compounds, prescribed and administered as a single-drug treatment (i.e., monotherapy) have been shown to reduce the level of viremia for herpes simplex virus infections, but even in high doses and over long-term treatment durations, these drugs do not completely prevent recurrent outbreaks of symptoms from herpes viral infection, which are common. Viral shedding is also common, and it is often the case that this viral shedding can be asymptomatically facilitating the transmission of herpes virus and spread of the disease to more individuals. Monotherapy, even in administered in high doses and over extended periods of time, is not able to achieve long-term viral suppression of herpes infections necessary to stop outbreaks or prevent transmission to another individual. Indeed, long-term suppressive treatment with valacyclovir has been shown to reduce transmission risk only by 46% This therapeutic outcome contrasts highly to anti-HIV therapies, which can achieve sustained viral suppression and can reduce transmission risk by nearly 100%. Currently, monotherapy is the standard of care for preventing herpes outbreaks and viral transmission. Given the highly imperfect efficacy of monotherapy, there exists a clear need for greater protection from outbreaks and viral transmission, which can be achieved with a combination therapy for herpes infections. The use of antiviral drugs used in novel combinations can yield an increase in drug efficacy, or possibly, an equivalent antiviral effect but with reduced dosage, thereby potentially reducing or limiting risks related to drug toxicity.

Recent research has implicated herpes viruses, such as herpes simplex virus types 1 and 2 (i.e., HSV-1 and HSV-2), Epstein Barr virus (i.e., EBV), human cytomegalovirus (i.e., HCMV), varicella zoster virus (VZV, i.e. chicken pox, shingles, human herpes virus 3)), Kaposi's Sarcoma herpes associated Virus (i.e., KSHV HHV-8), Human Herpes Virus-6 and -7 (i.e., HHV-6, HHV-7) as having a contributory role in causing a wide variety of diseases, such as neonatal herpes, herpes encephalitis, Alzheimer's disease, senile dementia, multiple sclerosis, systemic lupus erythematosus (i.e., SLE), rheumatoid arthritis, juvenile idiopathic arthritis (i.e., JIA), inflammatory bowel disease (i.e., IBD), celiac disease, type 1 diabetes, mononucleosis, among others.

SUMMARY OF THE INVENTION

Herpes simplex virus (HSV) is associated in many infected individuals with recurrences that manifest themselves as cold sores and/or genital herpes, both of which are often painful and embarrassing. HSV is also of significant public health consequence in that infection with HSV increases the risk of a person acquiring human immunodeficiency virus (HIV) by 2-3 fold, with an 8-fold increased risk if the person is exposed to HIV soon after HSV is acquired. Therefore, in order to address the HIV epidemic, it is also necessary to address the HSV epidemic.

During primary infection, HSV infects epithelial cells at the skin and mucosal surfaces. The virus then travels along nerve axons to the dorsal root ganglia. It is there that latency is established, as the virus can lie dormant and hidden from the immune system in this location. Thus, these neuronal cells act as the reservoir for the latent virus. When the virus is reactivated, the virus travels from the dorsal root ganglia back to the skin, referred to as viral shedding, where the virus is detectable from the epithelial surfaces. Viral reactivation is sometimes asymptomatic or may create a lesion or ulcer. In either case, the virus may be transmitted to a new host. Most HSV-2 transmissions occur during asymptomatic shedding.

A traditional approach to reduce HSV transmission through sexual contact involves the use of physical barriers between HSV seropositive and HSV seronegative individuals, for example, condoms. While condom usage is effective in the prevention of some sexually transmitted infections, in the case of HSV, the site of infection may lie outside of the region where the condom provides protection. If there exists viral shedding in sites outside of the condom area, transmission can still occur even with proper condom usage as skin-to-skin contact during viral shedding is sufficient for HSV transmission.

Clinical treatment of HSV has shifted from focusing on acute treatment of symptomatic outbreaks (e.g., treatment of lesions) to reducing the frequency of symptomatic outbreaks, thus reducing the viremia and amount of viral shedding in the seropositive individual. This has led to the development of suppressive therapy, in which the seropositive individual attempts to maintain a low-level concentration of an HSV antiviral drug in the bloodstream so that the number of outbreaks is potentially reduced, and to reduce viral shedding, potentially lowering the risk of transmission. However, suppressive treatment with antiviral drugs does not completely eliminate all viral shedding, providing a possible transmission pathway for infection of seronegative individuals.

Even with suppressive treatments proliferating, HSV infections have exploded and are elevating the risk of HIV infection, making the spread of HSV a serious public health risk and pandemic. There are a number of deficiencies in current suppressive therapy that hinder the effectiveness of decreasing HSV transmission from the HSV seropositive to the HSV seronegative individual. Treatment focused solely on seropositive individuals can create a single point of failure with respect to reducing the likelihood of transmission. For example, if the seropositive individual is non-compliant with the drug regimen, if the viral strain is resistant to the antiviral agent, and/or if the dosage is inadequate, then a sufficient amount of virus to produce a sustainable infection may be transferred to the seronegative person. Under this single-subject treatment approach, controlling the spread of HSV is solely dependent on the effectiveness of a single layer, the treatment of a seropositive subject. This has failed to adequately reduce the spread of HSV. Traditional suppressive therapies also generally involve administering a single antiviral drug. This single-drug approach exacerbates the single point of failure problem, as cumulative effects of multiple drugs are not realized, and the probability of exposing the virus to the optimal drug option can be reduced. In addition, as a result of non-compliance, a viral strain may evolve and develop resistance to the single drug in use, weakening or even possibly neutralizing the single layer protection. A further important issue is that many people are unaware that they are infected with HSV or are in denial of their HSV seropositive status, and therefore they may not be aware of or provided with suppressive therapy. In a National Health and Nutrition Examination Survey performed in 1997 and published in the New England Journal of Medicine, 91% of people seropositive for HSV-2 were unaware that they were infected. Furthermore, suppressive therapy does not offer an HSV seronegative individual who may be at risk of exposure to HSV a method of protection outside of avoiding direct physical contact with an HSV seropositive individual. For many individuals, especially those in situations where consent or knowledge of the other persons true sero-status is not established prior to physical activity, such protection is not available. The present disclosure addresses the need for providing compositions and methods for the prevention of HSV infection in a seronegative individual by treating the seronegative individual with one or more antiviral agents. Further provided, are methods and compositions for treating both HSV seropositive and HSV seronegative individuals with one or more antivirals to further reduce the risk of HSV transmission and infection.

In one aspect, the invention provides methods and compositions of matter for preventing and treating human herpes virus infections. Herpes virus can, in turn, cause other disease states. Hence, the invention serves to prevent or mitigate, indirectly, the symptoms related to these other disease states.

In certain embodiments, the invention provides methods and compositions for preventing and treating diseases that have an underlying condition that is caused by human herpes virus infections, using a combination antiviral therapy, whereby the antiviral is valacyclovir, famciclovir, or a similar antiviral drug, and/or the combination thereof. In an embodiment, a first antiviral drug is administered in combination with a second antiviral drug, or multiple additional antivirals, in specific amounts to a person who is seronegative for one of the herpes viruses. In an embodiment, a first antiviral drug is administered in combination with a second antiviral drug, or multiple additional antivirals, in specific amounts to a person who is sero-positive for herpes, but at risk of acquiring the virus.

In certain embodiments the use of combinations of antiviral agents provides for reduced dosing with equivalent efficacy, potentially reducing toxicity, or can increase the overall efficacy of the therapy. Some compounds are individually well tolerated but can exhibit toxic effects in combination (known examples of such non-obvious effects in combination would include: DDI and DDC, AZT+recombinant alpha-interferon, et. al.). As set forth herein, it has been surprisingly found that certain combinations of antiviral agents exhibit superior antiviral activity. The invention satisfies a need for a novel combination of active antiviral drugs for herpes infections which can provide higher levels of efficacy (i.e., reduced viremia, reduced incidence of symptoms, lower transmission rates, etc.) while preserving or enhancing the safety profile related to the standard-of-care therapy.

In one aspect, provided herein is a method of preventing HSV infection in an HSV seronegative subject, the method comprising administering to the subject a therapeutically effective amount of a first antiviral agent prior to physical contact with a partner who is seropositive for HSV. In some embodiments, the subject is or will be in an ongoing mutually-monogamous sexual relationship with the HSV seropositive partner. In some embodiments, the subject is not or will not be in a mutually-monogamous sexual relationship with the HSV seropositive partner. In some embodiments, the method further comprises administering to the HSV seropositive partner a therapeutically effective amount of a second antiviral agent. In some embodiments, the method further comprises determining if the subject is at risk for exposure to HSV prior to administering the first antiviral agent. In some embodiments, the method further comprises determining the therapeutically effective amount of the first antiviral agent. In some embodiments, administering comprises delivering the first antiviral agent to the subject using a long-acting drug delivery device. In some embodiments, the long-acting drug delivery device is an intravaginal ring.

In some embodiments, the first antiviral agent comprises valacyclovir, acyclovir, famciclovir, penciclovir, pritelivir, tenofovir, ganciclovir, glycyrrhizic acid, *Sambucus nigra*, valganciclovir, amenamevir, N-methancocarbathymidine (N-MCT), or a salt, solvate or combination thereof. In some embodiments, the therapeutically effective amount of the first antiviral agent is from about 5 mg to about 10,000 mg. In combinations, the therapeutically effective amount of the second antiviral agent is from about 5 mg to about 10,000 mg.

In some embodiments, the method further comprises administering to the subject a therapeutically effective amount of an additional antiviral agent. In some embodiments, the additional antiviral agent is an HIV antiviral agent. In some embodiments, the HIV antiviral agent comprises tenofovir, emtricitabine, lamivudine, efavirenz, raltegravir, dolutegravir, maravoric, rilpirivine, or a salt, solvate or combination thereof.

In some embodiments, the method further comprises administering to the subject an effective amount of a contraceptive. In some embodiments, the contraceptive comprises levonorgestrel, estradiol, dosogestrel, ethinyl estradiol, norethindrone acetate, norgestimate, or a salt, solvate or combination thereof.

In another aspect, provided herein is a method of preventing HSV infection in an HSV seronegative subject, the method comprising administering to the subject a therapeutically effective amount of a first antiviral agent after physical contact with a partner who is seropositive for HSV. In some embodiments, the method further comprises administering to the subject a therapeutically effective amount of an additional antiviral agent prior to physical contact with the HSV seropositive partner. In some embodiments, the method further comprises administering to the HSV seropositive partner a therapeutically effective amount of a second antiviral agent. In some embodiments, the method further comprises determining the therapeutically effective amount of the first antiviral agent.

In some embodiments, administering comprises delivering the first antiviral agent to the subject using a long-acting drug delivery device. In some embodiments, the long-acting drug delivery device is an intravaginal ring.

In some embodiments, the first antiviral agent comprises valacyclovir, acyclovir, famciclovir, penciclovir, pritelivir, tenofovir, ganciclovir, glycyrrhizic acid, *Sambucus nigra*, valganciclovir, amenamevir, N-methancocarbathymidine (N-MCT), or a salt, solvate or combination thereof. In some embodiments, the therapeutically effective amount of the first antiviral agent is from about 500 mg to about 2000 mg.

In some embodiments, the method further comprises administering to the subject a therapeutically effective amount of an HIV antiviral agent. In some embodiments, the HIV antiviral agent comprises tenofovir, emtricitabine, lamivudine, efavirenz, raltegravir, dolutegravir, maravoric, rilpirivine, or a salt, solvate or combination thereof.

In some embodiments, the method further comprises administering to the subject an effective amount of a contraceptive. In some embodiments, the contraceptive comprises levonorgestrel, estradiol, dosogestrel, ethinyl estradiol, norethindrone acetate, norgestimate, or a salt, solvate or combination thereof. In some embodiments, the contraceptive is an emergency contraceptive. In some embodiments, the emergency contraceptive comprises levonorgestrel.

In another aspect, provided herein is an HSV treatment kit comprising a) a therapeutically effective amount of a first antiviral agent; b) a delivery device for delivering the first antiviral agent to an HSV seronegative subject; and c) instructions comprising information on how to administer the first antiviral agent using the delivery device to prevent HSV infection in the HSV seronegative subject.

In some embodiments, the therapeutically effective amount of the first antiviral agent is an amount useful for the prevention of HSV infection in the HSV seronegative subject when administered to the HSV seronegative subject prior to exposure to HSV. In some embodiments, the therapeutically effective amount of the first antiviral agent is an amount useful for suppression of HSV in a seropositive subject; provided that the delivery device further provides a method for delivering the first antiviral agent to the HSV seropositive subject; and provided that the instructions further comprise information on how to administer the first antiviral agent using the delivery device to suppress HSV reactivation in the HSV seropositive subject.

In some embodiments, the therapeutically effective amount of the first antiviral agent is an amount useful for the prevention of HSV infection in the HSV seronegative subject when administered after the HSV seronegative subject is exposed to HSV. In some embodiments, the therapeutically effective amount of the first antiviral agent is an amount useful for treatment of an outbreak of HSV in a seropositive subject; provided that the delivery device further provides a method for delivering the first antiviral agent to the HSV seropositive subject; and provided that the instructions further comprise information on how to administer the first antiviral agent using the delivery device to treat an HSV outbreak in the HSV seropositive subject.

In some embodiments, the delivery device is a long-acting drug delivery device. In some embodiments, the long-acting delivery device is an intravaginal ring.

In some embodiments, the first antiviral agent comprises valacyclovir, acyclovir, famciclovir, penciclovir, pritelivir, tenofovir, ganciclovir, glycyrrhizic acid, *Sambucus nigra*, valganciclovir, amenamevir, N-methancocarbathymidine (N-MCT), or a salt, solvate or combination thereof.

In some embodiments, the kit further comprises one or more additional antiviral agents. In some embodiments, the one or more additional antiviral agents comprises an HSV antiviral agent, an HIV antiviral agent, or both HSV and HIV antiviral agents. In some embodiments, the HIV antiviral agent comprises tenofovir, emtricitabine, lamivudine, efavirenz, raltegravir, dolutegravir, maravoric, rilpirivine, or a salt, solvate or combination thereof.

In some embodiments, the kit further comprises an effective dose of a contraceptive. In some embodiments, the contraceptive comprises levonorgestrel, estradiol, dosogestrel, ethinyl estradiol, norethindrone acetate, norgestimate, or a salt, solvate or combination thereof.

In another aspect, provided herein is a method of preventing HSV infection in an HSV seronegative subject, the method comprising administering to the subject a composition comprising a low dose of a first antiviral agent prior to physical contact with a partner who is seropositive for HSV. In some embodiments, the method comprises administering a low dose of a second antiviral agent prior to physical contact with a partner who is seropositive for HSV. In some embodiments, the physical contact occurs during one occasion. In some embodiments, the physical contact occurs during two or more separate occasions. In some embodiments, the physical contact occurs with the HSV seropositive partner and one or more additional partners. In some embodiments, the physical contact is sexual contact. In some embodiments, the subject and the HSV seropositive partner use a physical barrier during sexual contact, as non-limiting examples, a male or female condom. In some embodiments, the subject is or will be in an ongoing mutually-monogamous sexual relationship with the HSV seropositive partner. In some embodiments, the subject is not or will not be in a mutually-monogamous sexual relationship with the HSV seropositive partner. In some embodiments, the HSV seropositive partner is aware of their HSV sero-status. In some embodiments, the HSV seropositive partner is unaware of their HSV sero-status.

In some embodiments, the HSV seropositive partner is undergoing HSV suppression therapy comprising the administration of a second low dose of a second antiviral agent to the HSV seropositive partner. In some embodiments, the method further comprises administering to the HSV seropositive partner a second low dose of a second antiviral agent. In some embodiments, the second antiviral agent comprises a same active agent as the first antiviral agent. In some embodiments, the second antiviral agent comprises a different active agent than the first antiviral agent.

In some embodiments, the subject is exposed to HSV from the HSV seropositive partner during physical contact. In some embodiments, the administered composition suppresses HSV replication in the subject. In some embodiments, the administered composition suppresses HSV activation in the subject. In some embodiments, the administered composition reduces the risk of HSV infection in the subject. In some embodiments, the risk of HSV infection in the subject is reduced by at least about 50%, 60%, 70%, 80%, 90% or 95%.

In some embodiments, the method further comprises determining if the subject is at risk for exposure to HSV prior to administering the composition. In some embodiments, the subject has been determined to be at risk for exposure to HSV.

In some embodiments, the method further comprises determining the dose of the first antiviral agent or the second antiviral agent. In some embodiments, the method further comprises determining a delivery mechanism for administering the composition to the subject. In some embodiments, the delivery mechanism comprises a long-acting drug delivery device. In some embodiments, the long-acting drug delivery device comprises an injection device, intravaginal ring, transdermal patch, or a combination thereof.

In some embodiments, the dose of the first antiviral agent is from about 5 mg to about 1 g. As non-limiting examples, the composition comprises about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, 4000 mg, 5000 mg, 6000 mg, 8000 mg, or 10,000 mg of the first antiviral agent.

In some embodiments, the method comprises determining a dose that provides an effective amount of an antiviral agent according to body weight. As used herein, body weight and body mass are used interchangeably and refer to the mass of a subject rather than the force exerted in a gravitational field. In some embodiments, the method comprises determining a dose that provides an effective amount of a second antiviral agent according to body mass. In some embodiments, the method comprises determining doses of first and second antiviral agents administered in combination according to body mass. In some embodiments, the doses take into account the affinity of an antiviral agent for its target. In some embodiments, such doses take into account the intracellular half-life of an antiviral agent. In some embodiments, the doses take into account the plasma half-life of the antiviral agent. As non-limiting examples, the composition comprises about 0.5 mg/kg, 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 350 mg/kg, 400 mg/kg, 500 mg/kg, 600 mg/kg, 650 mg/kg, 700 mg/kg, 750 mg/kg, 800 mg/kg, 850 mg/kg, 900 mg/kg, 950 mg, 1000 mg, 2000 mg, 3000 mg, 4000 mg, 5000 mg, 6000 mg, 8000 mg, or 10000 mg, or from about 0.5 mg/kg to about 100 mg/kg, or about 0.5 mg/kg to about 10 mg/kg, or from about 5 mg/kg to about 50 mg/kg, or from about 25 mg/kg to about 250 mg/kg, or from about 100 mg/kg to about 250 mg/kg, or from about 100 mg/kg to about 500 mg/kg, of from about 100 mg/kg to about 1000 mg/kg, or from about 125 mg/kg to about 500 mg/kg, or from greater than 100 mg/kg to about 250 mg/kg, or from greater than 100 mg/kg to about 500 mg/kg, of from greater than 100 mg/kg to about 1000 mg/kg body weight of an antiviral agent.

It has been surprisingly found that certain antiviral agents are more effective for treatment of HSV infection or for prophylaxis of HSV in a subject when administered in combination. Non-limiting uses include: pre-exposure prophylaxis (e.g. preventing infection in a seronegative subject); treatment of initial infection (e.g., before, or as a seronegative person is becoming seropositive); prophylaxis (preventing a recurrent illness) in a seropositive individual; and treatment of a recurrent infection in a seropositive individual. Further, the antiviral agents are useful for treatment or prophylactic treatment of a disease or condition associated with HSV infection.

In certain embodiments, the antiviral agents target the same polymerase. In one exemplary embodiment, a first antiviral agent is valacyclovir and the second antiviral agent is famciclovir. In embodiments involving combinations of a first and second antiviral agent, the doses of the agents can be the same or different. As non-limiting examples, the composition comprises about 0.5 mg/kg, 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 350 mg/kg, 400 mg/kg, 500 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or 2000 mg/kg, or from about 0.5 mg/kg to about 1000 mg/kg, or from about 0.5 mg/kg to about 100 mg/kg, or about 0.5 mg/kg to about 10 mg/kg, or from about 5 mg/kg to about 50 mg/kg, or from about 25 mg/kg to about 100 mg/kg, or from about 25 mg/kg to about 100 mg/kg, or from about 25 mg/kg to about 250 mg/kg, or from about 50 mg/kg to about 250 mg/kg, or from about 100 mg/kg to about 250 mg/kg, or from about 100 mg/kg to about 500 mg/kg, of from about 100 mg/kg to about 1000 mg/kg, or from about 125 mg/kg to about 500 mg/kg, or from greater than 100 mg/kg to about 250 mg/kg, or from greater than 100 mg/kg to about 500 mg/kg, of from greater than 100 mg/kg to about 1000 mg/kg body weight of a first antiviral agent and about 0.5 mg/kg, 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 350 mg/kg, 400 mg/kg, 500 mg/kg, 600 mg/kg, 650 mg/kg, 700 mg/kg, 750 mg/kg, 800 mg/kg, 850 mg/kg, 900 mg/kg, 950 mg, 1000 mg, or 2000 mg, or from about 0.5 mg/kg to about 1000 mg/kg, or from about 0.5 mg/kg to about 100 mg/kg, or about 0.5 mg/kg to about 10 mg/kg, or from about 5 mg/kg to about 50 mg/kg, or from about 25 mg/kg to about 100 mg/kg, or from about 25 mg/kg to about 100 mg/kg, or from about 25 mg/kg to about 250 mg/kg, or from about 50 mg/kg to about 250 mg/kg, or from about 100 mg/kg to about 250 mg/kg, or from about 100 mg/kg to about 500 mg/kg, of from about 100 mg/kg to about 1000 mg/kg, or from about 125 mg/kg to about 500 mg/kg, or from greater than 100 mg/kg to about 250 mg/kg, or from greater than 100 mg/kg to about 500 mg/kg, of from greater than 100 mg/kg to about 1000 mg/kg body weight of a second antiviral agent.

In certain embodiments, the antiviral agents are administered in a dose ratio in mg/kg of about 5:1, about 4:1, about 3:1, about 2:1, about 1:1, about 1:2, about 1:3, about 1:4, or about 1:5.

In certain embodiments, a composition or kit or device is provided whereby valcyclovir and famciclovir are administered together. In certain embodiments, valcyclovir and famciclovir are administered to the same subject in need thereof, by the same route or different routes, at the same time or at different times. In certain embodiments, the doses are relatively low doses, such as when the amount of valcocylovir is about 1 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 1.5 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 2 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 2 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 2.5 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 3 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 4 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 5 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 6 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 7 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 8 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 9 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 10 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 11 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 12.5 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 15 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 17.5 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 20 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 25 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 30 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 40 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 50 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 60 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 70 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 80 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 90 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg. In an embodiment, when the amount of valcocylovir is about 100 mg/kg, the amount of famciclovir can be about 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12.5 mg/kg, 15 mg/kg, 17.5 mg/kg, 20 mg/kg, 25 mg/kg, 30 mg/kg, 40 mg/kg, 50 mg/kg, 60 mg/kg, 70 mg/kg, 80 mg/kg, 90 mg/kg, or 100 mg/kg.

In certain embodiments, it will be desirable for the dose total to be less than 1000 mg or 2000 mg. For example, in embodiments wherein the dose ratio of valacyclovir:famciclovir is 2:1, non-limiting dosages include about 500 mg:250 mg, about 600 mg:300 mg, about 650 mg:325 mg, about 700 mg:350 mg, about 800 mg:400 mg, about 900 mg:450 mg, or about 1000 mg:500 mg.

An absolute dose or dose by body weight tested in an animal model can be a human equivalent dose (HED) See, e.g., NIH guidelines and Nair, A. B. et al., A simple practice guide for dose conversion between animals and human, J Basic Clin Pharm. March 2016-May 2016; 7(2): 27-31. Examples set forth herein using mice or guinea pigs employ human equivalent doses.

In certain embodiments, one or more antiviral agents used in a combination comprise HSV polymerase inhibitors. In certain embodiments, one or more antiviral agents used in a combination comprise nucleoside analogs. Examples include, without limitation, FDA approved Famvir (famciclovir), Sitavig (acyclovir), Valtrex (valacyclovir), and Zovirax (acyclovir). In one embodiment, a combination of antiviral agents comprises valacyclovir and famciclovir. In another embodiment, a combination of antiviral agents comprises acyclovir and penciclovir. In certain embodiments, one or more antiviral agents used in a combination comprise HSV helicase-primase inhibitors (HPIs). Examples include, without limitation amenamevir and pritelivir. In certain embodiments, a combination comprises an HSV polymerase inhibitor and HSP helicase-primase inhibitor.

In certain embodiments, the first and second antiviral agents can comprise valacyclovir, acyclovir, famciclovir, penciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, amenamevir, N-methancocarbathymidine (N-MCT), or a salt, solvate or combination thereof.

Both valacyclovir and famciclovir have similar mechanisms of action in that they both target viral DNA. However, the drugs differ in their pharmacokinetic profile and specificity for viral thymidine kinase. It has been discovered that there is an unexpected and surprising synergy in the action of these drugs in combination. As both of these drugs are within the same class, it was not obvious to combine them. Indeed, it has been shown that increasing amounts of each drug, used individually in a monotherapy, does not increase the efficacy of the therapy. Since both are nucleoside analogs that both target viral DNA, the current recommendations from the CDC and other authorities are to treat herpes infections with either agent, not to employ both drugs in a combination therapy.

Valacyclovir is created with the addition of the valine moiety to acyclovir, greatly improving bioavailability and resulted in a substrate for active transport mechanisms in the human intestine through the peptide transporters hPEPT-1 and/or HPT-1. There is minimal protein binding (<15%), and satisfactory distribution into body tissues including the cerebral spinal fluid (i.e., CSF). Acyclovir is phosphorylated primarily by viral thymidine kinases that create a concentration gradient that increases its uptake into infected cells. Without viral thymidine kinases, acyclovir is eliminated, basically unchanged, via tubular secretion and glomerular filtration. This is the main reason for valacyclovir's superior safety profile. It is also not metabolized by cytochrome p450, thus limiting drug interactions. The mechanism of action is threefold: 1) competitive inhibition of viral DNA polymerase; 2) chain termination of viral DNA; and 3) inactivation of viral DNA polymerase. The half-life is approximately 2.5-3.4 hours. Mean Cmax ranges from 0.83 to 5.65 ug/mL. Mean AUC ranged from 2.27-19.62 hr*ug/mL. Renal clearance following a single 1 g dose was 255 mL/min. Valacyclovir has overall bioavailability of 54.5% compared to FCV 77%.

Famciclovir has a weaker affinity for viral DNA polymerase, a shorter plasma half-life (2-2.5 hr), but has a longer intracellular half-life (10-20 hours in HSV infected cells), as well as high-intracellular concentrations versus valacyclovir. The time to reach maximum concentration ranges from 0.5-0.75 hours versus 1.6-1.9 hrs for valacyclovir. Famciclovir also has high bioavailability at 77%. Famciclovir does not use peptide transporters hPEPT-1 or HPT-1, and thus should be more efficacious in subjects who have defects related to these transporters.

The combination of Valacyclovir and Famciclovir is useful for the prevention of human herpes virus infections (i.e., pre-exposure prophylaxis) as well as the treatment and prevention of recurrences of symptoms due to herpes viruses (i.e., post-exposure prophylaxis). The combination is non-toxic at doses producing potent antiviral activity, and is active and bioavailable by the oral route of administration.

Another nucleoside inhibitor of HSV polymerase is N-methanocarbathymidine (N-MCT), which is converted into the active triphosphate metabolite by a three step phosphorylation process, one step of which is selectively accomplished by HSV-TK. N-MCT is inhibits HSV-1, HSV-2, HSV-8 (Kaposi's Sarcoma Virus), as well as Vaccinia and Cowpox viruses, is cytotoxic only in virus-infected cells, is active against acyclovir-resistant HSV and cidofovir-resistant cowpox virus, is equally or more potent than the antiviral drugs acyclovir, ganciclovir and cidofovir, is non-toxic at doses producing potent antiviral activity, and is active and bioavailable by the oral route of administration.

In some embodiments, the first antiviral agent comprises an HSV vaccine and optionally an adjuvant. In some embodiments, the HSV vaccine comprises GSK208141 (gD2t, GSK glycoprotein D (gD)-Alum/3-deacylated form of monophosphoryl lipid A), Herpes Zoster GSK 1437173A, gD2-A504, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, or a salt, solvate or combination thereof.

In some embodiments, the composition further comprises an additional antiviral agent. In some embodiments, the method further comprises administering to the subject an additional antiviral agent. In some embodiments, the additional antiviral agent is administered to the subject at a dosage from about 50 mg to about 1 g, for example, 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, 4000 mg, 5000 mg, 6000 mg, 8000 mg, or 10000 mg. In some embodiments, the additional antiviral agent is an HIV antiviral agent. In some embodiments, the HIV antiviral agent comprises abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the composition further comprises a contraceptive. In some embodiments, the method further comprises administering to the subject an effective dose of a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof.

In another aspect, provided herein is an HSV treatment kit comprising a) a composition comprising a dose of a first antiviral agent, or a dose of a first antiviral agent and a dose of a second antiviral agent; b) a delivery device for delivering the composition to an HSV seronegative subject; and c) instructions comprising information on how to administer the composition using the delivery device to prevent HSV infection in the HSV seronegative subject. In some embodiments, HSV prevention comprises suppression of HSV replication in the HSV seronegative subject. In some embodiments, HSV prevention comprises suppression of HSV activation in the HSV seronegative subject.

In some embodiments, the dose of the first antiviral agent is an amount useful for both prevention of HSV infection in the HSV seronegative subject and suppression of HSV in a seropositive subject. As non-limiting examples, the dose is about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, 4000 mg, 5000 mg, 6000 mg, 8000 mg, or 10000 mg of the first antiviral agent. When a second antiviral agent is present, as non-limiting examples, the dose of the second agent is about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, 4000 mg, 5000 mg, 6000 mg, 8000 mg, or 10000 mg. In some embodiments, the delivery device further provides a method for delivering the composition to the HSV seropositive subject. In some embodiments, the instructions further comprise information on how to administer the composition using the delivery device to suppress HSV reactivation in the HSV seropositive subject.

In some embodiments, the kit further comprises or is enclosed within a package. In some embodiments, the package comprises a label directed towards HSV seronegative subjects, HSV seropositive subjects and subjects of unknown HSV sero-status.

In some embodiments, the delivery device comprises an oral tablet, oral capsule, or oral solution. In some embodiments, the delivery device is a long-acting drug delivery device. In some embodiments, the long-acting delivery device comprises an injection device, intravaginal ring, transdermal patch, or a combination thereof. In some embodiments, including but not limited to tablet, capsule, or solution for ingestion, the delivery device provides systemic delivery.

In some embodiments, the first antiviral agent comprises valacyclovir, acyclovir, famciclovir, pritelivir, penciclovir, ganciclovir, valganciclovir, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, amenamevir, N-methancocarbathymidine (N-MCT), or a salt, solvate or combination thereof.

In some embodiments, the dose of the first antiviral agent is from about 5 mg to about 1 g or higher, for example, about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, 4000 mg, 5000 mg, 6000 mg, 8000 mg, or 10000 mg.

In some embodiments, the kit further comprises a second antiviral agent. In some embodiments, the second antiviral agent is present in the composition at a second dose. In some embodiments, the second low dose is from about 5 mg to about 1 g, for example, about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, 4000 mg, 5000 mg, 6000 mg, 8000 mg, or 10000 mg. In some embodiments, the second antiviral agent is an HSV antiviral agent. In some embodiments, the second antiviral agent is an HIV antiviral agent. In some embodiments, the HIV antiviral agent comprises abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the kit further comprises a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof.

In another aspect, provided herein is a method of preventing HSV infection in an HSV seronegative subject, the method comprising administering to the subject a composition comprising a very high dose of a first antiviral agent after physical contact with a partner who is seropositive for HSV. In some embodiments, the method further comprises administering to the subject a low dose of a second antiviral agent prior to physical contact with the HSV seropositive partner. In some embodiments, the second antiviral agent comprises a same active agent as the first antiviral agent. In some embodiments, the second antiviral agent comprises a different active agent than the first antiviral agent. In some embodiments, the physical contact occurs during one occasion. In some embodiments, the physical contact occurs during two or more separate occasions.

In some embodiments, the physical contact occurs with the HSV seropositive partner and one or more additional partners. In some embodiments, the subject is or will be in an ongoing mutually-monogamous sexual relationship with the HSV seropositive partner. In some embodiments, the subject is not or will not be in a mutually-monogamous sexual relationship with the HSV seropositive partner. In some embodiments, the HSV seropositive partner is aware of their HSV sero-status. In some embodiments, the HSV seropositive partner is unaware of their HSV sero-status. In some embodiments, the HSV seropositive partner is undergoing HSV suppression therapy comprising the administration of a suppressive antiviral agent to the HSV seropositive partner. In some embodiments, the method further comprises administering to the HSV seropositive partner a suppressive antiviral agent. In some embodiments, the suppressive antiviral agent comprises a same active agent as the first antiviral agent. In some embodiments, the suppressive antiviral agent comprises a different active agent than the first antiviral agent.

In some embodiments, the physical contact is sexual contact. In some embodiments, the subject and the HSV seropositive partner use a physical barrier during sexual contact. In some embodiments, the physical contact is kissing.

In some embodiments, the subject is exposed to HSV from the HSV seropositive partner during physical contact. In some embodiments, the administered composition suppresses HSV replication in the subject. In some embodiments, the administered composition suppresses HSV activation in the subject. In some embodiments, the administered composition reduces the risk of HSV infection in the subject. In some embodiments, the risk of HSV infection in the subject is reduced by at least about 50%, 60%, 70%, 80%, 90%, or 95%.

In some embodiments, the method further comprises determining the very high dose of the first antiviral agent. In some embodiments, the method further comprises determining a delivery mechanism for administering the composition to the subject. In some embodiments, the delivery mechanism comprises a long-acting drug delivery device. In some embodiments, the long-acting drug delivery device comprises an injection device, intravaginal ring, transdermal patch, or a combination thereof.

In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, amenamevir, N-methancocarbathymidine (N-MCT), or a salt, solvate or combination thereof.

In some embodiments, the first antiviral agent comprises an HSV vaccine and optionally an adjuvant. In some embodiments, the HSV vaccine comprises GSK208141 (gD2t, GSK glycoprotein D (gD)-Alum/3-deacylated form of monophosphoryl lipid A), Herpes Zoster GSK 1437173A, gD2-ASO4, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, or a salt, solvate or combination thereof.

In some embodiments, the very high dose of the first antiviral agent is from about 500 mg to about 10,000 mg, for example, about 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, or 2500 mg, 3000 mg, 4000 mg, 5000 mg, 6000 mg, 8000 mg, or 10000 mg. In some embodiments, the very high dose of the first antiviral agent is an amount greater than an amount useful for treating an initial outbreak of HSV in a seropositive patient.

In some embodiments, the composition further comprises an additional antiviral agent. In some embodiments, the method further comprises administering to the subject an additional antiviral agent. In some embodiments, the additional antiviral agent is administered to the subject at a dosage from about 500 mg to about 10,000 mg, for example, about 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 3000 mg, 4000 mg, 5000 mg, 6000 mg, 8000 mg, or 10000 mg. A dose up to 1000 mg is designated a "low dose." In some embodiments, the additional antiviral agent is an HIV antiviral agent. In some embodiments, the HIV antiviral agent comprises abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doraviride, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, enfuvirtide, vicriviroc, cenicriviroc, Ibalizumab, fostemsavir (BMS-663068), ibalizumab (TMB-355, TNX-355), PRO 140, b12 antibody, DCM205, DARPins, caprine antibody, VIR-576, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the composition further comprises a contraceptive. In some embodiments, the method further comprises administering to the subject an effective dose of a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof. In some embodiments, the contraceptive is an emergency contraceptive.

In another aspect, provided herein is an HSV treatment kit comprising a) a composition comprising a very high dose of a first antiviral agent; b) a delivery device for delivering the composition to an HSV seronegative subject; and c) instructions comprising information on how to administer the composition using the delivery device to prevent HSV infection in the HSV seronegative subject after the HSV seronegative subject is exposed to HSV. In some embodiments, HSV prevention comprises suppression of HSV replication in the HSV seronegative subject. In some embodiments, HSV prevention comprises suppression of HSV activation in the HSV seronegative subject.

In some embodiments, the very high dose of the first antiviral agent is an amount useful for both prevention of HSV infection in the HSV seronegative subject after exposure to HSV and treatment of an initial outbreak of HSV in an HSV seropositive subject. In some embodiments, the very high dose of the first antiviral agent is an amount greater than an amount useful for treating an initial outbreak of HSV in an HSV seropositive subject.

In some embodiments, the delivery device further provides a method for delivering the composition to the HSV seropositive subject. In some embodiments, the instructions further comprise information on how to administer the composition using the delivery device to treat an HSV outbreak in the HSV seropositive subject.

In some embodiments, the kit further comprises or is enclosed within a package. In some embodiments, the package comprises a label directed towards HSV seronegative subjects, HSV seropositive subjects and subjects of unknown HSV sero-status.

In some embodiments, the delivery device comprises an oral tablet, oral capsule, or oral solution. In some embodiments, the delivery device is a long-acting drug delivery device. In some embodiments, the long-acting delivery device comprises an injection device, intravaginal ring, transdermal patch, or a combination thereof.

In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or a salt, solvate or combination thereof.

In some embodiments, the very high dose of the first antiviral agent is from about 500 mg to about 2500 mg, for example, about 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 3000 mg, 4000 mg, 5000 mg, 6000 mg, 8000 mg, or 10000 mg.

In some embodiments, the kit further comprises a second antiviral agent. In some embodiments, the second antiviral agent is an HSV antiviral agent. In some embodiments, the second antiviral agent is an HIV antiviral agent. In some embodiments, the HIV antiviral agent comprises abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the kit further comprises a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norg-estrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof. In some embodiments, the kit comprises an emergency contraceptive.

BRIEF DESCRIPTION OF THE FIGURES

The following detailed description, given by way of example, but not intended to limit the invention solely to the specific embodiments described, may best be understood in conjunction with the accompanying drawings.

Figure 1:
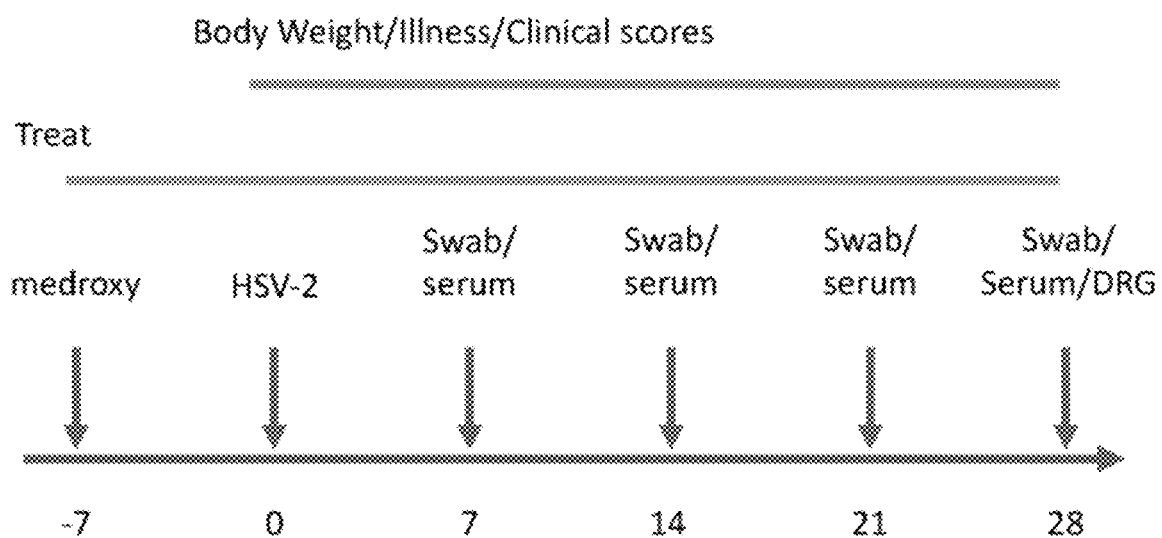
FIG. 1. Experimental Design. Day $-7$ and day $-1$: weigh mice and treat with medroxyprogesterone; Day $-7$: dose mice daily; Day 0: infect mice with $10^5$ HSV-2 MS intravaginally; days 1-28: treat mice daily, weigh mice, clinical scores taken, euthanize mice that meet IACUC humane endpoint guidelines; Days 7, 14, 21, and 28: collect vaginal swabs; Day 28: end of study, collect DRG.

The figures herein are for illustrative purposes only and are not necessarily drawn to scale. 0.000510796

DETAILED DESCRIPTION OF THE INVENTION

The current standard practice for preventing HSV infection involves suppressive treatment of an HSV seropositive individual to reduce transmission of the virus to an HSV seronegative individual. As described previously, these methods rely on the compliance of an HSV seropositive individual and often do not provide adequate protection for the HSV seronegative individual. Described herein, in various aspects, are methods for the prevention of HSV infection in a seronegative individual comprising administering to the seronegative individual a composition comprising one or more antiviral agents. If the HSV seronegative individual is in a relationship with an HSV seropositive partner (i.e., an HSV discordant relationship), the methods optionally further comprise suppressive treatment of the HSV seropositive individual, providing a second layer of protection for the seronegative individual. In one aspect, provided are compositions comprising one or more antiviral agents useful for the prevention of HSV infection in an HSV seronegative individual, wherein the compositions protect the seronegative individual against the transmission of shedding virus from the seropositive individual. These antiviral compositions for protecting HSV seronegative individuals are optionally also useful in suppressive treatment of HSV seropositive individuals. In some aspects of the methods described herein, the HSV compositions further comprise and/or are administered with, one or more additional antiviral agents. For example, the compositions described herein comprise one or more HSV antiviral agents and one or more human immunodeficiency virus (HIV) antiviral agents. In some cases, the HSV antiviral agent also treats or prevents infection by another virus, such as HIV. In additional embodiments, a composition comprising an HSV antiviral, and optionally one or more additional antiviral agents, further comprises and/or is administered with a contraceptive agent. As such, the present disclosure, in various embodiments, provides compositions and methods for the prevention of HSV infection in an HSV seronegative individual, while optionally further preventing pregnancy and/or infection by additional viruses.

In one aspect of the disclosure, described herein are compositions and methods for the prevention of HSV infection in an HSV seronegative individual at risk for exposure to HSV. In some cases, these compositions are referred to as pre-exposure compositions or HSV pre-exposure compositions. In some embodiments, the HSV seronegative individual is at risk for exposure to HSV through one or more incidents of sexual contact with one or more partners, where the one or more partners is HSV seropositive or has an unknown HSV sero-status. As one example, the HSV seronegative individual at risk for exposure to HSV is likely to engage in one or more incidents of sexual contact with the same partner. In some cases, the seronegative individual and the partner are in a monogamous relationship. In other cases, the seronegative individual and the partner are not in a monogamous relationship. As another example, the HSV seronegative individual at risk for exposure to HSV is likely to engage in one or more incidents of sexual contact with one or more different partners. In various embodiments, the pre-exposure compositions described herein comprise one or more antiviral agents at a low dose, for example, a dose that is the same or 10%, 20%, 30%, 40%, 50%, 60%, 70%, 80%, or 90% smaller than the dose typically administered to an HSV seropositive individual for suppression therapy.

In another aspect, described herein are compositions and methods for the prevention of HSV infection in an HSV seronegative individual after exposure to HSV. In some cases, these compositions are referred to as post-exposure compositions or HSV post-exposure compositions. In some embodiments, the HSV seronegative individual is exposed to HSV through one or more incidents of sexual contact with one or more partners, where the one or more partners is HSV seropositive. In some cases, the HSV seropositive partner is aware of their seropositive status. In other cases, the HSV seropositive partner is unaware of their seropositive status. As one example, the HSV seronegative individual is exposed HSV through one or more incidents of sexual contact with the same HSV seropositive partner. In some cases, the seronegative individual and the partner are in a monogamous relationship. In other cases, the seronegative individual and the partner are not in a monogamous relationship. As another example, the HSV seronegative individual is exposed to HSV through one or more incidents of sexual contact with one or more different partners. In various embodiments, the post-exposure compositions described herein comprise one or more antiviral agents at a high dose, for example, a dose that is the same or 10%, 20%, 30%, 40%, 50%, 60%, 70%, 80%, or 90% greater than the dose typically administered to an HSV seropositive individual for therapy after an initial outbreak.

In some embodiments, an HSV composition or an antiviral composition refers to a pre-exposure composition. In some embodiments, an HSV composition or an antiviral composition refers to a post-exposure composition. In some embodiments, an HSV composition or an antiviral composition refers to a composition comprising one or more antivirals for suppressive therapy of an HSV seropositive individual. In some embodiments, an HSV composition or an antiviral composition refers to both pre-exposure and post-exposure compositions. In further embodiments, an HSV composition or an antiviral composition refers to pre-exposure compositions, post-exposure compositions, and compositions for suppressive therapy.

In one aspect of the disclosure, provided herein are compositions and methods for the prevention of HSV infection in an HSV seronegative subject in an HSV discordant relationship with an HSV seropositive subject. In some embodiments, an HSV seronegative subject is administered a first composition comprising one or more first antiviral agents and the HSV seropositive subject is administered a second composition comprising one or more second antiviral agents. In some cases, a first antiviral agent, or a pharmaceutically acceptable salt or solvate thereof, comprises the same active agent as a second antiviral agent, or a pharmaceutically acceptable salt of solvate thereof. In some cases, a first antiviral agent comprises a different active agent than a second antiviral agent. In some cases, a first antiviral agent is administered in a dosage that is the same or different as the dosage of the second antiviral agent. In some cases, the first composition is delivered using the same delivery mechanism as the second composition. In other cases, the first composition is delivered using a different delivery mechanism as the second composition. In some cases, these methods further provide enhanced HSV infection prevention in seronegative individuals by improving delivery of antiviral agents to the seropositive individual and/or the seronegative individual, for example, by using long-acting drug delivery mechanism. In some embodiments, the compositions administered to the HSV seronegative individual are pre-exposure compositions for prophylactic treatment. In some embodiments, the compositions administered to the HSV seronegative individual are post-exposure compositions for prophylactic treatment. Prophylactic treatment of an HSV seronegative individual, when used in combination with suppressive treatment of the HSV seropositive individual, provides a second opportunity to inactivate any virus that has been shed by the seropositive individual so that there are insufficient quantities of HSV to create a productive, sustainable infection in the new host and thus creates an added layer of protection against HSV infection. In some embodiments, this enhanced HSV infection prevention is further amplified when the methods further comprise safe sex practices. In addition, treating the seronegative as well as the seropositive person can increases the likelihood of compliance and removes the stigma of HSV infection, thereby improving the likelihood of self-diagnosis and treatment in seropositive individuals. Under a scenario in which both seropositive and seronegative individuals are taking antivirals, seropositive individuals no longer face a stigma and all individuals are acting in a way that greatly reduces transmission of HSV. This can significantly improve HSV treatment and transmission prevention and, by extension, HIV transmission prevention.

In some embodiments, provided herein are methods for administering an antiviral composition to an HSV seronegative individual, provided that the HSV seronegative individual is associated with a risk category for infection with HSV. In some aspects of the methods described herein, the methods for preventing HSV infection in an HSV seronegative individual comprise determining a risk category of the HSV seronegative individual. In some embodiments, an individual associates with a different HSV risk category over a period of time. In such instances, the methods of administering an antiviral composition are optionally modulated to align with this change in risk category. For example, in some instances, an individual no longer in an HSV risk category discontinues use of an antiviral composition. In some cases, an HSV seronegative individual is at risk for infection with HSV through exposure from an HSV seropositive partner, wherein the HSV seronegative and HSV seropositive individuals are in a monogamous, HSV discordant relationship. In some cases, an HSV seronegative individual is at risk for infection with HSV through exposure from an HSV seropositive partner, wherein the two individuals are not in a monogamous relationship. In this instance, the risk for infection can occur during a single or multiple physical encounters with the HSV seropositive partner. In some cases, an HSV seronegative individual is at risk for infection with HSV through exposure from multiple HSV seropositive partners, wherein the individuals are not in a monogamous relationship. In this instance, the risk for infection can occur during a single or multiple physical encounters with the HSV seropositive partners. In some cases, an HSV seronegative individual is at risk for infection with HSV through exposure from one or more partners of unknown HSV status, wherein the individuals are not in a monogamous relationship. In this instance, the risk for infection can occur during a single or multiple physical encounters with the one or more partners. In some embodiments, an HSV individual at risk for exposure to HSV is administered a pre-exposure composition comprising a low dose of at least one antiviral agent. In some embodiments, an HSV individual suspected of or having been exposed to HSV is administered a post-exposure composition comprising a high dose of at least one antiviral agent.

In some embodiments, provided herein are methods for administering an antiviral composition to an individual of unknown HSV sero-status. In some cases, the individual is HSV seropositive and does not know their sero-status. In other cases, the individual is HSV seropositive and does not admit to others that they are HSV seropositive. In some cases, the individual is HSV seronegative and does not know their sero-status. Not knowing their sero-status or being in denial of it, can prevent individuals from warning seronegative persons of the risk of transmission. In some embodiments, the methods described herein comprise administering an antiviral agent to an individual of unknown status in an amount that is both effective for prevention of HSV infection in an HSV seronegative subject and effective for HSV suppression therapy in an HSV seropositive subject. In some cases, the effective amount is a low dose of an antiviral agent. In such instances, HSV testing is not required for administering an antiviral composition. Common methods for testing for HSV sero-status include immunoassays, cell culturing and nucleic acid detection, for example, using polymerase chain reaction. As the standard of care does not currently provide test kits readily performed without assistance of a laboratory and health care personal, HSV sero-status is not easily ascertained. In various aspects, the methods and compositions provided eliminate the need for determining sero-status.

In some embodiments, provided herein are methods for administering an antiviral composition to an individual of known HSV seropositive status. The stigma associated with HSV infection can cause individuals to avoid the uncomfortable conversation with a doctor that is necessary for HSV testing and/or obtaining antiviral drugs. In some cases, the HSV seropositive individual is administered a same dosage of an antiviral that an HSV seronegative individual would be administered to prevent HSV infection, eliminating the need for the HSV seropositive individual to admit their sero-status.

The methods for preventing HSV infection in an HSV seronegative individual, in various embodiments, comprise administering to the HSV seronegative individual a composition comprising one or more antiviral agents. In some embodiments, the methods comprise determining a mechanism of administering the HSV composition. In some embodiments, the methods comprise determining a risk category of the HSV seronegative individual. In some embodiments, the methods comprise determining an antiviral agent dosage amount effective to suppress HSV replication, HSV re-activation, or both HSV replication and HSV re-activation. In some embodiments, the methods comprise determining a route of administration of the composition and a delivery mechanism, for example, oral tablet, transdermal patch or intravaginal ring. In some embodiments, the methods comprise determining an anatomical location on the individual for engagement of an antiviral composition delivery mechanism. In some embodiments, the methods comprise maintaining delivery of an antiviral composition to an individual for a therapeutically effective amount of time, for example, the delivery mechanism provides sustained or long-acting delivery of an active agent of the composition. Long-acting drug delivery mechanisms include, without limitation, injection devices, intravaginal rings, and transdermal patches. As a non-limiting example, the delivery mechanism is an intravaginal ring which is maintained within the subject and releases an active agent of a composition to the subject for a therapeutically effective amount of time.

In one aspect, provided herein are compositions comprising one or more antiviral agents and methods of administering one or more antiviral agents, wherein the compositions are administered using a long-acting delivery mechanism via a long-acting delivery device. In some embodiments, the antiviral compositions are administered to HSV seronegative individuals. In some embodiments, the antiviral compositions are administered to HSV seropositive individuals. In further embodiments, the compositions are administered to both HSV seropositive and HSV seronegative individuals, wherein the compositions may have the same or different active antiviral agents. In some embodiments, the long-acting delivery device is an intravaginal ring. In some embodiments, the long-acting delivery device is an injectable device. In some embodiments, the long-acting delivery device is a transdermal patch. Long-acting delivery mechanisms, in many cases, provide a higher average, more consistent, and/or more reliable concentration of the antiviral drug within the bloodstream of a subject over a longer period time, as compared to oral administration of the same antiviral drug dosage. In some instances, administration of an antiviral composition described herein via a long-acting delivery mechanism reduces the risk of non-compliance in the subject. For example, compliance in subjects administered an antiviral composition via a long-acting drug delivery device is at least about 10%, 20%, 30%, 40%, 50%, 60%, 70%, 80%, 90%, 100% or greater than compliance in subjects administered an antiviral composition via an oral formulation. Subjects may be less likely to forget to take a dosage when it is automatically administered through a long-acting drug delivery device. In some embodiments, the long-acting drug delivery device delivers an antiviral agent, such as an HSV antiviral, and another antiviral agent, such as one that prevents HIV. In other or additional embodiments, the long-acting drug delivery device delivers an antiviral agent and a contraceptive.

In further embodiments, provided herein are methods and compositions for reducing the incidence of HSV infection in a seronegative individual and therefore the incidence of HIV infection. In some cases, reducing the incidence of HSV infection can indirectly reduce the incidence of HIV infection. As previously discussed, the risk of contracting HIV is higher when there is an HSV co-infection. This is true not only because HSV infection creates scarring and other flaws in the skin that reduce the skin's effectiveness as a barrier to HIV, but also because the presence of HSV activates the immune system in such a way that it becomes more vulnerable to invasion by HIV. In addition, HSV has been shown to upregulate the chemokine receptor CCR5, the primary co-receptor for HIV, which is a suspected mechanism for the increased risk of transmission of HIV in HSV positive people. Hence, reducing the incidence of HSV can greatly reduce the risk of HIV infection, thus reducing a severe medical risk and significant public health cost.

The terms "synergy" and "synergistic" mean that the effect achieved with the compounds used together is greater than additive sum of effects that are achieved when using the compounds separately, i.e. greater than what would be predicted based on the two active ingredients administered separately. A synergistic effect may be attained when the compounds are 1) co-formulated such that they are administered or delivered simultaneously in a combined formulation 2) delivered or administered in separate formulations either in alternation or in parallel or 3) by some other regimen. When delivered/administered in alternation, the synergistic effect may be obtained when they are done in a sequential manner e.g. in separate tablets, pills, capsules or injections by different syringes. In general, during alternation therapy an effective dose of each active ingredient is administered sequentially where as in combination therapy effective doses are administered together. A synergistic antiviral effect is an antiviral effect where the combined effect is greater than the predicted additive effects of each individual component.

The term "physiologically functional derivative" means a pharmaceutically active compound with equivalent on near equivalent physiological functionality to valacyclovir or famciclovir when administered in combination with another pharmaceutically active compound in a combination of the invention. As used herein, "physiologically functional derivative" includes and physiologically acceptable salt, ester, prodrug, solvate, stereoisomer including enantiomer, diastereomer or stereoisomerically enriched or racemic mixture or any other compound which upon administration to a subject in need, is capable of providing directly or indirectly such a compound or an antivirally active metabolite or reside thereof.

The term herpes virus includes all alpha, beta, and gamma herpes viruses, including but not limited to herpes simplex virus type 1 (HSV-1), herpes simplex virus type 2 (HSV-2), varicella zoster virus (VZV), cytomegalovirus (CMV), Epstein-Barr virus (EBV), Kaposi's Sarcoma associated Herpes Virus (KSHV), HHV-6, HHV-7. It has been shown that herpes virus such as those listed above are implicated in diverse disease sates such neonatal herpes, herpes encephalitis, Alzheimer's Disease, senile dementia, Multiple Sclerosis, Systemic Lupus Erythematosus (SLE), Rheumatoid arthritis, Juvenile idiopathic arthritis (JIA), inflammatory bowel disease, celiac disease, type 1 diabetes, chronic fatigue syndrome, mononucleosis, as examples.

It has recently been shown that treatment with valacyclovir before exposure could prevent herpes infection including latency. Thus, treatment with valacyclovir, famciclovir alone or in combination will prevent herpes-related illness.

The present invention provides novel combinations of two or more active ingredients being employed together. In some embodiments, a synergistic antiviral effect is achieved. The term "synergistic antiviral effect" is used to denote an antiviral effect that is greater than the predicted purely additive effects of using each antiviral component individually.

While it is possible for the active ingredients of the combination to be administered alone and separately, it is preferable to administer them as a combination. A two-part or three-part combination may be administered simultaneously or sequentially. When administered sequentially, the combination may be administered in one, two or three administrations. Preferably, two-part or three-part combinations are administered in a single pharmaceutical dosage form. Examples include a single tablet including both valacyclovir and famciclovir, a single tablet of valacyclovir and a single tablet of famciclovir, two tablets of valacyclovir and a single tablet of famciclovir, and two tablets of valacyclovir and two tablets of famciclovir.

The compounds of the combination may be administered 1) simultaneously by combination of the active ingredients in a co-formulation or 2) by alternation, i.e. delivering the active ingredients sequentially, serially, in parallel or simultaneously in spate pharmaceutical formulations. In alternation therapy, the delay in administering the second (or optionally the third compound) would be such as to note lose the synergistic effect of the combination. The combination can be administered in either co-formulation or alternation therapy to achieve peak plasma concentrations such as but not limited to 0.001 to 200 uM.

When the individual active ingredients of the combination are administered separately they are generally each presented as a pharmaceutical formulation. It will be understood that the administration of the combination of the invention by means of a single patient pack, or patient packs of each formulation, within a package insert instructing the patient as to the correct use of the invention is a desirable additional feature of this invention.

The combination therapies of the invention include 1) a combination of valacyclovir and famciclovir or 2) a combination containing a physiologically functional derivative of either or both thereof.

The combination may be formulated in a unit dosage formulation comprising a fixed amount for a periodic, e.g. daily dose or subdose of the active ingredients.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable or the intended method of administration.

The combinations of the invention may conveniently be presented as a pharmaceutical formulation in a unitary dosage form. A convenient unitary dosage formulation contains the active ingredient in any amount from 1 mg to 5 g each, for example but not limited to 250 mg to 1 g. The synergistic effects of valacyclovir in combination with famciclovir may be realized over a wide ratio for example (1:100 to 100:1 (valacyclovir:famciclovir). In certain embodiments, the ratio can range from one embodiment, the ratio may range 1:5 to 5:1, for example, about 1:5, about 1:4, about 1:3, about 1:2, about 1:1, about 2:1, about 3:1, about 4:1, or about 5:1. In certain embodiments the range is from about 1:2 to about 2:1. In another embodiment there will be an approximately equal amount of valacyclovir and famciclvor. In other exemplary co-formulations there may be more or less valacyclovir than famciclovir. Other ratios and amounts of the compounds are contemplated within the scope of the invention.

It will be appreciated by those skilled in the art that the amount of active ingredients in the combination of the invention required for use in treatment will vary according to a variety of factors including the nature of the condition being treated, the age and condition of the patient and will ultimately be at the discretion of the health care provider or treating physician. Factors include by are not limited to age, renal clearance, weight, age general condition, especially renal function, nature and severity of the disease to be treated. For example cytomegalovirus (CMV) typically requires higher dosages to reach efficacy.

It is also possible to combine any two of the active ingredients in a unitary dosage form for simultaneous or sequential administration with a third active ingredient. The three-part combination may be administered simultaneously or sequentially. When administered sequentially, the combination may be administered in one, two or three administrations. Third active ingredients have anti-herpes virus activity. Exemplary third active ingredients to be administered in combination with valacyclovir and famciclovir include but are not limited to particularly useful third agents, by way of example and not limitation are helicase primase inhibitors, SM inhibitors, spironolactone, emtricitabine and lamivudine, pegylated interferon, ribavirin, boceprevir, telaprevir, simeprevir, sofosbuvir, ledipasvir/sofobuvir, tenofovir, ombitasvir, paritaprevir, ritonavir.

Formulation of the present invention suitable for oral administration may be as capsules, caplets, cachets, tablets each containing a predetermined amount of the active ingredients as a powder or granules; as a solution or a suspension in aqueous or non-aqueous liquid; or as an oil-in-water emulsion or a water-in-oil liquid emulsion. The active ingredient may also be presented as a bolus, electuary or paste. The oral formulation of tablets may be coated or score and may be formulated so as to provide a slow or controlled release of the active ingredients. Tablets may optionally be provided with an enteric coating, to provide release in parts of the gut other than the stomach.

Viruses and Viral Diseases

Provided herein, in various aspects, are methods for the prevention of viral infection in a subject comprising administering to the subject a composition comprising an effective dose of at least one antiviral agent. The methods and compositions described herein relate to any infective virus. In some embodiments, reference to a virus is not limited to a single virus and is inclusive of one or more infective viruses. In exemplary embodiments, a virus is at least one herpes simplex virus (HSV). In various instances, reference to HSV is inclusive of all infectious viruses and is not limited to herpes simplex virus. In some embodiments, a virus is at least one human immunodeficiency virus (HIV). In some cases, the methods prevent infection by both HSV and HIV viruses. In non-limiting examples, at least one virus includes at least one of herpes virus, HIV-I, HIV-2, simian immunodeficiency virus (SIV), feline leukemia virus, picornavirus family, respiratory syncytial virus (RSV), influenza, adenovirus, rhinovirus, enterovirus, poliovirus, rubella virus, paramyxovirus, rotavirus, neurotropic virus, or oncovirus. In some embodiments, the picornavirus family includes but is not limited to picornavirus, poliovirus, rhinovirus, enterovirus (coxsackie virus), hepatitis (hepatitis virus type A, hepatitis virus type B, hepatitis virus type C), aphthovirus, parechovirus, and encephalomyocarditis virus.

In some embodiments, the herpes virus includes, but is not limited to, herpes simplex virus-1, herpes simplex virus-2, varicella-zoster (VZV, i.e. chicken pox, shingles, human herpes virus 3), Epstein-Ban (human herpes virus 4), cytomegalovirus (human herpes virus 5), roseolovirus (human herpes virus 6 and 7), and Karposi's sarcoma-associated herpes virus (human herpes virus 8). HSV-1 typically produces cold sores and in some instances, genital herpes in infected persons. HSV-2 typically produces genital herpes in infected persons. Significant manifestations of HSV-1 and HSV-2 include oropharyngeal infections, skin infections, ocular infections, and central nervous system disorders such as meningitis and encephalitis.

Neonatal herpes simplex virus (HSV) infection affects newborn infants and has high mortality and significant morbidity. Incidence estimates range from 1/3,000 to 1/20,000 births. In most cases, a parent with oral or genital herpes transfers the disorder to an offspring before, during, or shortly after birth. Manifestations generally occur between the 1st and 3rd wk of life but rarely may not appear until as late as the 4th wk. Neonates may present with local or disseminated disease. Skin vesicles are common with either type, occurring in about 70% overall. Neonates with no skin vesicles usually present with localized CNS disease. In neonates with isolated skin or mucosal disease, progressive or more serious forms of disease frequently follow within 7 to 10 days if left untreated. Neurological infection is present in about a third of neonatal HSV infections and associated with permanent neurological abnormalities.

In some embodiments, HIV includes HIV-1 (HIV type-1), HIV-2 (HIV type-2) and SIV. HIV-1 includes, but is not limited to, extracellular virus particles and the forms of HIV-1 associated with HIV-1 infected cells. In some instances, HIV-1 represents any of the known major subtypes (Classes A, B, C, D E, F, G and H), recombinant strains or outlying subtype (Group 0), including laboratory strains and primary isolates. HIV-2 includes, but is not limited to, extracellular virus particles and the forms of HIV-2 associated with HIV-2 infected cells. SIV is an HIV-like virus that infects monkeys, chimpanzees, and other nonhuman primates.

In some embodiments, a viral infection refers to a verified presence of a viral antibody, viral antigen, and/or viral nucleic acid in a subject using viral diagnostic tests known to those skilled in the art (e.g. immunoassays such as ELISAs, Western blot, and lateral flow assays; and PCR). In exemplary embodiments, an HSV infection refers to the verified presence of anti-HSV antibody or HSV nucleic acid. In some instances, an HSV seropositive individual is an individual who has detectable anti-HSV antibody in their blood. In some instances, an HSV seronegative individual is an individual who does not have detectable anti-HSV antibody in their blood. In some cases, an HSV seronegative individual has been exposed to HSV, but HSV has not established an infection and/or the individual has not yet seroconverted so that anti-HSV antibodies are not yet detectable.

HSV Associated Diseases and Disorders

Human herpes virus have been implicated in a host of diseases. Herpes viruses such as Epstein Barr has been implicated in a host of auto-immune and other diseases. For example, Herpes Simplex Virus (HSV-1 and 2), Varicella. Zoster Virus (VZV) and other human herpes viruses have been implicated in Alzheimer's disease. Accordingly, compositions and methods of the invention are useful in treatment or prophylactic treatment of Alzheimer's disease, senile dementia, multiple sclerosis, systemic lupus erythematosus (i.e., SLE), rheumatoid arthritis, juvenile idiopathic arthritis (i.e., JIA), inflammatory bowel disease (i.e., IBD), celiac disease, type 1 diabetes, mononucleosis, among others. Itzhaki describes the development of senile dementia in subjects with marked overt signs of disease caused by varicella zoster virus (VZV), or by HSV, and the effects of antiviral treatment (see Itzhaki, "Corroboration of a Major Role for Herpes Simplex Virus Type 1 in Alzheimer's Disease," Frontiers in Aging Neuroscience, Vol. 10, Article 324, October 2018). Harley describes the association of an EBV gene product with gene loci associated with SLE risk (see Harley et al., "Transcription factors operate across disease loci, with EBNA2 implicated in autoimmunity," Nat. Genet., Vol. 50, pp. 699-707, May 2018 May). Chen observed an association of herpes zoster with an increased risk of dementia whereas prescriptions of antiviral therap were associated with a reduced risk of dementia following diagnosis of herpes zoster (see Chen, V. C. at al., "Herpes Zoster and Dementia: A Nationwide Population-Based Cohort Study," J. Clin. Psychiatry, Vol. 79, p 16m11312, January/February 2018).

Epstein-Barr Virus (EBV) infects 90% of humans without any symptoms in most cases, but has an oncogenic potential, especially in immunocompromised individuals. Immunocompromised subjects include, without limitation, patients with primary immunodeficiencies (see, e.g., Latour et al., "Inherited Immunodeficiencies With High Predisposition to Epstein-Barr Virus-Driven Lymphoproliferative Diseases," Frontiers in Immunology, Vol. 9, pp 1103, Jun. 4, 2018), those with immune incompetence resulting from suppressive therapy in allograft transplantation, and those infected with human immunodeficiency virus (HIV). EBV-associated lymphoproliferative diseases (also termed EBV+LPD) are a group of disorders in which one or more types of lymphoid cells, i.e. B cells, T cells, NK cells, and histiorytic-dendritic cells, are infected with the Epstein-Barr virus (EBV), and proliferate excessively, leading to non-malignant, pre-malignant, and malignant lymphoproliferative disorders (LPD).

Accordingly, compositions and methods of the invention are useful in treatment or prophylactic treatment of HSV associated disorders including but not limited to Alzheimer's disease, senile dementia, multiple sclerosis, systemic lupus erythematosus (i.e., SLE), rheumatoid arthritis, juvenile idiopathic arthritis (i.e., JIA), inflammatory bowel disease (i.e., IBD), celiac disease, type 1 diabetes, mononucleosis, and genetic deficiencies exemplified by but not limited to SH2D1A/SAP deficiency (also known as the X-linked lymphoproliferative syndrome type 1-XLP-1 or Purtilo syndrome), SH2D1A/SAP deficiency (also known as the X-linked lymphoproliferative syndrome type 1-XLP-1 or Purtilo syndrome), ITK deficiency, MAGT1 deficiency and others.

Antiviral Compositions

Provided herein, in various aspects, are compositions and methods for the prevention of HSV infection in an HSV seronegative subject from an HSV seropositive subject, the methods comprising administering to the HSV seronegative subject a composition comprising an effective dose of a first antiviral agent. In various embodiments, the composition prevents the establishment of a new persistent infection in the seronegative individual after exposure to HSV. In some embodiments, the composition is administered prior to HSV exposure from a seropositive individual, e.g., the composition is a pre-exposure composition. In some embodiments, the composition is administered after HSV exposure from a seropositive individual, e.g., the composition is a post-exposure composition. In some embodiments, the composition is administered prior to and after HSV exposure to the seronegative individual.

In additional aspects, provided herein are methods for the prevention of HSV infection in an HSV seronegative subject from an HSV seropositive individual, the methods comprising administering to the HSV seronegative subject a composition comprising a first effective dose of a first antiviral agent and further comprising administering to the HSV seropositive individual a second composition comprising a second effective dose of a second antiviral agent. In some embodiments, the first antiviral agent and the second antiviral agent comprise the same active agent. In some embodiments, the first antiviral agent and the second antiviral agent comprise different active agents. In some embodiments, the composition comprising an effective dose of a first antiviral agent is useful for the prevention of HSV and one or more additional viral infections. In some embodiments, the composition comprising the first antiviral agent further comprises or is administered with an additional antiviral agent, wherein the additional antiviral agent is useful for the prevention of HSV and/or one or more additional viral infections. Additional viral infections include, without limitation, HIV, HPV, hepatitis, influenza, and diseases and conditions resulting therefrom.

In some embodiments, an antiviral agent in a composition for administration to an HSV seronegative individual inactivates HSV shed by a seropositive individual and transferred to the HSV seronegative individual. In some cases, the antiviral agent administered to an HSV seronegative individual that has been exposed to HSV reduces the amount of viable virus so that the virus is not able to produce a sustainable infection in the individual. In some cases, a further layer of protection is achieved when an HSV seropositive partner of the HSV seronegative individual is in suppressive therapy, which reduces the amount of virus transferred to the HSV seronegative individual.

In some embodiments, the compositions useful for the methods of reducing HSV viral load levels in seronegative individuals comprise two or more antivirals. In some cases, at least two of the two or more antivirals employ different mechanisms for inhibiting viral infection. In some cases, an antiviral administered to a seronegative subject is the same as an antiviral administered to a seropositive subject. In some cases, an antiviral administered to a seronegative subject is different than an antiviral administered to a seropositive subject. In some cases, two or more antivirals are administered within the same composition, or two or more antivirals are administered within two or more different compositions, to create a cumulative effect incorporating the efficacy of the various drugs against the target virus. For example, a combination of antivirals (within the same composition or co-administered within different compositions) reduces the rate of viral load levels to a greater degree than employing one of the antivirals in the combination. As another example, a combination of antivirals reduces the rate of viral shedding and transmission rate to a greater degree than employing only one of the antivirals within the combination. In some cases, combination therapy is effective in situations where a single agent may be ineffective due to, for example, drug resistance, dosing mistakes, and/or non-compliance. In some cases, combinations of antivirals having different mechanisms of action provide enhanced therapeutic effectiveness over a single antiviral.

Provided herein, in some embodiments, are compositions comprising one or more antiviral agents and methods of treating an HSV and HIV seronegative individual with said compositions to prevent HSV and/or HIV infection. In some instances, at least one of the one or more antiviral agents is an HSV antiviral agent. In some instances, at least one of the one or more antiviral agents is an HIV antiviral agent. In some cases, at least one of the one or more antiviral agents is useful for the treatment of both HSV and HIV.

Further provided herein, in various aspects, are compositions and methods for the prevention of pregnancy and HSV infection in an HSV seronegative subject. In some embodiments, the methods comprise administering to the subject a composition comprising a first antiviral agent and a contraceptive agent. In some embodiments, the methods comprise administering to the subject a first composition comprising a first antiviral agent and a second composition comprising a contraceptive agent. In various cases, the first antiviral agent further prevents HIV infection. In some cases, the compositions further comprise a second antiviral agent that prevents viral infection, such as HSV and/or HIV infection.

Antiviral Agents

A variety of antiviral agents are useful in the methods and compositions described herein for both the prevention of viral transmission from seropositive individuals to seronegative individuals and the prevention of viral infection in seronegative individuals exposed to virus. In some embodiments, a seronegative individual is treated with a composition comprising an antiviral for the prevention of viral infection in the seronegative individual. In exemplary embodiments, antiviral agents administered to a seronegative individual for infection prevention include those useful for acute and/or suppressive therapy in seropositive individuals. In some embodiments, antiviral agents are useful in the methods and compositions described herein for the prevention of HSV transmission from HSV seropositive individuals to HSV seronegative individuals. In some embodiments, an HSV seronegative individual is treated with a composition comprising an antiviral for the prevention of HSV infection in the seronegative individual. In exemplary embodiments, antiviral agents administered to an HSV seronegative individual for infection prevention include those useful for acute and/or suppressive therapy in HSV seropositive individuals.

Antiviral agents useful in the compositions and methods described herein include, without limitation, any compound or a pharmaceutically acceptable salt or solvate thereof, which is capable of inhibiting replication of a virus in a cell, such as a cell in a subject, or which is effective in treating, preventing, or delaying the onset or progression of viral infection or viral diseases or conditions arising from viral infection. In some embodiments, an antiviral agent prevents or delays initial infection of an individual exposed to a virus. In some embodiments, an antiviral agent reduces the viral burden in an individual infected with a virus. In some embodiments, an antiviral agent prolongs an asymptomatic phase of a viral infection. In some embodiments, an antiviral agent maintains low viral loads of virus in infected patients. In some embodiments, an antiviral agent increases overall health or quality of life in an individual infected with a virus. In some embodiments, an antiviral agent prolongs life expectancy of an individual infected with a virus. In a non-limiting example, the effect(s) of an antiviral agent on a subject are determined by comparing a subject treated with an antiviral with a subject not treated with an antiviral, for instance, in a clinical trial to determine whether treatment with an antiviral agent is effective in treating, preventing or delaying the onset or progression of viral infection or viral diseases or conditions arising from viral infection. In some instances, the virus is a herpes virus. In some instances, the virus is HIV. In some instances, a virus refers to more than one virus, for example, an antiviral agent administered to a subject prevents or delays infection by two or more viruses after the subject is exposed to the two or more viruses. In some cases, the two or more viruses comprise HSV and HIV.

Suitable antiviral agents useful for the compositions and methods herein include, without limitation, HSV antivirals, HIV antivirals, "off-label" drugs useful for treating viral diseases or conditions, hepatitis antivirals, human papillomavirus (HPV) antivirals, and influenza antivirals. "Off-label" drugs include drugs such as cancer agents which are useful for the treatment of a viral infection or diseases or conditions resulting therefrom, which are not currently approved for viral treatment. Antiviral agents include viral protease inhibitors, viral reverse transcriptase inhibitors, viral entry inhibitors viral co-receptor inhibitors, viral fusion inhibitors, viral maturation inhibitors, viral integrase inhibitors and viral immunogens. In some embodiments, an antiviral agent comprises RNA, e.g., siRNA, that target viral nucleic acids. In some embodiments, an antiviral agent comprises a microbicide. In some embodiments, an antiviral agent is a component of a viral patch, for example, Hansaplast® herpes patch SOS or Compeed® herpes vesicle patch.

In some embodiments, an antiviral agent useful for the prevention of a viral disease comprises an antiviral agent that when administered to an individual seronegative for infection with the viral disease, the seronegative individual has a decreased chance of becoming infected and seropositive for the virus. For example, an effective amount of an antiviral agent administered alone or in combination with one or more additional antiviral agents to a seronegative subject or population of subjects, reduces the risk of the subject or population of subjects becoming infected with a virus by at least about 10%, 20%, 30%, 40%, 50%, 60%, 70%, 80%, 90%, 95%, or 100%. In some embodiments, an antiviral agent useful for the prevention of one viral disease is also useful for the prevention of a second viral disease. For example, in some cases an HIV antiviral used to treat HIV seropositive individuals is also useful for the administration to an HSV seronegative individual to prevent the HSV seronegative individual from infection with HSV.

In some embodiments, an antiviral agent useful for the prevention of a viral disease is an HSV antiviral. In some cases, the viral disease is caused by a herpes virus, for example, HSV. In some cases, the viral disease is caused by infection with HIV. In some cases, the antiviral agent is useful for the prevention of two or more viral diseases. As a non-limiting example, the HSV antiviral is useful for the prevention of HSV and HIV. In some embodiments, an HSV antiviral includes an antiviral antibody, such as an anti-HSV antibody. Antibodies include monoclonal and polyclonal antibodies and include fragments and portions thereof, for example, Fab fragments.

In some embodiments, an antiviral agent useful for the prevention of a viral disease is an HIV antiviral. In some cases, the viral disease is caused by a herpes virus, for example, HSV. In some cases, the viral disease is caused by infection with HIV. In some cases, the viral disease is caused by a herpes virus, for example, HSV. In some cases, the antiviral agent is useful for the prevention of two or more viral diseases. As a non-limiting example, the HIV antiviral is useful for the prevention of HSV and HIV. In some embodiments, an HIV antiviral includes an antiviral antibody, such as an anti-HIV antibody.

HSV antiviral agents useful in the compositions and methods described herein include nucleoside analogs that selectively target viral DNA polymerase. In some cases, an HSV antiviral agent targets thymidine kinase. For example, HSV antiviral agents can be analogs of the natural nucleoside triphosphate dGTP, and are selectively phosphorylated in virus infected cells by viral thymidine kinase. The phosphorylation of these analogs is minimal in uninfected cells, and cellular DNA polymerases have lower affinities for the antiviral triphosphates compared with HSV polymerases. Viral DNA polymerase is selectively inhibited as viral incorporation of the analogue triphosphate into a growing DNA chain prevents continued chain elongation. Non-limiting examples of these nucleoside triphosphate analogs include acyclovir, valacyclovir, penicyclovir and famciclovir. In some cases, an HSV antiviral agent targets HSV protease. In some cases, an HSV antiviral agent inhibits viral helicase-primase complex. A non-limiting example of a helicase-primase inhibitor is pritelivir. In some cases wherein a virus is resistant to a nucleoside analog, the virus may be susceptible to a helicase-primase inhibitor or a combination of nucleoside analog and helicase-primase inhibitor. In some instances, a composition described herein comprises both a nucleoside analog and a helicase-primase inhibitor.

Non-limiting examples of HSV antiviral agents for use in the compositions and methods described herein include valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, and salts, solvates, and/or combinations thereof.

In some embodiments, an antiviral agent of a composition described herein comprises a vaccine that provides acquired immunity to a disease caused by a virus. In some cases, the composition further comprises an adjuvant. In some embodiments, described herein are compositions comprising one or more viral vaccines useful for the prevention of HSV transmission. In some embodiments, described herein are compositions comprising one or more viral vaccines useful for the prevention of HIV transmission. In some embodiments, described herein are compositions comprising one or more viral vaccines useful for the prevention of HSV and HIV transmission. In some cases, the viral vaccine compositions further comprise or are administered with one or more additional antiviral agents. In some cases, the viral vaccine compositions further comprise or are administered with one or more birth control methods.

In some embodiments, a viral vaccine useful for the prevention of one viral disease is also useful for the prevention of a second viral disease. For example, in some cases an HSV vaccine is useful for the prevention of HIV infection in an HIV seronegative individual. As another example, an HIV vaccine is useful for the prevention of HSV infection in an HSV seronegative individual. In some cases, one or more viral vaccines are useful for the prevention of one or more viral diseases. As a non-limiting example, an HIV vaccine is useful for the prevention of HSV and HIV infection in a seronegative individual. As another example, an HSV vaccine is useful for the prevention of HSV and HIV infection in a seronegative individual.

Non-limiting examples of HSV vaccines useful as antiviral agents in compositions and methods described herein include GSK208141 (gD2t, GSK glycoprotein D (gD)-Alum/3-deacylated form of monophosphoryl lipid A), Herpes Zoster GSK 1437173A, gD2-ASO4, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™) GSK324332A, and salts, solvates, and/or combinations thereof. Non-limiting examples of HIV vaccines useful as antiviral agents in compositions and methods described herein include GSK1492903A, VariZIG™, and Varivax. Non-limiting examples of adjuvants useful in antiviral compositions include QS-21, Matrix-M2, AlK(SO4)2, AlNa(SO4)2, AlNH4 (SO4), silica, alum, Al(OH)3, Ca3(PO4)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, MTP-PE), RIBI (MPL®+TDM+CWS) in a 2 percent squalene/Tween-80 emulsion, lipopolysaccharides, Freund's Complete Adjuvant (FCA), Freund's Incomplete Adjuvants, Merck Adjuvant 65, polynucleotides (e.g., poly IC and poly AU acids), wax D from *Mycobacterium tuberculosis*, substances found in *Corynebacterium parvum*, *Bordetella pertussis*, and members of the genus *Brucella*, Titermax, ISCOMS, Quil A, ALUN, Lipid A and derivatives, choleratoxin derivatives, HSP derivatives, LPS derivatives, synthetic peptide matrixes or GMDP, interleukin 1, interleukin 2, and Montanide ISA-51.

In some embodiments, an antiviral agent inhibits viral entry and/or viral fusion. Examples of entry and/or fusion inhibitors include, without limitation, maraviroc, enfuvirtide (T-20), vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, AMD11070, PRO542, SCH-C, T-1249, cyanovirin, griffithsen, lectins, pentafuside, and salts, solvates, and/or combinations thereof. In some embodiments, an antiviral agent is an HIV viral entry inhibitor. HIV viral entry inhibitors include, without limitation, CD4 receptor binding inhibitors, CD4 mimics, gp120 mimics, gp41 antagonists, anti-CD4 antibodies, CCR5 antagonists (e.g., zinc finger inhibitors), and CXCR4 co-receptor antagonists.

In some embodiments, an antiviral agent is an integrase inhibitor. Non-limiting examples of integrase inhibitors include dolutegravir, elvitegravir, raltegravir, globoidnan A, MK-2048, BI224436, cabotegravir, GSK 1265744, GSK-572, MK-0518, and salts, solvates, or combinations thereof.

In some embodiments, an antiviral agent is a reverse transcriptase inhibitor, for example, a nucleotide reverse transcriptase inhibitor and/or nucleoside reverse transcriptase inhibitor (NRTI). In some embodiments, an antiviral agent is a non-nucleoside reverse transcriptase inhibitor (NNRTI). NRTIs include, without limitation, abacavir, didanosine, emtricitabine, lamivudine, stavudine, tenofovir, tenofovir disoproxil fumarate, zidovudine, apricitabine, stampidine, elvucitabine, raciver, amdoxovir, stavudine, zalcitabine, festinavir, dideoxycytidine ddC, azidothymidine, tenofovir alafenamide fumarate, entecavir, and salts, solvates, and/or combinations thereof. NNRTIs include, without limitation, delavirdine, efavirenz, etravirine (TMC-125), nevirapine, rilpivirine, doravirine, Calanolide A, capravirine, epivir, adefovir, dapivirine, lersivirine, and salts, solvates, and/or combinations thereof. Further non-limiting examples of reverse transcriptase inhibitors include alovudine, elvucitabine, TMC-278, DPC-083, amdoxovir, (–)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (–)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, and salts, solvates, and/or combinations thereof.

In some embodiments, an antiviral agent is a protease inhibitor. Non-limiting examples of protease inhibitors include atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), and salts, solvates, and/or combinations thereof.

In some embodiments, an antiviral agent is a microbicide. Non-limiting examples of microbicides include detergents such as nonoxynol-9, sodium dodecyl sulfate and Savvy (1.0% C31G). In some embodiments, the microbicide reduces the pH of vaginal secretions, for example, Buffer-Gel®. In some embodiments, an antiviral agent comprises a polyanion microbicide. Examples of polyanion microbicides are carrageenans. Carrageenans are linear sulfated polysaccharides which can be used by viruses for initial attachment to a cell membrane, thus acting as decoy receptors for viral binding. In some embodiments, a microbicide is a nanoscale dendrimeric molecule which binds to a virus. An example of a nanoscale dendrimeric molecule is the active component of VivaGel®. An additional example of a microbicide is PRO-2000, also known as PRO 2000/5, naphthalene 2-sulfonate polymer, or polynaphthalene sulphonate.

In some embodiments, a composition comprises an active agent that is used as an antiviral "off-label" drug for the treatment or prevention of viral infection. In some cases, a composition is administered with an "off-label" drug. Non-limiting examples of "off-label" drugs useful with or in the compositions provided herein include amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, and salts, solvates, and/or combinations thereof. In some embodiments, an antiviral agent is a cancer drug, for example, ruxolitinib or tocilizumab.

In some embodiments, a composition for preventing or treating a viral infection comprises at least one of the following antiviral agents: bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 1beta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, or salts, solvates, or combinations thereof.

In some embodiments, a composition for preventing or treating a viral infection comprises at least one of the following antiviral agents: Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino) uridine, digoxin, imiquimod, interferon type III, interferon type II, interferon type I, tea tree oil, or salts, solvates, or combinations thereof.

In some embodiments, a composition for preventing or treating a viral infection comprises a hepatitis antiviral agent comprising tenofovir, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, or salts, solvates, or combinations thereof.

In some embodiments, a composition for preventing or treating a viral infection comprises an influenza antiviral comprising elderberry *Sambucus*, umifenovir, amantadine, rimantadine, oseltamivir, zanamivir, peramivir, laninamivir, or salts, solvates, or combinations thereof.

In some embodiments, a composition for preventing or treating a viral infection comprises an HPV antiviral comprising pyrrole polyamides, lopinavir, carrageenan, zinc, or salts, solvates, or combinations thereof.

In some aspects, provided are compositions comprising an antiviral agent in combination with at least one additional active agent, wherein a combination refers to a composition comprising a combination of two or more active agents or a composition comprising an antiviral agent administered in combination with one or more additional active agents. In some cases, a combination of active agents results in a synergistic effect in antiviral activity. A synergistic effect may be calculated, in one example, using the Sigmoid-Emax, Loewe, and median-effect equations.

In some embodiments, a composition comprising an antiviral agent useful for the prevention and/or treatment of a viral disease further comprises or is administered in combination with another drug or active agent for the prevention and/or treatment of the viral disease. In some cases, the composition comprises or is administered with a vaccine, gene therapy treatment, cytokine, TAT inhibitor, immunomodulator or combinations thereof. In some cases, the composition comprises or is administered with an anti-infective agent comprising an antifungal agent, an antibacterial, an antiprotozoal agent or combinations thereof. In some cases, the composition comprises or is administered with an immunomodulator, for example, pentamidine isethionate, autologous CD8+ infusion, gamma-interferon immunoglobulins, thymic peptides, IGF-I, anti-Leu3A, auto vaccination, biostimulation, extracorporeal photophoresis, cyclosporin, rapamycin, FK-565, FK-506, GCSF, GM-CSF, hyperthermia, isopinosine, rVIG, HIVIG, passive immunotherapy and polio vaccine hyperimmunization, or combinations thereof. In some embodiments, a composition comprises or is administered with a pharmacokinetic enhancer, for example, cobicistat. In some embodiments, a composition comprises or is administered with a synergistic enhancer, for example, chloroquine/quinoline enhancers of protease inhibitors, CYP3A4, hydroxyurea, leflunomide, mycophenolic acid, resveratrol, or combinations thereof.

In some embodiments, a composition useful in the methods described herein comprises a combination of active agents, at least one of which is an antiviral agent. Examples of combinations include, without limitation, maravoric and emtricitabine; maravoric, emtricitabine and raltegravir; raltegravir and emtricitabine; raltegravir and lamivudine; abacavir and lamivudine; abacavir, dolutegravir, and lamivudine; abacavir, lamivudine, and zidovudine; atazanavir and cobicistat; darunavir and cobicistat; efavirenz, emtricitabine, and tenofovir; elvitegravir, cobicistat, emtricitabine, and tenofovir; emtricitabine, rilpivirine, and tenofovir; lamivudine and raltegravir; lamivudine and zidovudine; lopinavir and ritonavir; emtricitabine and tenofovir disoproxil fumarate; lamivudine and zidovudine; lopinavir and ritonavir; inosine, acetamidobenzoic acid and dimethylaminoisopropanol; and salts, solvates, and/or combinations thereof.

In some embodiments, a composition useful in the methods described herein for the prevention of viral infection (e.g., HSV) in a seronegative subject and/or the treatment of a viral infection (e.g., HSV suppression treatment) in a seropositive subject comprises one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-ASO4, Havrix™ gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PRO542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-di chlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 1beta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *Sambucus*, umifenovir, amantadine, rimantadine, oseltamivir, zanamivir, peramivir, laninamivir, pyrrole polyamides, lopinavir, or salts, solvates, and/or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of HSV infection in a seronegative subject and/or the treatment of HSV in a seropositive subject comprises one or more of the following antivirals: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of viral infection (e.g., HSV) in a seronegative subject and/or the treatment of viral infection (e.g., HSV suppression treatment) in a seropositive subject comprises 2, 3, 4, 5 or more of the following active agents valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-ASO4, Havrix™ gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-di chlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry Sambucus, umifenovir, amantadine, rimantadine, oseltamivir, zanamivir, peramivir, laninamivir, pyrrole polyamides, lopinavir, or salts, solvates, and/or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of HSV infection in a seronegative subject and/or the treatment of HSV in a seropositive subject comprises 2, 3, 4, 5 or more of the following antiviral agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with Sarracenia purpurea, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of viral infection (e.g., HSV) in a seronegative subject and/or the treatment of viral infection (e.g., HSV suppression treatment) in a seropositive subject comprises one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with Sarracenia purpurea, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates or combinations thereof, and one or more of the following active agents: maraviroc, enfuvirtide, vicriviroc, cenicriviroc, Ibalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, B1224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates, or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of HSV infection in a seronegative subject and/or the treatment of HSV in a seropositive subject comprises 2, 3, 4, 5 or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof and 2, 3, 4, 5 or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, B1224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-di chlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

Contraceptives

Provided herein, in various aspects, are compositions comprising one or more antiviral agents and methods for the prevention of viral infection in an individual seronegative for the virus, wherein the methods comprise administering to the seronegative individual the one or more antiviral agents in combination with one or more contraceptive agents. In some cases, the antiviral compositions further comprise one or more contraceptive agents. In some cases, the antiviral compositions are administered with one or more contraceptive agents. In some embodiments, provided herein are pre-exposure compositions comprising one or more contraceptive agents. In some cases, pre-exposure compositions are administered with one or more contraceptive agents. In some embodiments, provided herein are post-exposure compositions comprising one or more contraceptive agents. In some cases, post-exposure compositions are administered with one or more contraceptive agents. In further embodiments, provided herein are compositions for the treatment of individuals seropositive for a virus comprising one or more antiviral agents and one or more contraceptive agents. In yet further embodiments, provided herein are compositions for the treatment of individuals seropositive for a virus comprising one or more antiviral agents, wherein the one or more antiviral agents are administered with one or more contraceptive agents.

Provided herein, in various aspects, are compositions comprising one or more antiviral agents and methods for the prevention of HSV infection in an HSV seronegative individual, wherein the methods comprise administering to the seronegative individual the one or more antiviral agents in combination with one or more contraceptive agents. In some embodiments, one or more antiviral agents are HSV antiviral agents. In some embodiments, one or more antiviral agents are HIV antiviral agents. In some embodiments, one or more of the antiviral agents treat or prevent HSV, HIV, or both HSV and HIV. In some cases, the antiviral compositions further comprise one or more contraceptive agents. In some cases, the antiviral compositions are administered with one or more contraceptive agents. In some embodiments, provided herein are HSV pre-exposure compositions comprising one or more contraceptive agents. In some cases, HSV pre-exposure compositions are administered with one or more contraceptive agents. In some embodiments, provided herein are HSV post-exposure compositions comprising one or more contraceptive agents. In some cases, HSV post-exposure compositions are administered with one or more contraceptive agents. In further embodiments, provided herein are compositions for the treatment of HSV seropositive individuals comprising one or more antiviral agents and one or more contraceptive agents. In yet further embodiments, provided herein are compositions for the treatment HSV seropositive individuals comprising one or more antiviral agents, wherein the one or more antiviral agents are administered with one or more contraceptive agents.

In some embodiments, a composition useful in the methods described herein for the prevention of pregnancy and the prevention of HSV infection in a seronegative subject comprises 1, 2, 3, 4 or more antiviral agents and 1, 2, 3, 4, or more contraceptive agents. In some embodiments, a composition useful in the methods described herein for the prevention of pregnancy and the prevention of HSV and HIV infection in an HSV and HIV seronegative subject comprises 1, 2, 3, 4 or more antiviral agents and 1, 2, 3, 4, or more contraceptive agents. In some embodiments, a composition useful in the methods described herein for the prevention of pregnancy and the prevention of HSV infection in a seronegative subject comprises 1, 2, 3, 4, or more antiviral agents, wherein the composition is administered with 1, 2, 3, 4, or more contraceptive agents. In some embodiments, a composition useful in the methods described herein for the prevention of pregnancy and the prevention of HSV and HIV infection in an HSV and HIV seronegative subject comprises 1, 2, 3, 4, or more antiviral agents, wherein the composition is administered with 1, 2, 3, 4, or more contraceptive agents.

In some embodiments, a contraceptive agent refers to an active agent that prevents conception or pregnancy. Non-limiting examples of contraceptive agents useful in the compositions and methods provided herein include 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof.

In some instances, reference to a contraceptive agent is inclusive of a physical barrier that prevents conception or pregnancy. In some instances, the physical barrier is a condom, cervical cap, female condom or diaphragm. In some cases, a contraceptive agent is an intrauterine device. In some cases, a contraceptive agent is a spermicide (e.g., nonoxynol, octoxynol). In some instances, a contraceptive agent is an emergency contraceptive agent that is administered after an incidence of unprotected sex, for example, in high doses. Non-limiting examples of emergency contraceptive agents include levonorgestrel, combinations of estrogen and progestin, progestin, antiprogestin (e.g., ulipristal acetate, mifepristone), and salts, solvates or combinations thereof. In some instances, a contraceptive agent is administered in combination with a post-exposure composition described herein, wherein the contraceptive agent and the post-exposure composition are configured to be administered after an incidence of unprotected sex.

In some embodiments, a composition useful in the methods described herein for the prevention of pregnancy and the prevention of viral infection (e.g., HSV) in a seronegative subject comprises a) one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-ASO4, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-di chlorophenyl)thio]-4-isopropyl-1-(4-pyridylmethyl)imidazole-2-methanol carbamic acid, (−)-12-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, Viva-Gel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 1beta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *Sambucus*, umifenovir, amantadine, rimantadine, oseltamivir, zanamivir, peramivir, laninamivir, pyrrole polyamides, lopinavir, or salts, solvates, and/or combinations thereof; and b) one or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates, or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

In some embodiments, a composition useful in the methods described herein for the prevention of pregnancy and the treatment of a viral infection (e.g., HSV suppression treatment) in a seropositive subject comprises a) one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-ASO4, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™) GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 54(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *Sambucus*, umifenovir, amantadine, rimantadine, oseltamivir, zanamivir, peramivir, laninamivir, pyrrole polyamides, lopinavir, or salts, solvates, and/or combinations thereof and b) one or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates, or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

In some embodiments, a composition useful in the methods described herein for the prevention of pregnancy and the prevention of HSV infection in a seronegative subject comprises a) 1, 2, 3, 4, 5 or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof b) 1, 2, 3, 4, 5 or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4 S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof; and c) 1, 2, 3, 4, or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

In some embodiments, a composition useful in the methods described herein for the prevention of pregnancy and the treatment of HSV in a seropositive subject comprises a) 1, 2, 3, 4, 5 or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof; b) 1, 2, 3, 4, 5 or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4 S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenyl-thio)-thymine, AG-1859, RO-033-4649, R-944, DMP-850, DMP-851, brecanavir (GW640385), or salts, solvates or combinations thereof; and c) 1, 2, 3, 4, or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

Valacyclovir Compositions

Provided herein, in various aspects, are compositions useful for the prevention of HSV infection in an HSV seronegative subject, the compositions comprising the active agent valacyclovir, or a salt or solvate thereof, wherein the compositions further comprise and/or are administered with one or more additional active agents. Further provided herein, in various aspects, are methods of preventing HSV infection in an HSV seronegative subject comprising administering to the subject a combination of valacyclovir, or a salt or solvate thereof, and one or more additional active agents. In some cases, the combination of valacyclovir and the one or more additional active agents further prevents infection by one or more additional infectious diseases, for example, HIV. In some instances, the combination of valacyclovir and the one or more additional active agents is administered together in one composition. In some instances, valacyclovir and the one or more additional active agents are co-administered in different compositions. In some embodiments, at least one of the one or more additional active agents is an antiviral agent, for example, an HSV antiviral agent, HIV antiviral agent, and/or any antiviral agent described elsewhere herein. In some embodiments, at least one of the one or more additional active agents is a contraceptive. In some embodiments, at least one of the one or more additional active agents is an antiviral agent and at least one of the one or more additional active agents is a contraceptive agent. In some instances, one or more of the active agents are administered to the HSV seronegative subject to reduce the risk of acquiring HSV infection prior to exposure to HSV. In some instances, one or more active agents are administered to the HSV seronegative subject to reduce the risk of acquiring HSV infection after exposure to HSV. In some instances, one or more of the active agents are administered to the HSV seronegative subject prior to exposure to HSV and one or more of the active agents are administered to the HSV seronegative subject after exposure to HSV. In some of those cases, the dose of one or more active agents administered prior to exposure to HSV differs from the dose of one or more active agents administered after exposure to HSV. In some instances, a contraceptive agent is administered to the HSV seronegative subject to reduce the risk of pregnancy, prior to, and/or after, the subject engages in conduct that could result in pregnancy, e.g., the same conduct that results in exposure to HSV. In some embodiments, valacyclovir and/or one or more of the one or more additional active agents are administered using an oral formulation, for example, a pill, capsule, tablet or solution. In some embodiments, valacyclovir and/or one or more of the one or more additional active agents are administered using a long-acting delivery device, for example, an intravaginal ring. In some embodiments, the methods of preventing HSV infection in the HSV seronegative subject further comprise administering to an HSV seropositive partner of the HSV seronegative subject one or more antiviral agents, for example, as suppression therapy. In some cases, the HSV seropositive partner is administered an HSV antiviral.

Examples of HSV antiviral agents include, without limitation, valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof.

In some embodiments, the methods for preventing HSV infection in an HSV seronegative subject comprise administering to the HSV seronegative subject about or at least about 200 mg, 250 mg, 300 mg, 325 mg, 350 mg, 375 mg, 400 mg, 450 mg, 500 mg, 550 mg, 600 mg, 650 mg, 700 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1700 mg, or 1800 mg of valacyclovir, or a salt or solvate thereof. In some cases, valacyclovir, or a salt or solvate thereof, is administered in a dosage from about 500 mg to about 1500 mg, or from about 500 mg to about 1000 mg. In some cases, valacyclovir, or a salt or solvate thereof, is administered 1 time per week, 2 times per week, 3 times per week, 4 times per week, 5 times per week, 6 times per week, 1 time per day, 2 times per day, 3 times per day, 4 times per day, or continuously (e.g., using a long-acting delivery device).

In some embodiments, the compositions useful for preventing HSV infection in seronegative subjects comprising valacyclovir, or a salt or solvate thereof, further comprise emtricitabine. In some embodiments, the methods for preventing HSV infection in seronegative subjects comprising administering to the subject valacyclovir, or a salt or solvate thereof, further comprise administering to the subject emtricitabine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 100 mg to about 300 mg of emtricitabine, or a salt or solvate thereof.

In some embodiments, the compositions useful for preventing HSV infection in seronegative subjects comprising valacyclovir, or a salt or solvate thereof, further comprise lamivudine. In some embodiments, the methods for preventing HSV infection in seronegative subjects comprising administering to the subject valacyclovir, or a salt or solvate thereof, further comprise administering to the subject lamivudine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 100 mg to about 300 mg of lamivudine, or a salt or solvate thereof.

In some embodiments, the compositions useful for preventing HSV infection in seronegative subjects comprising valacyclovir, or a salt or solvate thereof, further comprise glycyrrhizic acid. In some embodiments, the methods for preventing HSV infection in seronegative subjects comprising administering to the subject valacyclovir, or a salt or solvate thereof, further comprise administering to the subject glycyrrhizic acid, or a salt or solvate thereof. In some embodiments, the methods comprise administering to the HSV seronegative subject at least or about 1 mg, 2 mg, 3 mg, 4 mg, 5 mg, 6 mg, 7 mg, or 8 mg, 9 mg, 10 mg, 11 mg, 12 mg, 13 mg, 14 mg, 15 mg, 20 mg of glycyrrhizic acid, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 1 mg to about 10 mg of glycyrrhizic acid, or a salt or solvate thereof.

In some embodiments, the compositions useful for preventing HSV infection in seronegative subjects comprising valacyclovir, or a salt or solvate thereof, further comprise *Sambucus nigra*. In some embodiments, the methods for preventing HSV infection in seronegative subjects comprising administering to the subject valacyclovir, or a salt or solvate thereof, further comprise administering to the subject *Sambucus nigra*, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of *Sambucus nigra*, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 100 mg to about 200 mg of *Sambucus nigra*, or a salt or solvate thereof.

In some embodiments, the compositions useful for preventing HSV infection in seronegative subjects comprising valacyclovir, or a salt or solvate thereof, further comprise pritelivir. In some embodiments, the methods for preventing HSV infection in seronegative subjects comprising administering to the subject valacyclovir, or a salt or solvate thereof, further comprise administering to the subject pritelivir, or a salt or solvate thereof. In some embodiments, the methods comprise administering to the HSV seronegative subject at least or about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of pritelivir, or a salt or solvate thereof. In some cases, pritelivir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 5 mg to about 75 mg of pritelivir, or a salt or solvate thereof.

In some embodiments, the compositions useful for preventing HSV infection in seronegative subjects comprising valacyclovir, or a salt or solvate thereof, further comprise pritelivir and emtricitabine. In some embodiments, the methods for preventing HSV infection in seronegative subjects comprising administering to the subject valacyclovir, or a salt or solvate thereof, further comprise administering to the subject pritelivir, or a salt or solvate thereof and emtricitabine, or a salt or solvate thereof. In some embodiments, the methods comprise administering to the HSV seronegative subject at least or about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of pritelivir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some cases, pritelivir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, from about 5 mg to about 75 mg of pritelivir, or a salt or solvate thereof, and from about 100 mg to about 300 mg of emtricitabine, or a salt or solvate thereof.

In some embodiments, the compositions useful for preventing HSV infection in seronegative subjects comprising valacyclovir, or a salt or solvate thereof, further comprise pritelivir and lamivudine. In some embodiments, the methods for preventing HSV infection in seronegative subjects comprising administering to the subject valacyclovir, or a salt or solvate thereof, further comprise administering to the subject pritelivir, or a salt or solvate thereof and lamivudine, or a salt or solvate thereof. In some embodiments, the methods comprise administering to the HSV seronegative subject at least or about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of pritelivir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some cases, pritelivir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, from about 5 mg to about 75 mg of pritelivir, or a salt or solvate thereof, and from about 100 mg to about 300 mg of lamivudine, or a salt or solvate thereof.

In some embodiments, the compositions useful for preventing pregnancy and HSV infection in seronegative subjects comprising valacyclovir, or a salt or solvate thereof, further comprise emtricitabine and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of emtricitabine, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise lamivudine and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of lamivudine, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject glycyrrhizic acid, or a salt or solvate thereof and one or more contraceptive agents. In some cases, the contraceptive agents comprise levonorgestrel and ethinyl estradiol. In some embodiments, the methods comprise administering to the HSV seronegative subject at least or about 1 mg, 2 mg, 3 mg, 4 mg, 5 mg, 6 mg, 7 mg, or 8 mg, 9 mg, 10 mg, 11 mg, 12 mg, 13 mg, 14 mg, 15 mg, 20 mg of glycyrrhizic acid, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 1 mg to about 10 mg of glycyrrhizic acid, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject *Sambucus nigra*, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of *Sambucus nigra*, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 200 mg of *Sambucus nigra*, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise emtricitabine, tenofovir and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; tenofovir, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of emtricitabine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise lamivudine, tenofovir and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof tenofovir, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of lamivudine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise glycyrrhizic acid, tenofovir, emtricitabine and one or more contraceptive agents. In some embodiments, the methods for preventing pregnancy and HSV infection in seronegative subjects comprising administering to the subject valacyclovir, or a salt or solvate thereof, further comprise administering to the subject glycyrrhizic acid, or a salt or solvate thereof; emtricitabine, or a salt or solvate thereof; tenofovir, or a salt or solvate thereof; and one or more contraceptive agents. In some cases, the contraceptive agents comprise levonorgestrel and ethinyl estradiol. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 1 mg to about 10 mg of glycyrrhizic acid, or a salt or solvate thereof, once daily; c) administering to the subject from about 100 mg to about 300 mg of emtricitabine, or a salt or solvate thereof, once daily; d) administering to the subject from about 100 mg to about 400 mg of tenofovir, or a salt or solvate thereof, once daily; and e) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise *Sambucus nigra*, tenofovir, emtricitabine and one or more contraceptive agents. In some embodiments, the methods for preventing pregnancy and HSV infection in seronegative subjects comprising administering to the subject valacyclovir, or a salt or solvate thereof, further comprise administering to the subject *Sambucus nigra*, or a salt or solvate thereof; emtricitabine, or a salt or solvate thereof; tenofovir, or a salt or solvate thereof; and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, or 300 mg of *Sambucus nigra*, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 50 mg to about 200 mg of *Sambucus nigra*, or a salt or solvate thereof, once daily; c) administering to the subject from about 100 mg to about 300 mg of emtricitabine, or a salt or solvate thereof, once daily; d) administering to the subject from about 100 mg to about 400 mg of tenofovir, or a salt or solvate thereof, once daily; and e) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of emtricitabine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, lamivudine and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of lamivudine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; glycyrrhizic acid, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 1 mg to about 10 mg of glycyrrhizic acid, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; *Sambucus nigra*, or a salt or solvate thereof tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 50 mg, 100 mg, 150 mg, 200 mg, 250 mg, or 300 mg *Sambucus nigra* or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 50 mg to about 200 mg of *Sambucus nigra*, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, efavirenz and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; efavirenz, or a salt or solvate thereof tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, lamivudine, efavirenz and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof efavirenz, or a salt or solvate thereof tenofovir, or a salt or solvate thereof and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of lamivudine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, efavirenz, glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; efavirenz, or a salt or solvate thereof; tenofovir, or a salt or solvate thereof; glycyrrhizic acid, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 1 mg to about 10 mg of glycyrrhizic acid, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, efavirenz, *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; efavirenz, or a salt or solvate thereof; tenofovir, or a salt or solvate thereof; *Sambucus nigra*, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of *Sambucus nigra*, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 50 mg to about 300 mg of *Sambucus nigra*, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, dolutegravir and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; dolutegravir, or a salt or solvate thereof tenofovir, or a salt or solvate thereof and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 20 mg, 30 mg, 40 mg, 50 mg, 60 mg, 70 mg, 80 mg, 90 mg or 100 mg of dolutegravir or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, lamivudine, dolutegravir and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof; dolutegravir, or a salt or solvate thereof tenofovir, or a salt or solvate thereof and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 20 mg, 30 mg, 40 mg, 50 mg, 60 mg, 70 mg, 80 mg, 90 mg or 100 mg of dolutegravir or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of lamivudine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, dolutegravir, glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; dolutegravir, or a salt or solvate thereof; tenofovir, or a salt or solvate thereof; glycyrrhizic acid, or a salt or solvate thereof and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 10 mg, 20 mg, 30 mg, 40 mg, 50 mg, 60 mg, 70 mg, 80 mg, 90 mg, or 100 mg of dolutegravir or a salt or solvate thereof. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 1 mg to about 10 mg of glycyrrhizic acid, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, dolutegravir, *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; dolutegravir, or a salt or solvate thereof; tenofovir, or a salt or solvate thereof; *Sambucus nigra*, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 10 mg, 20 mg, 30 mg, 40 mg, 50 mg, 60 mg, 70 mg, 80 mg, 90 mg, or 100 mg of dolutegravir or a salt or solvate thereof. In some embodiments, the methods comprise administering to the HSV seronegative subject at least or about 50 mg, 100 mg, 10 mg, 200 mg, 250 mg, or 300 mg of *Sambucus nigra*, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 50 mg to about 200 mg of *Sambucus nigra*, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

Non-Limiting Antiviral Compositions for Preventing HSV Infection

In some embodiments, provided herein are methods of preventing HSV infection in an HSV seronegative subject comprising administering to the subject from about 200 mg to about 2,500 mg of valacyclovir, or a salt or solvate thereof, once per day. In some cases, valacyclovir is administered prior to exposure to HSV. In some cases, valacyclovir is administered after exposure to HSV. In some cases, valacyclovir is administered both prior to and after exposure to HSV. In some cases, valacyclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, or 2500 mg of valacyclovir, or a salt or solvate thereof, once per day. In some cases, the methods comprise administering to the HSV seronegative subject from about 400 mg to about 2000 mg, from about 400 mg to about 1000 mg, or from about 1000 mg to about 2000 mg valacyclovir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 200 mg to about 2,000 mg of acyclovir, or a salt or solvate thereof, twice per day. In some cases, acyclovir is administered prior to exposure to HSV. In some cases, acyclovir is administered after exposure to HSV. In some cases, acyclovir is administered both prior to and after exposure to HSV. In some cases, acyclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 400 mg, 500 mg, 600 mg, 700 mg, 800 mg, 900 mg, 1000 mg, 1100 mg, 1200 mg, 1300 mg, 1400 mg, 1500 mg, or 1600 mg of acyclovir, or a salt or solvate thereof, twice per day. In some cases, the methods comprise administering to the HSV seronegative subject from about 400 mg to about 800 mg, from about 800 mg to about 1000 mg, or from about 1000 mg to about 1600 mg of acyclovir, or a salt or solvate thereof, twice per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 5 mg to about 80 mg of pritelivir, or a salt or solvate thereof, once per day. In some cases, pritelivir is administered prior to exposure to HSV. In some cases, pritelivir is administered after exposure to HSV. In some cases, pritelivir is administered both prior to and after exposure to HSV. In some cases, pritelivir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 5 mg, 10 mg, 20 mg, 30 mg, 40 mg, 50 mg, 60 mg, 70 mg, or 80 mg of pritelivir, or a salt or solvate thereof, once per day. In some cases, the methods comprise administering to the HSV seronegative subject from about 5 mg to about 20 mg, from about 20 mg to about 50 mg, or from about 50 mg to about 80 mg of pritelivir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 200 mg to about 500 mg of famciclovir, or a salt or solvate thereof, twice per day. In some cases, famciclovir is administered prior to exposure to HSV. In some cases, famciclovir is administered after exposure to HSV. In some cases, famciclovir is administered both prior to and after exposure to HSV. In some cases, famciclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 200 mg, 225 mg, 250 mg, 275 mg, 300 mg, 350 mg, 400 mg, 450 mg, or 500 mg of famciclovir, or a salt or solvate thereof, twice per day. In some cases, the methods comprise administering to the HSV seronegative subject from about 225 mg to about 300 mg, from about 300 mg to about 400 mg, or from about 400 mg to about 500 mg of famciclovir, or a salt or solvate thereof, twice per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one or more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one or more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one or more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 200 mg to about 400 mg of tenofovir, or a salt or solvate thereof, once per day. In some cases, tenofovir is administered prior to exposure to HSV. In some cases, tenofovir is administered after exposure to HSV. In some cases, tenofovir is administered both prior to and after exposure to HSV. In some cases, tenofovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 200 mg, 225 mg, 250 mg, 275 mg, 300 mg, 325 mg, 350 mg, 375 mg, or 400 mg of tenofovir, or a salt or solvate thereof, once per day. In some cases, the methods comprise administering to the HSV seronegative subject from about 200 mg to about 250 mg, from about 250 mg to about 350 mg, or from about 350 mg to about 400 mg of tenofovir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one or more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one or more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one or more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 500 mg to about 1500 mg of ganciclovir, or a salt or solvate thereof, three times per day. In some cases, ganciclovir is administered prior to exposure to HSV. In some cases, ganciclovir is administered after exposure to HSV. In some cases, ganciclovir is administered both prior to and after exposure to HSV. In some cases, ganciclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 500 mg, 600 mg, 700 mg, 800 mg, 900 mg, 1000 mg, 1100 mg, 1200 mg, 1300 mg, 1400 mg, or 1500 mg of ganciclovir, or a salt or solvate thereof, three times per day. In some cases, the methods comprise administering to the HSV seronegative subject from about 500 mg to about 800 mg, from about 800 mg to about 1200 mg, or from about 1200 mg to about 1500 mg of ganciclovir, or a salt or solvate thereof, three times per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one or more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 1 mg to about 20 mg of glycyrrhizic acid, or a salt or solvate thereof, once per day. In some cases, glycyrrhizic acid is administered prior to exposure to HSV. In some cases, glycyrrhizic acid is administered after exposure to HSV. In some cases, glycyrrhizic acid is administered both prior to and after exposure to HSV. In some cases, glycyrrhizic acid is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg of glycyrrhizic acid, or a salt or solvate thereof, once per day. In some cases, the methods comprise administering to the HSV seronegative subject from about 1 mg to about 5 mg, from about 5 mg to about 10 mg, or from about 10 mg to about 15 mg of glycyrrhizic acid, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 50 mg to about 400 mg of *Sambucus nigra*, or a salt or solvate thereof, once per day. In some cases, *Sambucus nigra* is administered prior to exposure to HSV. In some cases, *Sambucus nigra* is administered after exposure to HSV. In some cases, *Sambucus nigra* is administered both prior to and after exposure to HSV. In some cases, *Sambucus nigra* is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 50 mg, 75 mg, 100 mg, 125 mg, 150 mg, 175 mg, 200 mg, 225 mg, 250 mg, 275 mg, 300 mg, 325 mg, 350 mg, 375 mg, or 400 mg of *Sambucus nigra*, or a salt or solvate thereof, once per day. In some cases, the methods comprise administering to the HSV seronegative subject from about 50 mg to about 100 mg, from about 100 mg to about 250 mg, or from about 250 mg to about 400 mg of *Sambucus nigra*, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 500 mg to about 1500 mg of valganciclovir, or a salt or solvate thereof, once per day. In some cases, valganciclovir is administered prior to exposure to HSV. In some cases, valganciclovir is administered after exposure to HSV. In some cases, valganciclovir is administered both prior to and after exposure to HSV. In some cases, valganciclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 500 mg, 600 mg, 700 mg, 800 mg, 900 mg, 1000 mg, 1100 mg, 1200 mg, 1300 mg, 1400 mg, or 1500 mg of valganciclovir, or a salt or solvate thereof, once per day. In some cases, the methods comprise administering to the HSV seronegative subject from about 500 mg to about 800 mg, from about 800 mg to about 1200 mg, or from about 1200 mg to about 1500 mg of valganciclovir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

Pre-Exposure Compositions and Methods

In some aspects, described herein are compositions for administration to an HSV seronegative subject, the compositions comprising a low dose of a first antiviral agent; wherein the composition is administered to the subject prior to physical contact with a partner who is either infected with HSV or has unknown HSV status. In some embodiments, the composition is a pre-exposure composition. In some embodiments, the first antiviral agent is an HSV antiviral agent. In some embodiments, the first antiviral agent comprises valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition and/or antiviral agent is useful for the prevention of HSV infection in the seronegative subject when the composition and/or antiviral agent is administered to the subject at least prior to exposure to HSV. In some cases, the composition and/or first antiviral agent is useful for the prevention of HSV infection in the seronegative subject when the composition and/or antiviral agent is administered to the subject prior to and after exposure to HSV. In some embodiments, the composition and/or antiviral agent is useful to suppress HSV replication in the subject when the composition and/or antiviral agent is administered to the subject prior to exposure to HSV. In some cases, the composition and/or antiviral agent is useful to suppress HSV replication in the subject when the composition and/or antiviral agent is administered to the subject prior to and after exposure to HSV. In some embodiments, the composition and/or antiviral agent is useful to suppress HSV activation in the subject when the composition and/or antiviral agent is administered to the subject prior to exposure to HSV. In some cases, the composition and/or antiviral agent is useful to suppress HSV activation in the subject when the composition and/or antiviral agent is administered to the subject prior to and after exposure to HSV.

In some embodiments, the composition is useful to reduce the risk of HSV infection in the subject when the composition is administered to the subject prior to exposure to HSV. In some embodiments, the risk of HSV infection is reduced by at least about 10%, 20%, 30%, 40%, 50%, 60%, 70%, 80%, 90%, or 100%, as compared to the risk of HSV infection without administration of the composition.

In some embodiments, the low dose of the first antiviral agent is from about 50 mg to about 1 g. In some embodiments, the low dose of the first antiviral agent is less than about 1,000 mg, less than about 900 mg, less than about 800 mg, less than about 700 mg, less than about 600 mg, less than about 500 mg, less than about 480 mg, less than about 460 mg, less than about 440 mg, less than about 420 mg, less than about 400 mg, less than about 380 mg, less than about 360 mg, less than about 340 mg, less than about 320 mg, less than about 300 mg, less than about 280 mg, less than about 260 mg, less than about 240 mg, less than about 220 mg, less than about 200 mg, less than about 180 mg, less than about 160 mg, less than about 140 mg, less than about 120 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 5 mg, or less than about 1 mg. In some cases, the low dose of the first antiviral agent is between about 50 mg and about 500 mg, between about 50 mg and about 480 mg, between about 50 mg and about 460 mg, between about 50 mg and about 440 mg, between about 50 mg and about 420 mg, between about 50 mg and about 400 mg, between about 50 mg and about 380 mg, between about 50 mg and about 360 mg, between about 50 mg and about 340 mg, between about 50 mg and about 320 mg, between about 50 mg and about 300 mg, between about 50 mg and about 280 mg, between about 50 mg and about 260 mg, between about 50 mg and about 240 mg, between about 50 mg and about 220 mg, or between about 50 mg and about 200 mg. In some embodiments, the low dose of the first antiviral agent is an amount similar to an amount of the first antiviral agent useful for suppression treatment in an HSV seropositive subject. In some embodiments, the low dose of the first antiviral agent is configured for administration to the subject between about once per 5 years to about twice daily. For example, the antiviral is administered every year, 6 months, 5 months, 4 months, 3 months, 2 months, 1 month, 3 weeks, 2 weeks, 1 week, twice a week, daily, or twice daily. In some embodiments, the composition is administered to the subject at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, or 3 months prior to HSV exposure (time points are not limited to whether it is the first HSV exposure or any subsequent HSV exposure).

In some embodiments, the first antiviral agent is formulated for administration by a long-acting drug delivery mechanism using a long-acting drug delivery device. In some embodiments, the long-acting delivery device is an intravaginal ring. In some embodiments, the long-acting delivery device is a transdermal patch. In some embodiments, the long-acting delivery device is an injection device.

In some embodiments, the composition further comprises a second, third, fourth, or fifth antiviral agent. In alternative or additional embodiments, the composition is configured for administration with a second, third, fourth, or fifth antiviral agent. In some embodiments, the second, third, fourth, and/or fifth antiviral agent is present in the composition at a second lose dose. In some cases, the second, third, fourth, and/or fifth antiviral agent comprises the same or different active agent as the first antiviral agent. In some embodiments, the second, third, fourth, and/or fifth antiviral agent comprises valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-ASO4, Havrix™ gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, Ibalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (–)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-di chlorophenyl)thio]-4-isopropyl-1-(4-pyridylmethyl)imidazole-2-methanol carbamic acid, (–)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *Sambucus*, umifenovir, amantadine, rimantadine, oseltamivir, zanamivir, peramivir, laninamivir, pyrrole polyamides, lopinavir, or salts, solvates, and/or combinations thereof.

In some embodiments, the second, third, fourth, and/or fifth antiviral agent is an HIV antiviral comprising maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (–)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (–)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof.

In some embodiments, the second, third, fourth, and/or fifth low dose of a second, third, fourth, and/or fifth antiviral agent is from about 50 mg to about 1 g. In some embodiments, the low dose of the second, third, fourth, and/or fifth antiviral agent is less than about 1,000 mg, less than about 900 mg, less than about 800 mg, less than about 700 mg, less than about 600 mg, less than about 500 mg, less than about 480 mg, less than about 460 mg, less than about 440 mg, less than about 420 mg, less than about 400 mg, less than about 380 mg, less than about 360 mg, less than about 340 mg, less than about 320 mg, less than about 300 mg, less than about 280 mg, less than about 260 mg, less than about 240 mg, less than about 220 mg, less than about 200 mg, less than about 180 mg, less than about 160 mg, less than about 140 mg, less than about 120 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 5 mg, or less than about 1 mg. In some cases, the low dose of the second, third, fourth, and/or fifth antiviral agent is between about 50 mg and about 500 mg, between about 50 mg and about 480 mg, between about 50 mg and about 460 mg, between about 50 mg and about 440 mg, between about 50 mg and about 420 mg, between about 50 mg and about 400 mg, between about 50 mg and about 380 mg, between about 50 mg and about 360 mg, between about 50 mg and about 340 mg, between about 50 mg and about 320 mg, between about 50 mg and about 300 mg, between about 50 mg and about 280 mg, between about 50 mg and about 260 mg, between about 50 mg and about 240 mg, between about 50 mg and about 220 mg, or between about 50 mg and about 200 mg.

In various embodiments, the compositions described herein further comprise or are administered with one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof.

In some aspects, described herein are methods for preventing HSV infection in an HSV seronegative subject, the methods comprising the administration of a composition comprising a low dose of a first antiviral agent to the subject prior to physical contact (e.g., sexual contact) with a partner who is either infected with HSV or has unknown HSV status. In some embodiments, the physical contact occurs during one sexual incident. In some embodiments, the physical contact occurs during two or more sexual incidents. In some embodiments, the physical contact occurs with a single partner. In some embodiments, the physical contact occurs with two or more partners. In various instances, the subject has a risk of exposure to HSV during physical contact with the partner. In some methods, the subject is exposed to HSV. In some embodiments, the methods further comprise administration of the composition after exposure to HSV. In some embodiments, the composition is a pre-exposure composition as described above.

In some embodiments, the subject is at risk for exposure to HSV because the subject is or will be in an ongoing sexual relationship with a partner who is seropositive for HSV. In some embodiments, the seropositive partner is undergoing HSV suppression therapy. In some cases, the HSV suppression therapy comprises the administration of a low dose of an additional antiviral agent to the partner. In some cases, this additional antiviral agent comprises a same active agent as the first antiviral agent. In some cases, the additional antiviral agent comprises a different active agent as the first antiviral agent. In some cases, the subject and the seropositive partner use a physical barrier such as a condom during sexual contact. In some instances, the subject is exposed to HSV from the seropositive partner. In such instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In some embodiments, the subject is at risk for exposure to HSV because the subject is not or will not be in a mutually-monogamous sexual relationship. In some instances, the subject is exposed to HSV during sexual contact within the non-mutual monogamous sexual relationship. In such instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition.

In some embodiments, the subject is at risk for exposure to HSV because the subject has or will have physical contact with a partner of unknown HSV status. In some cases, the partner of unknown HSV status is undergoing HSV treatment comprising the administration of a low dose of an additional antiviral agent to the partner, as described above. In some cases, the additional antiviral agent comprises a same active agent as the first antiviral agent. In some cases, the additional antiviral agent comprises a different active agent than the first antiviral agent. In some cases, the physical contact is sexual contact. In some instances, the subject and the partner of unknown HSV status use physical barrier, such as a condom during sexual contact. In some instances, the physical contact is kissing.

In some embodiments, the subject is at risk for exposure to HSV because the subject has or will have physical contact with an HSV seropositive partner. In some cases, the partner is undergoing HSV treatment comprising the administration of a low dose of an additional antiviral agent to the partner, as described above. In some cases, the additional antiviral agent comprises a same active agent as the first antiviral agent. In some cases, the additional antiviral agent comprises a different active agent than the first antiviral agent. In some cases, the physical contact is sexual contact. In some instances, the subject and the partner of unknown HSV status use physical barrier, such as a condom during sexual contact. In some instances, the subject is exposed to HSV from the partner known to have HSV. In such instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In various embodiments, the composition administered to the subject further comprises one or more contraceptive agents. In some embodiments, the methods further comprise administering to the subject one or more contraceptive agents. In some embodiments, the contraceptive agent comprises 17a-ethinyl-levonorgestrel-17b-hydroxy-estra-4,9,11- trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9, 11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof. In some embodiments, the contraceptive agent comprises a condom, cervical cap, female condom, diaphragm, intrauterine device, spermicide (e.g., nonoxynol, octoxynol), or other contraceptives known in the art.

In some embodiments, the compositions are used in conjunction with condoms, to enhance the risk-reducing effectiveness of condoms and provide maximum protection. In some cases, the composition is coated onto condoms during manufacture, and enclosed within conventional watertight plastic or foil packages that contain one condom per package, or it can be manually applied by a user to either the inside or the outside of a condom, immediately before use.

In some embodiments, the methods further comprise determining if the subject is in a risk category for exposure to HSV. In some embodiments, the methods further comprise determining the low dose of the composition for administration to the subject. In some instances, provided that the subject is in a risk category for exposure to HSV, the method further comprises using the risk category to determine the low dose of the composition for administration to the subject. In some embodiments, the methods further comprise determining the identity of the first antiviral agent. In some instances, provided that the subject is in a risk category for exposure to HSV, the method further comprises using the risk category to determine the identity of the first antiviral agent. In some instances, the methods further comprise determining a delivery device for the administration of the composition to the subject. In some cases, the delivery device is a long-acting delivery device. In some cases, the long-acting delivery device is an intravaginal ring. In some cases, the long-acting delivery device is an injection device. In some instances, the long-acting delivery device is a transdermal patch.

An exemplary method of delivery of an antiviral composition described herein for the prevention of HSV infection in a seronegative subject is through a sustained release system via an intravaginal ring. In some embodiments, the intravaginal ring comprises a silicone elastomer. In some embodiments, the intravaginal ring comprises ethylene vinyl acetate. In some embodiments, the intravaginal ring is latex free. In some embodiments, the intravaginal ring comprises polyurethane. In some cases, the polyurethane is a polyesterurethane. In some cases, the intravaginal ring is biodegradable. In some embodiments, the intravaginal ring further comprises one or more active agents as a contraceptive. In some cases, the contraceptive agent is an estrogenic compound, a progestational compound, and/or a gonadotropin releasing hormone or its peptide or non-peptide agonists or antagonist analogues. In some embodiments, the method comprises inserting delivery device intravaginally and maintaining the device intravaginally for about 1 to about 180 days. In some embodiments, the delivery device is an intravaginal ring and the release rate of the antiviral agent is from about 1 ug/day to about 10 mg/day. In some cases, the intravaginal ring further comprises a contraceptive agent and the contraceptive agent is released from the ring from about 1 ug/day to about 10 mg/day.

Post-Exposure Compositions and Methods

In some aspects, described herein are compositions for administration to an HSV seronegative subject, the compositions comprising a very dose of a first antiviral agent; wherein the composition is administered to the subject after exposure to HSV. In some embodiments, the composition is a post-exposure composition. In some embodiments, the first antiviral agent is an HSV antiviral agent. In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, amenamevir, N-methancocarbathymidine (N-MCT), or salts, solvates, or combinations thereof. In some embodiments, the composition and/or first antiviral agent is useful for the prevention of HSV infection in the seronegative subject when the composition and/or first antiviral agent is administered to the subject after exposure to HSV. In some cases, the composition and/or first viral agent is useful for the prevention of HSV infection in the seronegative subject when the composition and/or first viral agent is administered to the subject prior to and after exposure to HSV. In some embodiments, the composition and/or antiviral agent is useful to suppress HSV replication in the subject when the composition and/or antiviral agent is administered to the subject after exposure to HSV. In some cases, the composition and/or antiviral agent is useful to suppress HSV replication in the subject when the composition and/or antiviral agent is administered to the subject prior to and after exposure to HSV. In some embodiments, the composition and/or antiviral agent is useful to suppress HSV activation in the subject when the composition and/or antiviral agent is administered to the subject after exposure to HSV. In some cases, the composition and/or antiviral agent is useful to suppress HSV activation in the subject when the composition is administered to the subject prior to and after exposure to HSV. In some cases, the composition and/or antiviral agent is useful to suppress HSV re-activation in the subject when the composition is administered to a seropositive subject. In some cases, the composition and/or antiviral agent is useful to treat HSV infection in the subject when the composition is administered to a seropositive subject.

In some embodiments, the composition is useful to reduce the risk of HSV infection in the subject when the composition is administered to the subject after exposure to HSV. In some embodiments, the risk of HSV infection is reduced by at least about 10%, 20%, 30%, 40%, 50%, 60%, 70%, 80%, 90%, or 100%, as compared to the risk of HSV infection without administration of the composition.

In some embodiments, the very high dose of the first antiviral agent is from about 500 mg to about 5,000 mg. In some embodiments, the very high dose of the first antiviral agent is greater than about 500 mg, greater than about 600 mg, greater than about 700 mg, greater than about 800 mg, greater than about 900 mg, greater than about 1,000 mg, greater than about 1,100 mg, greater than about 1,200 mg, greater than about 1,300 mg, greater than about 1,400 mg, greater than about 1,500 mg, greater than about 1,600 mg, greater than about 1,700 mg, greater than about 1,800 mg, greater than about 1,900 mg, greater than about 2,000 mg, greater than about 2,100 mg, greater than about 2,200 mg, greater than about 2,300 mg, greater than about 2,400 mg, greater than about 2,500 mg, greater than about 2,600 mg, greater than about 2,700 mg, greater than about 2,800 mg, greater than about 2,900 mg, greater than about 3,000 mg, greater than about 3,500 mg, greater than about 4,000 mg, greater than about 4,500 mg, or greater than about 5,000 mg. In some cases, the very high dose of the first antiviral agent is between about 500 mg and about 5,000 mg, between about 600 mg and about 5,000 mg, between about 700 mg and about 5,000 mg, between about 800 mg and about 5,000 mg, between about 900 mg and about 5,000 mg, between about 1,000 mg and about 5,000 mg, between about 1,200 mg and about 5,000 mg, between about 1,400 mg and about 5,000 mg, between about 1,600 mg and about 5,000 mg, between about 1,800 mg and about 5,000 mg, between about 2,000 mg and about 5,000 mg, between about 2,200 mg and about 5,000 mg, between about 2,400 mg and about 5,000 mg, between about 2,600 mg and about 5,000 mg, between about 2,800 mg and about 5,000 mg, between about 3,000 mg and about 5,000 mg, or between about 3,200 mg and about 5,000 mg. In some embodiments, the very high dose of the first antiviral agent is an amount greater than an amount of the first antiviral agent useful for treatment of an outbreak in an HSV seropositive subject. In some embodiments, the very high dose of the first antiviral agent is configured for administration to the subject within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 1 day, 36 hours, 2 days, 60 hours, 3 days, 4 days, 5 days, 6 days, 1 week, 2 weeks, 1 month, or 2 months of HSV exposure. In some embodiments, the very high dose is administered once a month, once every 3 weeks, once every 2 weeks, once every week, 6 times a week, 5 times a week, 4 times a week, 3 times a week, 2 times a week, 3 times per day, 2 times per day or once per day.

In some embodiments, the first antiviral agent is formulated for administration by a long-acting drug delivery mechanism using a long-acting drug delivery device. In some embodiments, the long-acting delivery device is an intravaginal ring. In some embodiments, the long-acting delivery device is a transdermal patch. In some embodiments, the long-acting delivery device is an injection device.

In some embodiments, the composition further comprises a second, third, fourth, or fifth antiviral agent. In alternative or additional embodiments, the composition is configured for administration with a second, third, fourth, and/or fifth antiviral agent. In some embodiments, the second, third, fourth, and/or fifth antiviral agent is present in the composition at a second, third, fourth, and/or fifth very high dose. In some cases, the second, third, fourth, and/or fifth antiviral agent comprises the same or different active agent as the first antiviral agent. In some embodiments, the second, third, fourth, and/or fifth antiviral agent comprises valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-ASO4, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™) GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-12-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *Sambucus*, umifenovir, amantadine, rimantadine, oseltamivir, zanamivir, peramivir, laninamivir, pyrrole polyamides, lopinavir, amenamevir, N-methancocarbathymidine (N-MCT), or salts, solvates, and/or combinations thereof.

In some embodiments, the second, third, fourth, and/or fifth antiviral agent is an HIV antiviral comprising maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-di chlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,4-dihydro-4-trifluoromethyl-2(1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof.

In some embodiments, the second, third, fourth, and/or fifth very high dose of a second antiviral agent is from about 500 mg to about 5,000 mg. In some embodiments, the very high dose of the second, third, fourth, and/or fifth antiviral agent is greater than about 500 mg, greater than about 600 mg, greater than about 700 mg, greater than about 800 mg, greater than about 900 mg, greater than about 1,000 mg, greater than about 1,100 mg, greater than about 1,200 mg, greater than about 1,300 mg, greater than about 1,400 mg, greater than about 1,500 mg, greater than about 1,600 mg, greater than about 1,700 mg, greater than about 1,800 mg, greater than about 1,900 mg, greater than about 2,000 mg, greater than about 2,100 mg, greater than about 2,200 mg, greater than about 2,300 mg, greater than about 2,400 mg, greater than about 2,500 mg, greater than about 2,600 mg, greater than about 2,700 mg, greater than about 2,800 mg, greater than about 2,900 mg, greater than about 3,000 mg, greater than about 3,500 mg, greater than about 4,000 mg, greater than about 4,500 mg, or greater than about 5,000 mg. In some cases, the very high dose of the second, third, fourth, and/or fifth antiviral agent is between about 500 mg and about 5,000 mg, between about 600 mg and about 5,000 mg, between about 700 mg and about 5,000 mg, between about 800 mg and about 5,000 mg, between about 900 mg and about 5,000 mg, between about 1,000 mg and about 5,000 mg, between about 1,200 mg and about 5,000 mg, between about 1,400 mg and about 5,000 mg, between about 1,600 mg and about 5,000 mg, between about 1,800 mg and about 5,000 mg, between about 2,000 mg and about 5,000 mg, between about 2,200 mg and about 5,000 mg, between about 2,400 mg and about 5,000 mg, between about 2,600 mg and about 5,000 mg, between about 2,800 mg and about 5,000 mg, between about 3,000 mg and about 5,000 mg, or between about 3,200 mg and about 5,000 mg. In some embodiments, the very high dose of the second, third, fourth, and/or fifth antiviral agent is an amount greater than an amount of the first antiviral agent useful for treatment of an outbreak in an HSV seropositive subject. In some embodiments, the very high dose of the second, third, fourth, and/or fifth antiviral agent is configured for administration to the subject within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 1 day, 36 hours, 2 days, 60 hours, 3 days, 4 days, 5 days, 6 days, 1 week, 2 weeks or 1 month of HSV exposure. In some embodiments, the very high dose is administered once a month, once every 3 weeks, once every 2 weeks, once every week, 6 times a week, 5 times a week, 4 times a week, 3 times a week, 2 times a week, 3 times per day, 2 times per day or once per day.

In various embodiments, the compositions described herein further comprise or are administered with one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof.

In some aspects, described herein are methods for preventing HSV infection in an HSV seronegative subject, the methods comprising the administration of a composition comprising a very high dose of a first antiviral agent to the subject after the subject is exposed to HSV. In some embodiments, the HSV exposure occurs during one sexual incident between the HSV seronegative subject and an HSV seropositive partner. In some embodiments, HSV exposure occurs during two or more sexual incidents. In some embodiments, HSV exposure is from a single partner. In some embodiments, HSC exposure occurs from two or more partners. In some embodiments, the composition is a post-exposure composition as described above. In some embodiments, the methods further comprise administering to the subject a pre-exposure composition as previously described.

In some embodiments, the subject is exposed to HSV from physical contact (e.g., sexual contact or kissing) with a partner who is seropositive for HSV, wherein the subject and the partner are in a mutually monogamous relationship. In some instances, the partner is aware of their seropositive status. In some instances, the partner is not aware of their seropositive status. In some cases, the subject is aware the HSV seropositive status of the partner. In some cases, the subject is not aware of the HSV seropositive status of the partner. In some embodiments, the seropositive partner is undergoing HSV suppression therapy. In some cases, the HSV suppression therapy comprises the administration of a low dose of an additional antiviral agent to the partner. In some cases, this additional antiviral agent comprises a same active agent as the first antiviral agent. In some cases, the additional antiviral agent comprises a different active agent as the first antiviral agent. In some cases, the subject and the seropositive partner use a physical barrier such as a condom during sexual contact. In some instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In some embodiments, the subject is exposed to HSV from physical contact (e.g., sexual contact) with an HSV seropositive partner, wherein the subject and the partner are not in a mutually monogamous relationship. In some instances, the partner is aware of their seropositive status. In some instances, the partner is not aware of their seropositive status. In some cases, the subject is aware the HSV seropositive status of the partner. In some cases, the subject is not aware of the HSV seropositive status of the partner. In some embodiments, the seropositive partner is undergoing HSV suppression therapy. In some cases, the HSV suppression therapy comprises the administration of a low dose of an additional antiviral agent to the partner. In some cases, this additional antiviral agent comprises a same active agent as the first antiviral agent. In some cases, the additional antiviral agent comprises a different active agent as the first antiviral agent. In some cases, the subject and the seropositive partner use a physical barrier such as a condom during sexual contact. In some instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In various embodiments, the composition administered to the subject further comprises one or more contraceptive agents. In some embodiments, the methods further comprise administering to the subject one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof. In some embodiments, the contraceptive agent comprises a condom, cervical cap, female condom, diaphragm, intrauterine device, spermicide (e.g., nonoxynol, octoxynol), or other contraceptives known in the art. In some embodiments, the contraceptive is an emergency contraceptive. Non-limiting examples of emergency contraceptive agents include levonorgestrel, combinations of estrogen and progestin, progestin, antiprogestin (e.g., ulipristal acetate, mifepristone), and salts, solvates or combinations thereof.

In some embodiments, the compositions are used in conjunction with condoms, to enhance the risk-reducing effectiveness of condoms and provide maximum protection. In some cases, the composition is coated onto condoms during manufacture, and enclosed within conventional watertight plastic or foil packages that contain one condom per package, or it can be manually applied by a user to either the inside or the outside of a condom, immediately before use.

In some embodiments, the methods further comprise determining the very high dose of the composition for administration to the subject. In some embodiments, the methods further comprise determining the identity of the first antiviral agent. In some instances, the methods further comprise determining a delivery device for the administration of the composition to the subject. In some cases, the delivery device is a long-acting delivery device. In some cases, the long-acting delivery device is an intravaginal ring. In some cases, the long-acting delivery device is an injection device. In some instances, the long-acting delivery device is a transdermal patch.

An exemplary method of delivery of an antiviral composition described herein for the prevention of HSV infection in a seronegative subject is through a sustained release system via an intravaginal ring. In some embodiments, the intravaginal ring comprises a silicone elastomer. In some embodiments, the intravaginal ring comprises ethylene vinyl acetate. In some embodiments, the intravaginal ring is latex free. In some embodiments, the intravaginal ring comprises polyurethane. In some cases, the polyurethane is a polyesterurethane. In some cases, the intravaginal ring is biodegradable. In some embodiments, the intravaginal ring further comprises one or more active agents as a contraceptive. In some cases, the contraceptive agent is an estrogenic compound, a progestational compound, and/or a gonadotropin releasing hormone or its peptide or non-peptide agonists or antagonist analogues. In some embodiments, the method comprises inserting delivery device intravaginally and maintaining the device intravaginally for about 1 to about 180 days. In some embodiments, the delivery device is an intravaginal ring and the release rate of the antiviral agent is from about 1 ug/day to about 10 mg/day. In some cases, the intravaginal ring further comprises a contraceptive agent and the contraceptive agent is released from the ring from about 1 ug/day to about 10 mg/day.

Pharmaceutical Compositions and Formulations

Provided herein, in various aspects, are compositions comprising one or more active agents, for example, antiviral agents and contraceptive agents, formulated with one or more pharmaceutically acceptable excipients, diluents, carriers and/or adjuvants. In addition, compositions of the disclosure include active agents formulated with one or more pharmaceutically acceptable auxiliary substances. Auxiliary substances, such as pH adjusting and buffering agents, tonicity adjusting agents, stabilizers, wetting agents and the like are readily available to the public. Suitable excipient vehicles for a composition include, for example, water, saline, dextrose, glycerol, ethanol and/or combinations thereof. In addition, the vehicle may comprise auxiliary substances such as wetting or emulsifying agents or pH buffering agents.

In many embodiments, the active agent is formulated into a pharmaceutical composition by combination with appropriate, pharmaceutically acceptable carriers or diluents, into solid, semi-solid, liquid or gaseous forms, such as tablets, capsules, powders, granules, ointments, solutions, suppositories, injections, inhalants and aerosols. For oral preparations, the active agent may be used alone or in combination with appropriate additives to make tablets, powders, granules or capsules, for example, with conventional additives, such as lactose, mannitol, corn starch, or potato starch; with binders such as crystalline cellulose, cellulose derivatives, acacia, corn starch or gelatins; with disintegrators, such as corn starch, potato starch, or sodium carboxymethylcellulose; with lubricants, such as talc or magnesium stearate; and/or if desired, with diluents, buffering agents, moistening agents, preservatives and/or flavoring agents. Suitable pharmaceutically acceptable carriers include, without limitation, water, dextrose, glycerol, saline, ethanol, and/or combinations thereof.

In some embodiments, an active agent of a composition herein is formulated into a preparation for injection by dissolving, suspending or emulsifying the agent in an aqueous or non-aqueous solvent, such as vegetable or other similar oils, synthetic aliphatic acid glycerides, esters of high aliphatic acids, or propylene glycol; and if desired, with conventional additives such as solubilizers, isotonic agents, suspending agents, emulsifying agents, stabilizers and preservatives.

In some embodiments, an active agent of a composition herein is utilized in an aerosol formulation to be administered via inhalation. As examples, the agent is formulated into a pressurized acceptable propellant such as dichlorodifluoromethane, propane and nitrogen.

In some embodiments, an active agent of a composition herein is made into a suppository by mixing with a base, such as an emulsifying base or water-soluble base. In some instances, an active agent is administered rectally via a suppository. The suppository may include vehicles such as cocoa butter, carbowaxes and polyethylene glycols, which melt at body temperature, yet are solidified at room temperature.

In some embodiments, an active agent of a composition is formulation in an injectable composition. Typically, injectable compositions are prepared as liquid solutions or suspensions. In some instances, a solid form is provided which is suitable for solubilization or suspension in a liquid vehicle prior to injection. In other embodiments, an active agent is emulsified or the active agent is encapsulated in a liposome vehicle.

In some embodiments, unit dosage forms for oral or rectal administration, such as syrups, elixirs and suspensions are provided wherein each dosage unit (e.g., teaspoonful, tablespoonful, table, suppository) comprises a predetermined amount of the composition comprising one or more active agents. In some embodiments, unit dosage forms for injection or intravenous administration comprises the active agent in a composition as a solution in sterile water, normal saline or other pharmaceutically acceptable carrier.

In some embodiments, an active agent of a composition herein is formulated for delivery by a continuous or controlled delivery system. Examples include the use of continuous or controlled delivery devices in combination with catheters, injection devices and the like. In other or additional embodiments, the composition is delivered using a pump, including mechanical and electromechanical infusion pumps. In general, pumps provide consistent and/or controlled release of the composition over time. In some embodiments, the active agent is in a liquid formulation in a drug-impermeable reservoir, and is delivered in a continuous or controlled manner to a patient. In some embodiments, a drug delivery system is at least partially implantable. An implantable device can be implanted at any suitable implantation site using methods and devices well known in the art. Implantation sites include, but are not limited to, a subdermal, subcutaneous, intramuscular or other suitable site within a subject's body. Subcutaneous implantation sites are used in some embodiments for convenience in implantation and removal of the drug delivery device. In some embodiments, the active agent is delivered in a controlled release system. In exemplary embodiments, the active agent is administered using intravenous infusion, implantable osmotic pump, transdermal patch or liposomes.

In some embodiments, compositions suitable for transdermal administration employ transdermal delivery devices and transdermal delivery patches. In some cases, the compositions are formulated as lipophilic emulsions or buffered aqueous solutions, dissolved and/or dispersed in a polymer or an adhesive. Such patches are constructed for continuous, pulsatile, or on demand delivery of active agents. In some cases, transdermal delivery is accomplished by means of iontophoretic patches and the like. In some cases, transdermal patches provide controlled delivery. The rate of absorption can be slowed by using rate-controlling membranes or by trapping an active agent within a polymer matrix or gel. Conversely, absorption enhancers can be used to increase absorption. An absorption enhancer or carrier includes absorbable pharmaceutically acceptable solvents to assist passage through the skin. In an exemplary embodiment, transdermal devices are in the form of a bandage comprising a backing member, a reservoir containing active agents and optional carriers, a rate controlling barrier to deliver the agents to the skin of the subject at a controlled and predetermined rate over a prolonged period of time, and adhesives to secure the device to the skin.

In other embodiments, an active agent of a composition described herein is formulated into absorptive materials, such as sutures, bandages and gauze; or coated onto the surface of solid phase materials, such as surgical staples, zippers and catheters to deliver the agent.

Compositions described herein, in various implementations, comprise an immediate release form, a sustained-release form, a controlled release form, or a combination thereof. In some embodiments, an immediate release formulation is formulated to allow the active agents to act rapidly. Non-limiting examples of immediate release formulations include readily dissolvable formulations. In some embodiments, a controlled release formulation is a pharmaceutical formulation that has been adapted such that active agent release rates and release profiles can be matched to physiological and therapeutic requirements or, alternatively, is formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, granular masses, and the like. In some embodiments, a controlled release formulation is a delayed release form, wherein a delayed release form is formulated to delay action of an active agent for an extended period of time (e.g., for about 4, about 8, about 12, about 16, or about 24 hours).

In some embodiments, the active agents may be used in conjunction with other treatments that use sustained-release formulations. A sustained-release matrix, in many instances, is a matrix made of materials, usually polymers, which are degradable by enzymatic or acid-based hydrolysis or by dissolution. Once inserted into the body, the matrix may be acted upon by enzymes and body fluids. Examples of sustained-release matrix materials include, without limitation, liposomes, polylactides (polylactic acid), polyglycolide (polymer of glycolic acid), polylactide co-glylide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids (e.g., phenylalanine, tyrosine, isoleucine), polynucleotides, polyvinyl propylene, polyvinylpyrrolidone and silicone. Illustrative biodegradable matrices include a polylactide matrix, a polyglycolide matrix and a polylactide co-glycolide (co-polymers of lactic acid and glycolic acid) matrix.

The compositions used in the disclosed methods of treatment may be administered topically and can be incorporated into a delivery device. For example, a delivery device may be coated with or comprise the compositions disclosed herein. In some cases, the delivery device is a condom.

In some embodiments, the compositions and active agents described herein are delivered via vaginal devices which include, without limitation, intravaginal rings, vaginal tampons, vaginal strips, vaginal capsules, vaginal tablets, vaginal pessarys, vaginal cups, vaginal films, and vaginal sponges. In some embodiments, the compositions and active agents described herein are applied to the vagina of a subject in a number of forms including aerosols, foams, sprays, pastes, gels, jellies, creams, or suppositories. In some cases, the compositions are formulated for immediate release. In some embodiments, the compositions are formulated for long-acting, sustained release.

In various embodiments, intravaginal rings are designed to deliver a relatively constant dose of an active agent to the vagina, usually over a period of weeks to months. In some embodiments, the vaginal rings are made of a silicone elastomer and comprise an active agent released by diffusion through the elastomer. In some embodiments, the intravaginal ring comprises ethylene vinyl acetate. In some embodiments, the intravaginal ring is latex free. In some embodiments, the intravaginal ring comprises polyurethane. In some cases, the polyurethane is a polyesterurethane. In some cases, the intravaginal ring is biodegradable. In some embodiments, a vaginal ring comprises separate reservoirs containing different active agents. In some embodiments, a vaginal ring is a drug delivery device that is in the shape of a ring, a wafer, or suppository and is suitable for placement and retention inside a vagina. In some cases, the delivery device has an overall diameter of from about 10 mm to about 100 mm, and a cross-sectional diameter of from about 1 mm to about 15 mm.

In some embodiments, a composition described herein is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) comprising active agents, such as antivirals, and optionally carriers.

In some embodiments, an active agent of a composition described herein is packaged into a biological compartment. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles. For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment. Non-limiting examples of amphipathic compounds used in liposomes include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, di stearoylphosphatidylcholine (DSPC), dilinoleoylphosphatidylcholine and egg sphingomyelin, or any combination thereof.

In some embodiments, a biological compartment comprises a nanoparticle. In some cases, a nanoparticle comprises a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers. In some instances, as the size of the nanoparticle increases, the release rate can be slowed or prolonged and as the size of the nanoparticle decreases, the release rate can be increased. In some cases, the amount of albumin in the nanoparticles ranges from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. In some cases, a pharmaceutical composition comprises up to 30, 40, 50, 60, 70 or 80% or more of the nanoparticle. In some instances, active agents of the disclosure are be bound to the surface of the nanoparticle.

Dosing and Treatment Regimens

The compositions comprising one or more active agents described herein may be administered to a patient in one or more doses. In some embodiments, a composition comprises two or more active agents. In some embodiments, a composition comprising one or more active agents is administered with one or more addition compositions, each comprising one or more additional active agents. In some instances, a patient is administered one dose of one active agent and another dose of another active agent. In some embodiments, one or more active agents is an antiviral agent. In some embodiments, one or more active agents is a contraceptive.

In various embodiments, the compositions containing the one or more active agents described herein are administered for prophylactic and/or therapeutic treatments. In some prophylactic applications, the compositions are administered to a subject at risk for exposure to a virus. In some prophylactic applications, the compositions are administered to a subject exposed to a virus. In some prophylactic applications, the compositions are administered to a subject prior to and after exposure to a virus. In some embodiments, prophylactic compositions prevent or reduce the risk of viral infection in a seronegative individual. In some prophylactic applications, compositions containing the one or more active agents described herein are administered to a patient susceptible to or otherwise at risk of a particular disease, disorder or condition. Such an amount is defined to be a prophylactically effective amount or dose. In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In some embodiments, the disease is an infectious disease caused by a virus. In some cases, the virus is HSV. In some cases, the virus is HIV. In some cases the virus is VZV. In some cases the virus is EBV. In some cases the virus is CMV.

In some therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial. In some embodiments, the disease is an infectious disease caused by a virus. In some cases, the virus is HSV. In some cases, the virus is HIV.

In certain embodiments wherein the patient's condition does not improve, upon the doctor's discretion the administration of composition comprising the one or more active agents is administered chronically, that is, for an extended period of time, including throughout the duration of the patient's life in order to ameliorate or otherwise control or limit the symptoms of the patient's disease or condition.

In certain embodiments wherein a patient's status does improve, the dose of active agent(s) being administered is temporarily reduced or temporarily suspended for a certain length of time (i.e., a drug holiday). In some embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, for example, by 10%-100%, including only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

In some embodiments, the dose of an active agent administered to a patient varies depending on factors such as time point during therapy, identity of active agent or combination of active agents, identity of disease, disease condition/severity, identity of patient (e.g., age, weight, sex), and route of administration.

In some embodiments, a composition described herein comprises a low dose of an active agent, such as an antiviral agent. In some embodiments, the low dose of the antiviral agent is from about 50 mg to about 1 g. In some embodiments, the low dose of the antiviral agent is less than about 1,000 mg, less than about 900 mg, less than about 800 mg, less than about 700 mg, less than about 600 mg, less than about 500 mg, less than about 480 mg, less than about 460 mg, less than about 440 mg, less than about 420 mg, less than about 400 mg, less than about 380 mg, less than about 360 mg, less than about 340 mg, less than about 320 mg, less than about 300 mg, less than about 280 mg, less than about 260 mg, less than about 240 mg, less than about 220 mg, less than about 200 mg, less than about 180 mg, less than about 160 mg, less than about 140 mg, less than about 120 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 5 mg, or less than about 1 mg. In some cases, the low dose of the antiviral agent is between about 50 mg and about 500 mg, between about 50 mg and about 480 mg, between about 50 mg and about 460 mg, between about 50 mg and about 440 mg, between about 50 mg and about 420 mg, between about 50 mg and about 400 mg, between about 50 mg and about 380 mg, between about 50 mg and about 360 mg, between about 50 mg and about 340 mg, between about 50 mg and about 320 mg, between about 50 mg and about 300 mg, between about 50 mg and about 280 mg, between about 50 mg and about 260 mg, between about 50 mg and about 240 mg, between about 50 mg and about 220 mg, or between about 50 mg and about 200 mg. In some embodiments, the low dose of the antiviral agent is an amount similar to an amount of the antiviral agent useful for suppression treatment in an individual seropositive for the virus targeted by the antiviral agent. In some embodiments, the antiviral agent is an HSV antiviral agent. In some embodiments, the antiviral agent is an HIV antiviral agent.

In some embodiments, a composition described herein comprises a very high dose of an active agent, such as an antiviral agent. In some embodiments, the very high dose of the antiviral agent is from about 500 mg to about 5,000 mg. In some embodiments, the very high dose of the antiviral agent is greater than about 500 mg, greater than about 600 mg, greater than about 700 mg, greater than about 800 mg, greater than about 900 mg, greater than about 1,000 mg, greater than about 1,100 mg, greater than about 1,200 mg, greater than about 1,300 mg, greater than about 1,400 mg, greater than about 1,500 mg, greater than about 1,600 mg, greater than about 1,700 mg, greater than about 1,800 mg, greater than about 1,900 mg, greater than about 2,000 mg, greater than about 2,100 mg, greater than about 2,200 mg, greater than about 2,300 mg, greater than about 2,400 mg, greater than about 2,500 mg, greater than about 2,600 mg, greater than about 2,700 mg, greater than about 2,800 mg, greater than about 2,900 mg, greater than about 3,000 mg, greater than about 3,500 mg, greater than about 4,000 mg, greater than about 4,500 mg, or greater than about 5,000 mg. In some cases, the very high dose of the antiviral agent is between about 500 mg and about 5,000 mg, between about 600 mg and about 5,000 mg, between about 700 mg and about 5,000 mg, between about 800 mg and about 5,000 mg, between about 900 mg and about 5,000 mg, between about 1,000 mg and about 5,000 mg, between about 1,200 mg and about 5,000 mg, between about 1,400 mg and about 5,000 mg, between about 1,600 mg and about 5,000 mg, between about 1,800 mg and about 5,000 mg, between about 2,000 mg and about 5,000 mg, between about 2,200 mg and about 5,000 mg, between about 2,400 mg and about 5,000 mg, between about 2,600 mg and about 5,000 mg, between about 2,800 mg and about 5,000 mg, between about 3,000 mg and about 5,000 mg, or between about 3,200 mg and about 5,000 mg. In some embodiments, the very high dose of the antiviral agent is an amount greater than an amount of the antiviral agent useful for treatment of an outbreak in a seropositive individual infected with the virus targeted by the antiviral agent. In some embodiments, the antiviral agent is an HSV antiviral agent. In some embodiments, the antiviral agent is an HIV antiviral agent.

In some embodiments, an active agent is administered in about a 50 mg dosage. In some embodiments, an active agent is administered in about a 100 mg dosage. In some embodiments, an active agent is administered in about a 200 mg dosage. In some embodiments, an active agent is administered in about a 300 mg dosage. In some embodiments, an active agent is administered in about a 400 mg dosage. In some embodiments, an active agent is administered in about a 500 mg dosage. In some embodiments, an active agent is administered in about a 50 mg dosage. In some embodiments, an active agent is administered in about a 600 mg dosage. In some embodiments, an active agent is administered in about a 700 mg dosage. In some embodiments, an active agent is administered in about a 800 mg dosage. In some embodiments, an active agent is administered in about a 900 mg dosage. In some embodiments, an active agent is administered in about a 1,000 mg dosage. In some embodiments, an active agent is administered in about a 1,100 mg dosage. In some embodiments, an active agent is administered in about a 1,200 mg dosage. In some embodiments, an active agent is administered in about a 1,300 mg dosage. In some embodiments, an active agent is administered in about a 1,400 mg dosage. In some embodiments, an active agent is administered in about a 1,500 mg dosage. In some embodiments, an active agent is administered in about a 1,600 mg dosage. In some embodiments, an active agent is administered in about a 1,100 mg dosage. In some embodiments, an active agent is administered in about a 1,700 mg dosage. In some embodiments, an active agent is administered in about a 1,800 mg dosage. In some embodiments, an active agent is administered in about a 1,900 mg dosage. In some embodiments, an active agent is administered in about a 2,000 mg dosage. In some embodiments, an active agent is administered in about a 2,100 mg dosage. In some embodiments, an active agent is administered in about a 2,200 mg dosage. In some embodiments, an active agent is administered in about a 2,300 mg dosage. In some embodiments, an active agent is administered in about a 2,400 mg dosage. In some embodiments, an active agent is administered in about a 2,500 mg dosage. In some embodiments, an active agent is administered in about a 2,600 mg dosage. In some embodiments, an active agent is administered in about a 2,700 mg dosage. In some embodiments, an active agent is administered in about a 2,800 mg dosage. In some embodiments, an active agent is administered in about a 2,900 mg dosage. In some embodiments, an active agent is administered in about a 3,000 mg dosage. In some embodiments, an active agent is administered in about a 4,000 mg dosage. In some embodiments, an active agent is administered in about a 5,000 mg dosage. In some embodiments, an active agent is administered in about a 6,000 mg dosage. In some embodiments, an active agent is administered in about a 7,000 mg dosage. In some embodiments, an active agent is administered in about a 8,000 mg dosage. In some embodiments, an active agent is administered in about a 9,000 mg dosage. In some embodiments, the active agent is an antiviral agent. In some embodiments, the dosage is a very low dose. In some embodiments, the dosage is a very high dose. In some embodiments, the antiviral agent is an HSV antiviral agent. In some embodiments, the antiviral agent is an HIV antiviral agent.

In some embodiments, a composition described herein comprises 1, 2, 3, 4, 5 or more active agents. In some embodiments, 1, 2, 3, 4 or 5 of the active agents are antiviral agents. In some embodiments, one antiviral agent is administered at a low dosage (as described above, e.g., from about 50 mg to about 1 g) and one or more additional antiviral agents are administered at a second low dosage (as described above, e.g., from about 50 mg to about 1 g). In some embodiments, one antiviral agent is administered at a low dosage (as described above, e.g., from about 50 mg to about 1 g) and one or more additional antiviral agents are administered at a very high dosage (as described above, e.g., from about 500 mg to about 5,000 mg).

In many implementations of the disclosure, the amount of active agent per dose is determined on a per body weight basis. For example, in an embodiment, the active agent is administered in an amount of about 0.5 mg/kg body weight to about 100 mg/kg body weight. Those of skill will readily appreciate that dose levels often vary as a function of the specific active agent administered and the susceptibility of the subject to side effects. Preferred dosage forms of a given active agent are readily determinable by those of skill in the art. In some embodiments, the dosage or the amount of active agent in the dosage form are lower or higher than the ranges indicated herein, based on a number of variables in regard to an individual treatment regime. In various embodiments, the unit dosages are altered depending on a number of variables including, but not limited to, the activity of the agent, the mode of administration, the requirements of the individual subject, the condition of the patient (e.g., seronegative pre-exposure, seronegative post-exposure, seropositive), and/or the judgment of the practitioner.

In various embodiments, the dose of an active agent in a composition described herein is administered multiple times. The frequency of administration, in some instances, is dependent on the method of use, for example, for pre-exposure or post-exposure compositions. In some embodiments, an active agent is administered once per month, twice per month, three times per month, every other week, once per week, twice per week, three times per week, four times per week, five times per week, six times per week, every other day, daily, twice a day, three times a day, four times a day, five times a day, six times a day or more. In some embodiments, an active agent is administered continuously.

The duration of administration of the active agent (period of time over which the agent is administered), in many instances, varies depending on a number of factors. Examples of such factors include, without limitation, patient response, severity of symptoms, and disease type (e.g., virus type). In an example, an active agent is administered over a period of time of about one day to about one week, about one week to about two weeks, about two weeks to about four weeks, about one month to about two months, about two months to about four months, about four months to about six months, about six months to about eight months, about eight months to about 1 year, about 1 year to about 2 years or more.

In some embodiments, pharmaceutical compositions described herein are in unit dosage forms suitable for single administration of precise dosages. In some cases, in unit dosage form, the formulation is divided into unit doses containing appropriate quantities of one or more active agents. In some cases, the unit dosage is in the form of a package containing discrete quantities of the formulation. Non-limiting examples include packaged tablets or capsules, and powders in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

In some embodiments, an active agent described herein is present in a composition in a range of from about 1 mg to about 5,000 mg, from about 5 mg to about 5,000 mg, from about 10 mg to about 5,000 mg, from about 20 mg to about 5,000 mg, from about 30 mg to about 5,000 mg, from about 40 mg to about 5,000 mg, from about 50 mg to about 5,000 mg, from about 60 mg to about 5,000 mg, from about 70 mg to about 5,000 mg, from about 80 mg to about 5,000 mg, from about 90 mg to about 5,000 mg, from about 100 mg to about 5,000 mg, from about 120 mg to about 5,000 mg, from about 140 mg to about 5,000 mg, from about 160 mg to about 5,000 mg, from about 180 mg to about 5,000 mg, from about 200 mg to about 5,000 mg, from about 250 mg to about 5,000 mg, from about 300 mg to about 5,000 mg, from about 350 mg to about 5,000 mg, from about 400 mg to about 5,000 mg, from about 500 mg to about 5,000 mg, from about 1,000 mg to about 5,000 mg, or from about 2,000 mg to about 5,000 mg. In some embodiments, the active agent is present in a composition deliverable with an intravaginal ring. In some embodiments, the active agent is an antiviral agent. In some embodiments, the active agent is an HSV antiviral agent. In some embodiments, the active agent is an HIV antiviral agent. In some embodiments, the active agent is a contraceptive agent.

Kits

In some applications, an HSV prophylaxis and/or treatment kit is provided that includes an antiviral agent to be given to a subject in an effective amount such that HSV replication is suppressed, HSV activation is suppressed, or both; a delivery mechanism for the antiviral agent; dosage information specific to the antiviral agent; and use instructions specific to the delivery mechanism. In some instances, a kit can be used by a seronegative person or a seropositive person.

In certain instances, the drug delivery mechanism is a long-lasting drug delivery mechanism, which can include, for example, injection devices, intravaginal rings, or transdermal patches. The use instructions can include timing information on when to begin therapy, such as one to three weeks in advance of entering a demographic risk category, and may also include instructions on interval timing for maintaining the drug delivery mechanism. In some cases, the use instructions and dosage information can be provided via the internet.

In some embodiments, the kit comprises a composition as described herein. In some embodiments, the composition is a pre-exposure composition. In some embodiments, the composition is a post-exposure composition. In some embodiments, the composition is a composition for suppression therapy. In some embodiments, the kit comprises one, two or more active agents. In some embodiments, the active agents are formulated together. In other embodiments, the active agents are formulated separately. In some embodiments, the kit comprises a means to administrate a composition comprising one or more active agents as described herein.

In some embodiments, the kit comprises suitable instructions in order to perform the methods of the kit. The instructions may provide information of performing any of the methods disclosed herein, whether or not the methods may be performed using only the reagents provided in the kit. The kit and instructions may require additional reagents or systems.

In some embodiments, a kit provided herein includes a carrier means being compartmentalized to receive in close confinement one or more containers such as vials, tubes, and the like, each of the containers comprising one of the separate elements to be used in a method provided herein.

The following examples are provided to further illustrate the advantages and features of the present disclosure, but are not intended to limit the scope of the disclosure. While they are typical of those that might be used, other procedures, methodologies, or techniques known to those skilled in the art may alternatively be used.

EXAMPLES

Example 1: Inhibition of HSV-2 in Balb/c Mice

HSV-2 infection in mice is a model to analyze vaginal infection of HSV-2 and treatments to prevent HSV-2 infections or reactivation. The studies were done with all appropriate biosafety and IACUC approvals. The 2:1 ratio of valacyclovir:famciclovir is selected as representative of advantageous combination amounts. Efficacious ratios include about 5:1, about 4:1, about 3:1, about 2:1, about 1:1, about 1:2, about 1:3, about 1:4, or about 1:5. A ratio of about 2:1 valacyclovir:famciclovir may be preferred.

Experimental Design

Mice are placed randomly into 10 groups as describe in Table 1. Mice are treated with 3 mg/mouse of medroxyprogesterone 1 week prior to HSV-2 infection and a second dose is administered 24 hours before HSV-2 infection. Mice ARE treated with different doses of valacyclovir and/or famciclovir beginning 1 week prior to infection (FIG. 1). Mice in groups 1-8 are infected with HSV-2 by intravaginal route at $10^5$ pfu/20 μl.

Days −7 to end of study:
Mice are monitored daily
Illness score and vaginal infection score will be taken daily Mice are weighed daily (started at the time of infection)
Drug combinations are made daily
Mice are dosed with drug(s) daily by oral gavage
Weekly following HSV-2 infection
Vaginal swabs collected for future virus load analysis by ELIAN.
Serum collected and stored at −80
End of study: Day 28
Mice are weighed, vaginal cavity swabbed and mice euthanized by approved IACUC method.
Following euthanasia, dorsal root ganglia are sampled and stored for virus assay.
Serum collected and stored at −80
Materials
HSV-2, ATCC Lot No. 60299841, storage at −80° C.
Valacyclovir (compound A), supplier ELIAN, storage at 4° C.
Famciclovir (compound B), supplier ELIAN, storage at 4° C.
Test System
Species: Mice
Strain: BALB/c
Supplier: Jackson Laboratory
Number of Animals: 105
Sex: Female
Age at first dose: 10 weeks
Animal Care: General procedures for animal care and housing are in accordance with the current Association for Assessment and Accreditation of Laboratory Animal Care (AAALAC) recommendations, current requirements state in the *Guide for the Care and Use of Laboratory Animals* (National Research Council), and current requirements as stated by the U.S. Department of Agriculture through the Animal Welfare Act and Animal Welfare Regulations (November 2013)
Quarantine/Acclimation: At least 1 days
Housing: 5 mice per cage
Cages: Conventional cages
Light Cycle: 12 hr. light/12 hr. dark
Temperature: 68-79° F.
Humidity: 30-70%. Brief excursions outside this range may occur; excursions of less than 4 hr./day are not considered deviations from the protocol.
Ventilation: At least 10 room volumes per hour, with no recirculation of air
Food: Harlan Teklad Certified Rodent Chow #2018C or equivalent. Food is provided ad libitum.
Feed is analyzed periodically to ensure that contaminants known to be capable of interfering with the study and reasonable expected to be present in such feed are not present at levels that would affect the study. Documentation of feed analysis is maintained for reference. A copy of the lot specific reports provided by the supplier is maintained in the study records.
Water: Water (purified, reverse osmosis) is provided ad libitum. Based on previous reports, no contaminants that could interfere with and affect the results of the study are expected to be present in the water. Copies of annual analysis reports are maintained for reference.
Assignment of Animals to Study
Day: −7 day (prior to infection)
Randomization: Animals are randomly assigned to treatment groups. Animals may be excluded based on health, behavior, or inappropriate weight.
Identification: Animals are individually identified by a unique ear tattoo or by another approved method.
Welfare of the Animals: Every effort is made to minimize, if not eliminate, pain and suffering in all animals in the study. Moribund animals and animals experiencing undue pain and suffering are euthanized at the discretion of the Study Director, attending veterinarian, or other qualified person. The study Director makes every effort to protect the scientific validity of the study.
Experimental Procedure Methods
HSV-2 dose HSV-2 is administered at $10^5$ pfu intravaginal Administration: in 20 μl total volume
PBS is administered in 20 μl total volume intravaginal to control animals Compound dosing: ELIAN antiviral agents A(valacyclovir) and B (Famciclovir) at different doses are made fresh daily and inoculated by oral gavage at 200 μl/dose to each animal.
Mock treated mice receive by oral gavage 200 μl of PBS.
Mortality/Morbidity: Animals are checked at least once daily.
Clinical Observation: Recorded once daily or more often as clinical signs warrant. Animals are examined for any altered clinical signs, including gross motor and behavioral activity and observable changes in appearance (Table 4).
Body Weights: Body weights are recorded daily beginning at the time of infection, until the end of the study.
Clinical Lesion Scoring Vaginal lesions are scored on a scale of 1-4 (increments of 0.5) briefly as follows:
0=no disease
0.5=hair loss with no other symptoms
1=redness or swelling
2=a few small vesicles
3=several large vesicles
4=several large vesicles, paralysis
Vaginal swabs Weekly following infection vaginal swabs are taken by pre-moistening swabs with PBS.
Swabs are stored in PBS containing FBS at −80 for future use.
Serum collection Weekly following infection mice are bled and serum collected and store at −80 for future use.
Necropsy
Euthanasia: Isoflurane overdose followed by an approved secondary method thoracotomy
Tissues Retained: The following tissues are collected from each mouse: dorsal root ganglia and serum are stored at −80 for future virus assay.

One hundred and five mice were used for the study. Mice were placed randomly into 10 groups (Table 1) at 10 mice/group except group 8, mock treated HSV-2 infected control mice, had 15 mice in its group. 1 week prior to HSV-2 infection treatment of mice with ELIAN compounds A (valacyclovir) and B (famciclovir) began (FIG. 1). The treatment doses were made daily and the drug or drug combinations or vehicle were administered by oral gavage daily (200 μl total volume). One week prior to infection all mice received 3 mg/mouse of medroxyprogesterone (subcutaneous) in order to thin the vaginal epithelium. A second dose of 3 mg medroxyprogesterone was administered one day prior to infection.

Mice were inoculated with $1\times10^5$ pfu/ml of HSV-2 virus by intravaginal route. Mice were inoculated with virus or mock infected by first swabbing the vaginal tract with calcium alginate swabs to thin the lining. Following cleaning the vaginal tract, animals were inoculated intravaginal by instillation of 0.010 ml HSV2 directly into the vagina. Following infection weekly vaginal swabs were taken by pre-moistening swabs with BME media. Swabs were stored in media at −80. Weekly serum samples were collected and stored at −80. End of study dorsal root ganglia were collected, stored at −80 and analyzed.

Mice were monitored daily for mortality, vaginal clinical score, hair loss and illness. Untreated HSV-2 infected mice (Group 8) had significant mortality as compared to treated HSV-2 infected mice (FIG. 2). 12 of 15 HSV-2 infected mock treated mice succumbed to the infection. Of the 70 compound treated mice only 3 succumbed to the infection (mouse 19 (group 2), mouse 33 (group 4) and mouse 45 (group 5), FIG. 3).

TABLE 1

Experimental Setup

| Group | Test Compound[a] | Dose (mg/kg) | Route/Dose[d] | No. of animals | Infection |
|---|---|---|---|---|---|
| 1 | A | A - 125 | PO A - 1 mg/ml | 10 | HSV |
| 2 | B | B - 63 | PO B - 0.5 mg/ml | 10 | HSV |
| 3 | A + B | A - 32 B - 16 | PO A - 0.25 mg/ml B - 0.13 mg/ml | 10 | HSV |
| 4 | A + B | A - 63 B - 32 | PO A - 0.5 mg/ml B - 0.25 mg/ml | 10 | HSV |
| 5 | A + B | A - 125 B - 63 | PO A - 1.0 mg/ml B - 0.5 mg/ml | 10 | HSV |
| 6 | A + B | A - 250 B - 125 | PO A - 2 mg/ml B - 1 mg/ml | 10 | HSV |
| 7 | A + B | A - 500 B - 250 | PO A - 5 mg/ml B - 2 mg/ml | 10 | HSV |
| 8 | None | None | PO Vehicle | 15 | HSV[b,c] |
| 9 | A + B | A - 125 B - 63 | PO A - 1 mg/ml B - 0.5 mg/ml | 10 | None[c] |
| 10 | None | None | PO Vehicle | 10 | None[c] |

[a]A = Valacyclovir (VACV); B = Famciclovir (FCV)
[b]HSV-infected; untreated
[c]Control
[d]PO = per os, i.e. orally Body weight was measured daily following HSV-2 infection (Table 2-3). There was a loss of body weight between days 5-11 in mice infected with HSV-2 and mock treated (group 8, FIG. 4A). Mice in groups 1-4 had an overall similar body weight loss pattern as group 8 control infected mice (FIG. 4B-4E). Group 5 mice had an initial weight loss but rebounded earlier than controls (FIG. 4F). Group 6 and 7 mice maintained their body weight as compared to controls between days 5-11 post infection (FIGS. 4G-4H).

TABLE 2

Mouse Pharmacodynamics
Body Weights Summary - HSV infected compound treated mice
Body Weight (g)

| Day(s) Relative to HSV infection Date | | Group 1 HSV-2 A[a]: 125 mg/kg B: N/A | Group 2 HSV-2 A: N/A mg/kg B: 63 mg/kg | Group 3 HSV-2 A: 32 mg/kg B: 16 mg/kg | Group 4 HSV-2 A: 63 mg/kg B: 32 mg/kg | Group 5 HSV-2 A: 125 mg/kg B: 63 mg/kg | Group 6 HSV-2 A: 250 mg/kg B: 125 mg/kg | Group 7 HSV-2 A: 500 mg/kg B: 250 mg/kg |
|---|---|---|---|---|---|---|---|---|
| 1 | Mean | 100.00 | 100.00 | 100.00 | 100 | 100 | 100 | 100 |
| | SD | 0 | 0 | 0 | 0 | 0 | 0 | 0 |
| | N | 10 | 10 | 10 | 10 | 10 | 10 | 10 |
| 2 | Mean | 101 | 99 | 100 | 98 | 101 | 102 | 100 |
| | SD | 4 | 3 | 1 | 3 | 2 | 2 | 4 |
| | N | 10 | 10 | 10 | 10 | 10 | 10 | 10 |
| 3 | Mean | 101 | 100 | 101 | 100 | 96 | 101 | 98 |
| | SD | 4 | 3 | 2 | 3 | 4 | 5 | 6 |
| | N | 10 | 10 | 10 | 10 | 10 | 10 | 10 |
| 4 | Mean | 101 | 99 | 100 | 99 | 96 | 101 | 98 |
| | SD | 4 | 3 | 2 | 5 | 5 | 4 | 8 |
| | N | 10 | 10 | 10 | 10 | 10 | 10 | 10 |
| 5 | Mean | 101 | 100 | 101 | 101 | 99 | 101 | 95 |
| | SD | 3 | 3 | 2 | 6 | 3 | 3 | 7 |
| | N | 10 | 10 | 10 | 10 | 10 | 10 | 10 |
| 6 | Mean | 102 | 100 | 99 | 101 | 100 | 102 | 97 |
| | SD | 5 | 3 | 3 | 4 | 3 | 4 | 9 |
| | N | 10 | 10 | 10 | 10 | 10 | 10 | 10 |
| 7 | Mean | 104 | 99 | 96 | 99 | 97 | 100 | 99 |
| | SD | 5 | 3 | 3 | 4 | 5 | 7 | 7 |
| | N | 10 | 10 | 10 | 10 | 10 | 10 | 10 |
| 8 | Mean | 100 | 96 | 95 | 97 | 99 | 101 | 98 |
| | SD | 5 | 4 | 5 | 5 | 5 | 5 | 8 |
| | N | 10 | 10 | 10 | 10 | 10 | 10 | 10 |
| 9 | Mean | 98 | 94 | 92 | 93 | 99 | 102 | 99 |
| | SD | 3 | 4 | 7 | 4 | 4 | 5 | 6 |
| | N | 10 | 10 | 10 | 10 | 10 | 10 | 10 |
| 10 | Mean | 96 | 92 | 90 | 92 | 97 | 101 | 99 |
| | SD | 5 | 6 | 7 | 6 | 3 | 5 | 7 |
| | N | 10 | 10 | 10 | 10 | 10 | 10 | 10 |
| 11 | Mean | 92 | 91 | 90 | 92 | 97 | 101 | 100 |
| | SD | 7 | 7 | 8 | 6 | 3 | 5 | 9 |
| | N | 10 | 10 | 10 | 10 | 10 | 10 | 10 |

TABLE 2-continued

Mouse Pharmacodynamics
Body Weights Summary - HSV infected compound treated mice
Body Weight (g)

| Day(s) Relative to HSV infection Date | | Group 1 HSV-2 A[a]: 125 mg/kg B: N/A | Group 2 HSV-2 A: N/A B: 63 mg/kg | Group 3 HSV-2 A: 32 mg/kg B: 16 mg/kg | Group 4 HSV-2 A: 63 mg/kg B: 32 mg/kg | Group 5 HSV-2 A: 125 mg/kg B: 63 mg/kg | Group 6 HSV-2 A: 250 mg/kg B: 125 mg/kg | Group 7 HSV-2 A: 500 mg/kg B: 250 mg/kg |
|---|---|---|---|---|---|---|---|---|
| 12 | Mean | 95 | 89 | 93 | 97 | 102 | 107 | 98 |
|    | SD | 10 | 8 | 8 | 5 | 6 | 4 | 9 |
|    | N | 10 | 9 | 10 | 10 | 10 | 10 | 10 |
| 13 | Mean | 91 | 96 | 91 | 93 | 97 | 102 | 97 |
|    | SD | 20 | 6 | 8 | 8 | 7 | 5 | 9 |
|    | N | 10 | 9 | 10 | 10 | 10 | 10 | 10 |
| 14 | Mean | 97 | 93 | 91 | 92 | 97 | 100 | 100 |
|    | SD | 7 | 5 | 8 | 7 | 7 | 7 | 9 |
|    | N | 10 | 9 | 10 | 10 | 10 | 10 | 10 |
| 15 | Mean | 92 | 93 | 91 | 94 | 96 | 101 | 99 |
|    | SD | 18 | 5 | 7 | 6 | 4 | 8 | 8 |
|    | N | 10 | 9 | 10 | 10 | 10 | 10 | 10 |
| 16 | Mean | 97 | 95 | 90 | 92 | 95 | 104 | 99 |
|    | SD | 4 | 4 | 6 | 9 | 4 | 6 | 8 |
|    | N | 10 | 9 | 10 | 10 | 10 | 10 | 10 |
| 17 | Mean | 99 | 93 | 94 | 96 | 98 | 102 | 100 |
|    | SD | 4 | 5 | 6 | 7 | 3 | 5 | 8 |
|    | N | 10 | 9 | 10 | 10 | 10 | 10 | 10 |
| 18 | Mean | 101 | 97 | 92 | 95 | 96 | 101 | 101 |
|    | SD | 2 | 5 | 5 | 8 | 3 | 4 | 9 |
|    | N | 10 | 9 | 10 | 10 | 10 | 10 | 10 |
| 19 | Mean | 100 | 95 | 96 | 98 | 100 | 104 | 98 |
|    | SD | 3 | 6 | 5 | 9 | 5 | 4 | 8 |
|    | N | 10 | 9 | 10 | 10 | 10 | 10 | 10 |
| 20 | Mean | 100 | 98 | 95 | 97 | 99 | 104 | 99 |
|    | SD | 3 | 5 | 5 | 9 | 4 | 4 | 8 |
|    | N | 10 | 9 | 10 | 10 | 10 | 10 | 10 |
| 21 | Mean | 101 | 97 | 98 | 100 | 96 | 103 | 99 |
|    | SD | 5 | 5 | 5 | 7 | 5 | 4 | 9 |
|    | N | 10 | 9 | 10 | 9 | 10 | 10 | 10 |
| 22 | Mean | 100 | 99 | 93 | 95 | 95 | 100 | 92 |
|    | SD | 5 | 5 | 4 | 4 | 10 | 3 | 10 |
|    | N | 10 | 9 | 10 | 9 | 10 | 10 | 10 |
| 23 | Mean | 96 | 96 | 92 | 93 | 98 | 101 | 91 |
|    | SD | 7 | 4 | 4 | 5 | 5 | 3 | 10 |
|    | N | 10 | 9 | 10 | 9 | 10 | 10 | 10 |
| 24 | Mean | 97 | 95 | 93 | 95 | 98 | 100 | 94[c] |
|    | SD | 8 | 4 | 3 | 5 | 6 | 4 | 9 |
|    | N | 10 | 9 | 10 | 9 | 10 | 9[b] | 10 |
| 25 | Mean | 99 | 98 | 93 | 96 | 98 | 100 | 95 |
|    | SD | 6 | 5 | 4 | 3 | 5 | 5 | 7 |
|    | N | 10 | 9 | 10 | 9 | 10 | 9 | 10 |
| 26 | Mean | 97 | 95 | 94 | 95 | 97 | 99 | 97 |
|    | SD | 5 | 5 | 4 | 4 | 5 | 5 | 9 |
|    | N | 10 | 9 | 10 | 9 | 10 | 9 | 10 |
| 27 | Mean | 98 | 97 | 94 | 95 | 98 | 99 | 96 |
|    | SD | 4 | 4 | 4 | 4 | 5 | 5 | 8 |
|    | N | 10 | 9 | 10 | 9 | 10 | 9 | 10 |
| 28 | Mean | 99 | 96 | 95 | 96 | 96 | 99 | 100 |
|    | SD | 6 | 4 | 4 | 5 | 6 | 6 | 8 |
|    | N | 10 | 9 | 10 | 9 | 10 | 9 | 10 |

[a] A = Valacyclovir (VACV); B = Famciclovir (FCV)

[b] mouse died during bleeding

[c] group 7 mice were not dosed on day 24 due to ruffled and weight loss

TABLE 3

Mouse Pharmacodynamics
Body Weights Summary - Control Groups of mice
Body Weight (g)

| Day(s) Relative to HSV infection Date | | Group 8 Mock Treated Infected with HSV | Group 9 A[a]: 125 mg/kg B: 63 mg/kg Mock infected | Group 10 Mock infected Mock treated |
|---|---|---|---|---|
| 1 | Mean | 100 | 100 | 100 |
|   | SD | 0 | 0 | 0 |
|   | N | 15 | 10 | 10 |
| 2 | Mean | 100 | 98 | 100 |
|   | SD | 1 | 4 | 1 |
|   | N | 15 | 10 | 10 |
| 3 | Mean | 99 | 102 | 103 |
|   | SD | 2 | 7 | 2 |
|   | N | 15 | 10 | 10 |
| 4 | Mean | 100 | 106 | 104 |
|   | SD | 2 | 6 | 3 |
|   | N | 15 | 10 | 10 |
| 5 | Mean | 99 | 106 | 102 |
|   | SD | 2 | 6 | 2 |
|   | N | 15 | 10 | 10 |
| 6 | Mean | 98 | 105 | 104 |
|   | SD | 3 | 5 | 2 |
|   | N | 15 | 10 | 10 |
| 7 | Mean | 95 | 105 | 104 |
|   | SD | 6 | 5 | 3 |
|   | N | 12 | 10 | 10 |
| 8 | Mean | 97 | 107 | 104 |
|   | SD | 8 | 6 | 3 |
|   | N | 11 | 10 | 10 |
| 9 | Mean | 96 | 105 | 104 |
|   | SD | 7 | 6 | 2 |
|   | N | 10 | 10 | 10 |
| 10 | Mean | 93 | 104 | 104 |
|   | SD | 10 | 7 | 3 |
|   | N | 8 | 10 | 10 |
| 11 | Mean | 90 | 106 | 105 |
|   | SD | 12 | 6 | 2 |
|   | N | 4 | 10 | 10 |
| 12 | Mean | 98 | 109 | 106 |
|   | SD | 5 | 6 | 2 |
|   | N | 4 | 10 | 10 |
| 13 | Mean | 97 | 109 | 106 |
|   | SD | 6 | 5 | 2 |
|   | N | 4 | 10 | 10 |
| 14 | Mean | 97 | 109 | 103 |
|   | SD | 8 | 4 | 3 |
|   | N | 4 | 10 | 10 |
| 15 | Mean | 97 | 108 | 105 |
|   | SD | 8 | 5 | 3 |
|   | N | 4 | 10 | 10 |
| 16 | Mean | 98 | 106 | 104 |
|   | SD | 7 | 5 | 2 |
|   | N | 4 | 10 | 10 |
| 17 | Mean | 96 | 106 | 104 |
|   | SD | 8 | 5 | 3 |
|   | N | 4 | 10 | 10 |
| 18 | Mean | 96 | 108 | 105 |
|   | SD | 8 | 5 | 2 |
|   | N | 4 | 10 | 10 |
| 19 | Mean | 95 | 108 | 105 |
|   | SD | 7 | 6 | 3 |
|   | N | 4 | 10 | 10 |
| 20 | Mean | 97 | 108 | 103 |
|   | SD | 8 | 6 | 3 |
|   | N | 3 | 10 | 10 |
| 21 | Mean | 101 | 108 | 102 |
|   | SD | 2 | 6 | 3 |
|   | N | 3 | 10 | 10 |
| 22 | Mean | 101 | 108 | 102 |
|   | SD | 1 | 7 | 3 |
|   | N | 3 | 10 | 10 |
| 23 | Mean | 101 | 109 | 103 |
|   | SD | 3 | 9 | 5 |
|   | N | 3 | 10 | 10 |
| 24 | Mean | 101 | 109 | 103 |
|   | SD | 3 | 10 | 4 |
|   | N | 3 | 10 | 10 |
| 25 | Mean | 100 | 109 | 103 |
|   | SD | 2 | 10 | 4 |
|   | N | 3 | 10 | 10 |
| 26 | Mean | 100 | 109 | 103 |
|   | SD | 1 | 10 | 5 |
|   | N | 3 | 10 | 10 |
| 27 | Mean | 101 | 110 | 103 |
|   | SD | 1 | 10 | 4 |
|   | N | 3 | 10 | 10 |
| 28 | Mean | 99 | 110 | 103 |
|   | SD | 1 | 9 | 4 |
|   | N | 3 | 10 | 10 |

[a] A = Valacyclovir (VACV); B = Famciclovir (FCV)

Figure 6A:
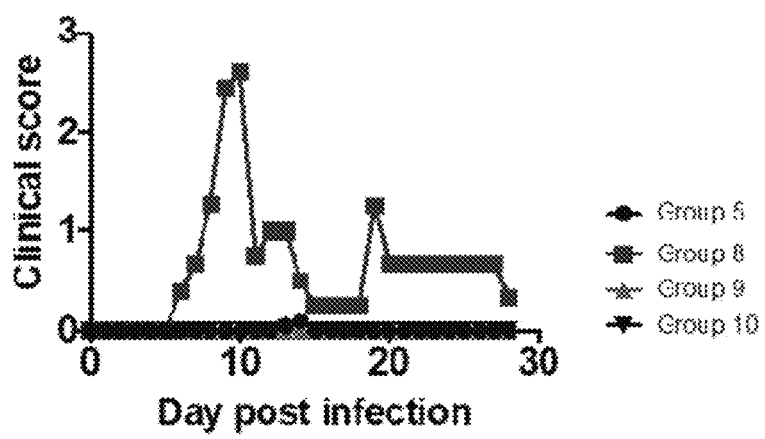
FIG. 6A-6C. Clinical score of groups 5-7. Mice were monitored daily following infection for vaginal clinical scores using a 4-point system (Table 4): 0=no disease, 1+ redness or swelling (genital erythema), 2+a few small vesicles (moderate genital infection), 3+ purulent genital ulceration, hair loss, poor condition, and 4+ severe ulcerations with maceration, hind limb paralysis (leading to euthanasia). (A) Group 5 as compared to controls. (B) group 6 as compared to controls. (C) group 7 as compared to controls.
Figure 6B:
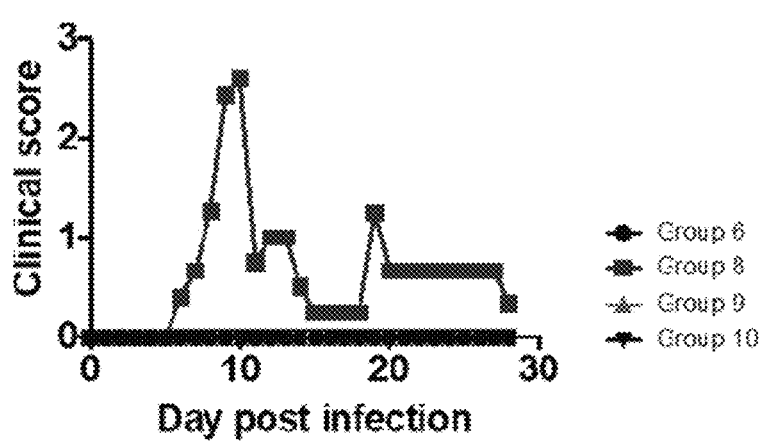
Figure 6C:
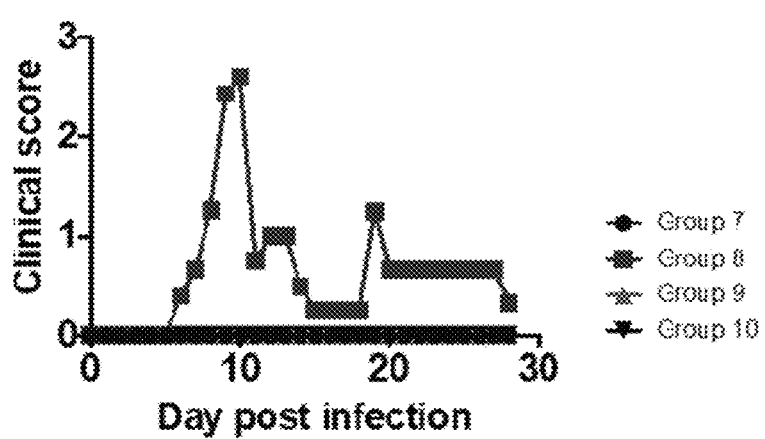
Figure 7:
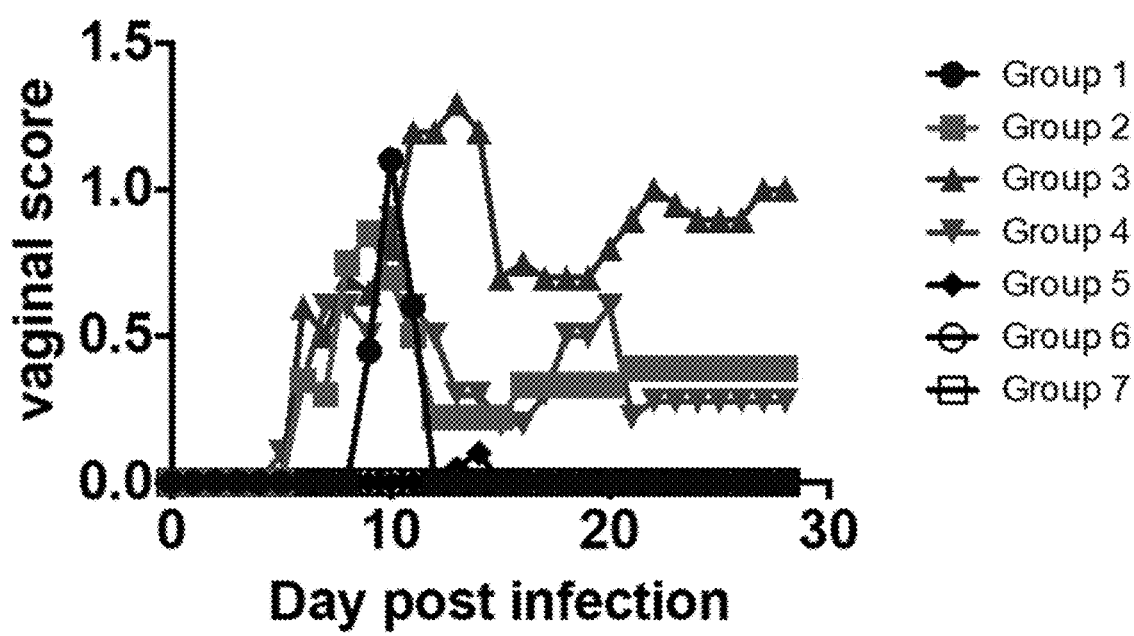
FIG. 7. Comparison of clinical score in treated mice. Mice were treated with different doses of compound(s) and infected with HSV-2. Mice were monitored daily following infection for vaginal clinical scores using a 4-point system (Table 4): 0=no disease, 1+ redness or swelling (genital erythema), 2+a few small vesicles (moderate genital infection), 3+ purulent genital ulceration, hair loss, poor condition, and 4+ severe ulcerations with maceration, hind limb paralysis (leading to euthanasia). A comparison of group clinical scores in HSV-2 infected compound treated mice. Group 3 clinical score was significantly higher than all other groups of infected and treated mice (2-way ANOVA, $p<0.0001$).

Mice were monitored daily for clinical disease using a 4-point system (Table 4): 0=no disease, 1+ redness or swelling (genital erythema), 2+a few small vesicles (moderate genital infection), 3+ purulent genital ulceration, hair loss, poor condition, and 4+ severe ulcerations with maceration, hind limb paralysis (leading to euthanasia). Intermediate scores were given to animals with in between severity. Group 8 mice had the highest clinical score as compared to all other groups of infected mice (FIGS. 5 and 6). When comparing mice treated with compound, group 3 had the highest clinical score (FIG. 7). Group 3 was treated with the lowest doses of both compound A and B.

TABLE 4

Clinical scoring template

| | Score | Description |
|---|---|---|
| Clinical Score | 0 | No apparent infection |
| | 0.5 | Hair loss with no other symptoms |
| | 1 | Genital erythema |
| | 2 | Moderate genital infection |
| | 3 | Purulent genital ulceration and hair loss, poor condition |
| | 4 | Severe ulceration of genital and surrounding tissue, hind limb paralysis (euthansia) |

Figure 8:
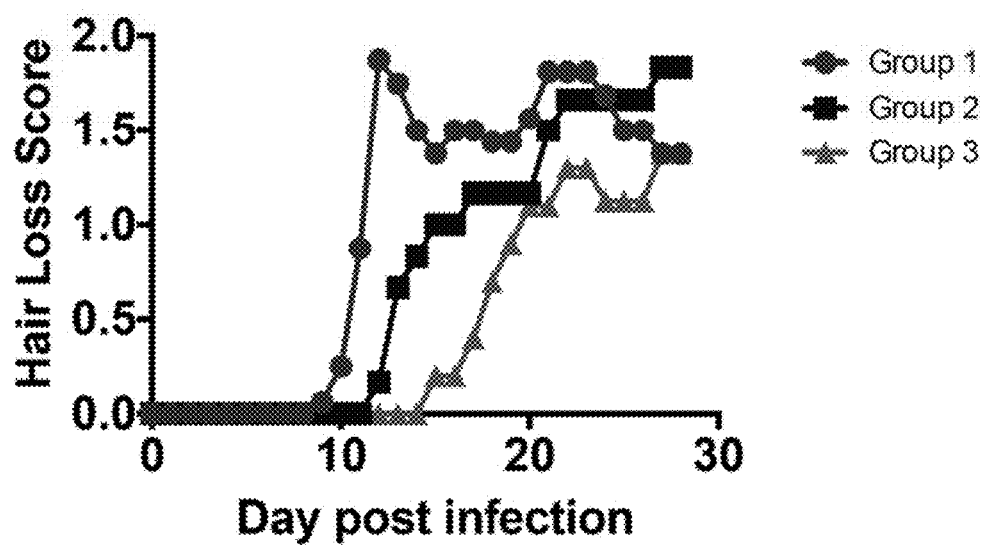
FIG. 8. Hair loss following infection with HSV-2. Mice were treated with different doses of compound(s) and infected with HSV-2. Mice were monitored daily following infection for hair loss using the following point system (Table 5): 0.5 minor hair loss, 1+ patch of hair loss, 2+ hair loss extending to back, 3+ hair loss extending to back and limbs A comparison of group hair loss scores in HSV-2 infected compound treated mice.
Figure 8:
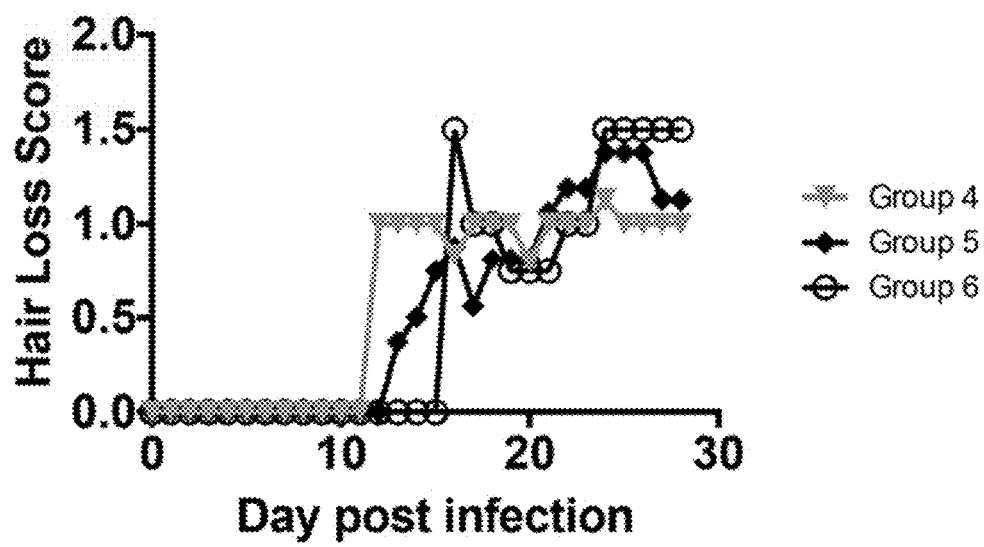
Figure 9A:
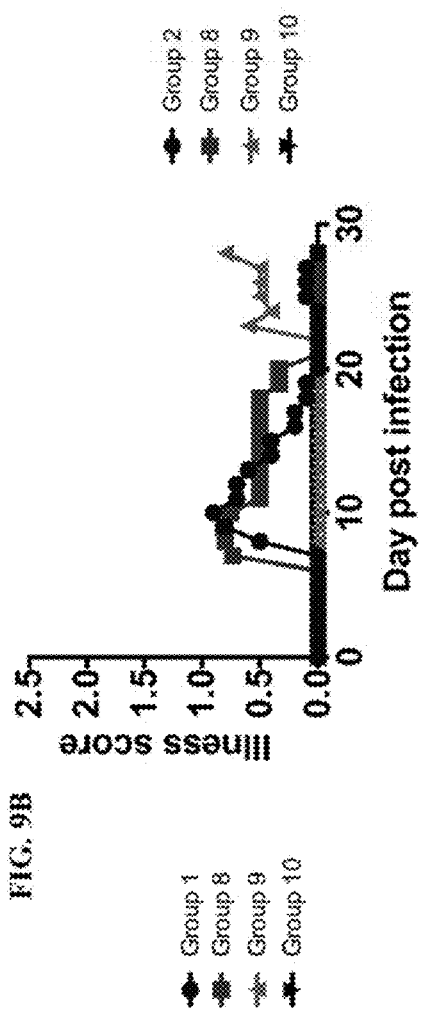
FIG. 9A-9D. Illness score following infection with HSV-2. Mice were treated with different doses of compound(s) and infected with HSV-2. Illness scores were recorded daily using a 4-point system (Table 6): 0=healthy, 1+ ruffled fur, 2+ arched back, 3+ lethargic to touch, and 4+ paralysis of one or both hind limbs. (A) Group 1 as compared to controls. (B) Group 2 as compared to controls. (C) Group 3 as compared to controls. (D) Group 4 as compared to controls. Note that past day 7 only 3/15 mice survived in group 8 (untreated/infected).
Figure 9C:
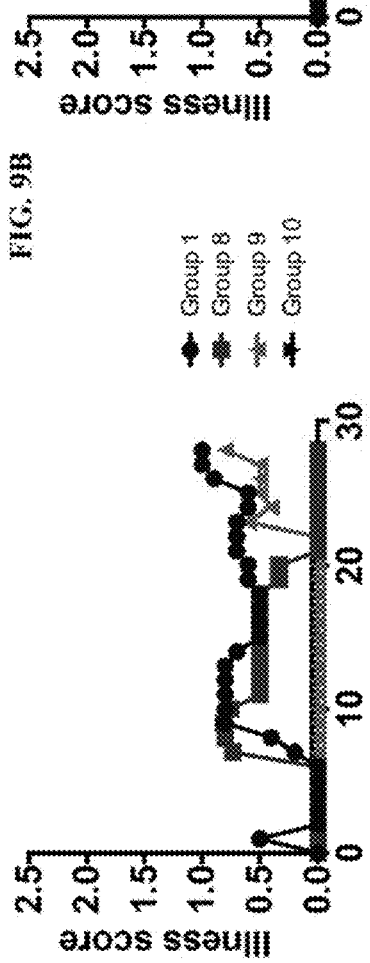
Figure 9B:
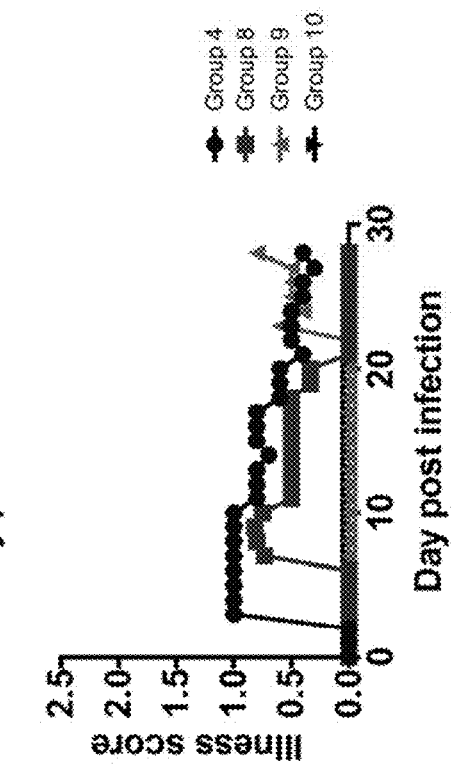
Figure 9D:
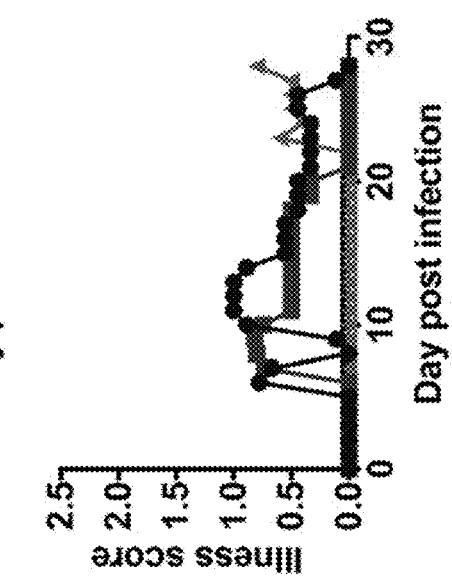

Notably, on some days many mice had vaginal hair loss without any other symptoms. We therefore generated a hair loss only point system (Table 5): 0.5 minor hair loss, 1+ patch of hair loss, 2+ hair loss extending to back, 3+ hair loss extending to back and limbs. Some level of hair loss was seen in some mice in groups 1-6 (FIG. 8). Group 7, which was treated with the highest doses of compound, had no hair loss or clinical score.

TABLE 5

Hair loss only scoring template

| | Score | Description |
|---|---|---|
| Hair loss Score | 0 | No hair loss |
| | 0.5 | Minor hair loss |
| | 1 | Patch of hair loss |

TABLE 5-continued

Hair loss only scoring template

| Score | Description |
|---|---|
| 2 | Hair loss extending to back |
| 3 | Hair loss extending to back and limbs |

Figure 10A:
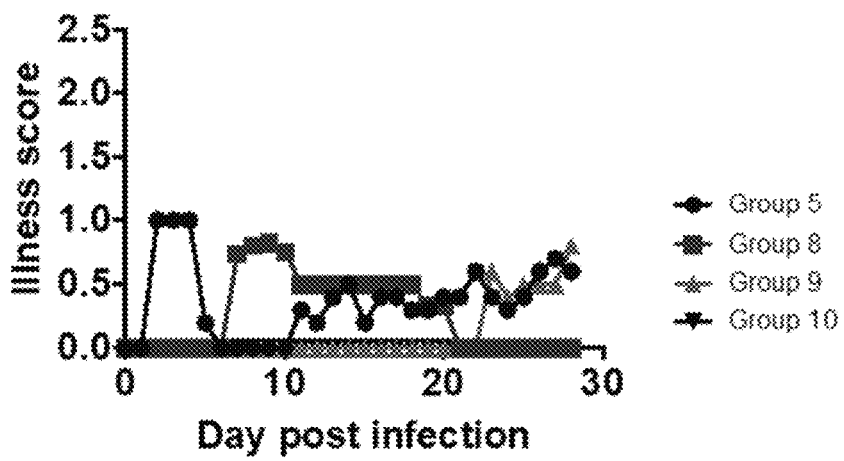
FIG. 10A-10C. Illness score following infection with HSV-2. Mice were treated with different doses of compound(s) and infected with HSV-2. Illness scores were recorded daily using a 4-point system (Table 6): 0=healthy, 1+ ruffled fur, 2+ arched back, 3+ lethargic to touch, and 4+ paralysis of one or both hind limbs. (A) Group 5 as compared to controls. (B) Group 6 as compared to controls. (C) Group 7 as compared to controls.
Figure 10B:
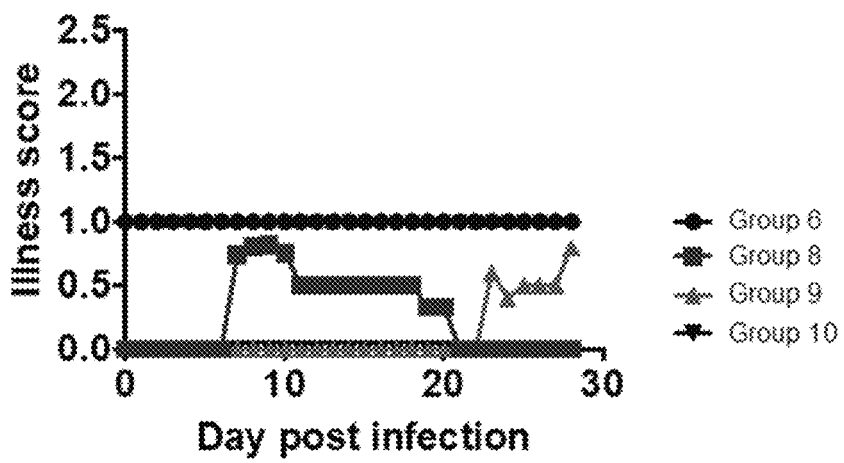
Figure 10C:
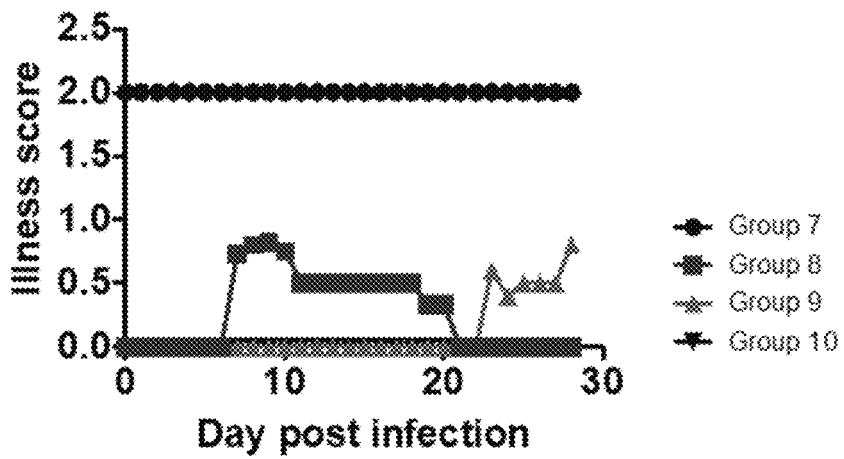

Illness scores were recorded daily using a 4-point system (Table 6): 0=healthy, 1+ ruffled fur, 2+ arched back, 3+ lethargic to touch, and 4+ paralysis of one or both hind limbs. The most common illness score was ruffled fur (FIGS. 9-10). Of note, mice in groups 6 and 7 had a ruffled (group 6, FIG. 10) and severe ruffled (group 7, FIG. 10) that was present at the time of infection suggesting that the dosage of the compounds caused the illness score.

TABLE 6

Illness scoring template

| | Score | Description |
|---|---|---|
| Illness score | 0 | Healthy |
| | 1 | Ruffled fur |
| | 2 | Ruffled fur and arched back |
| | 3 | Ruffled fur, arched back and lethargic to touch |
| | 4 | Ruffled fur, arched back, lethargic, and paralysis of one or both hind limbs |

Survival

Figure 2A:
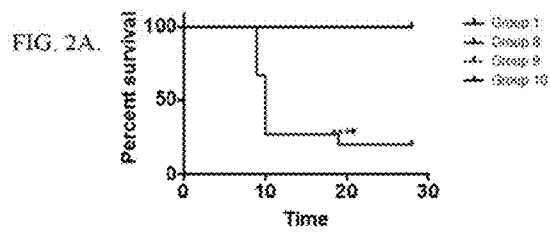
FIG. 2A-2G. Survival Curves. Group 9 mice were treated with 125 mg/kg Valacyclovir and 63 mg/kg Famciclovir and mock infected. Group 10 mice were mock treated and mock infected. Mice were monitored daily for survival. Comparisons of survival curves were done by Log-rank (Mantel-Cox) test *** $p<0.001$. (A) Group 1 mice were treated daily with 125 mg/kg of Valacyclovir by oral gavage beginning 7 days prior to infection. Groups 1 and 8 (mock treated) were infected with $10^5$ HSV-2 MS strain intravaginal. (B) Group 2 mice were treated daily with 63 mg/kg Famciclovir by oral gavage beginning 7 days prior to infection. Groups 2 and 8 (mock treated) were infected with $10^5$ HSV-2 MS strain intravaginal. (C) Group 3 mice were treated daily with 32 mg/kg Valacyclovir 16 mg/kg Famciclovir by oral gavage beginning 7 days prior to infection. Groups 3 and 8 (mock treated) were infected with $10^5$ HSV-2 MS strain intravaginal. (D) Group 4 mice were treated daily with 63 mg/kg Valacyclovir 32 mg/kg Famciclovir by oral gavage beginning 7 days prior to infection. Groups 4 and 8 (mock treated) were infected with $10^5$ HSV-2 MS strain intravaginal. (E) Group 5 mice were treated daily with 125 mg/kg Valacyclovir and 63 mg/kg Famciclovir by oral gavage beginning 7 days prior to infection. Groups 5 and 8 (mock treated) were infected with $10^5$ HSV-2 MS strain intravaginal. (F) Group 6 mice were treated daily with 250 mg/kg Valacyclovir and 125 mg/kg Famciclovir by oral gavage beginning 7 days prior to infection. Groups 6 and 8 (mock treated) were infected with $10^5$ HSV-2 MS strain intravaginal. (G) Group 7 mice were treated daily with 500 mg/kg Valacyclovir and 250 mg/kg Famciclovir by oral gavage beginning 7 days prior to infection. Groups 7 and 8 (mock treated) were infected with $10^5$ HSV-2 MS strain intravaginal.
Figure 2B:
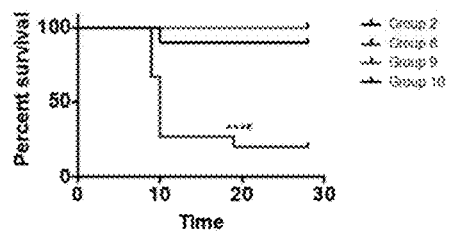
Figure 2C:
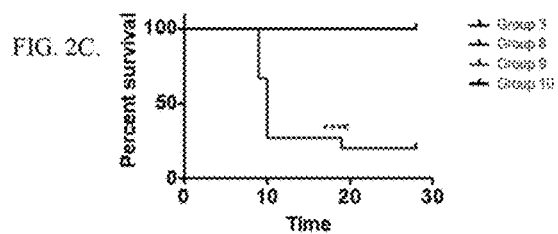
Figure 2D:
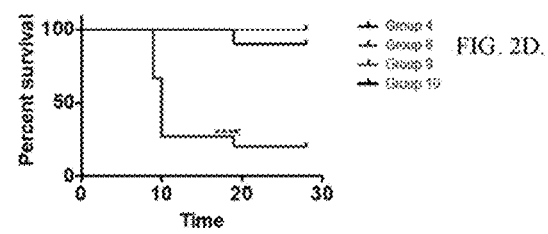
Figure 2E:
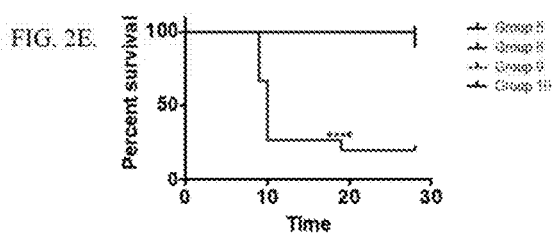
Figure 2F:
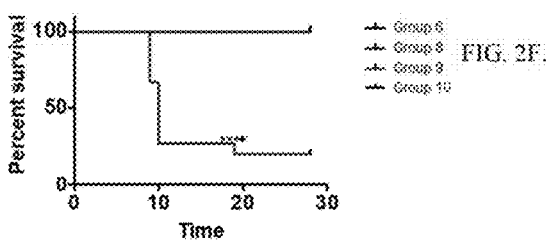
Figure 2G:
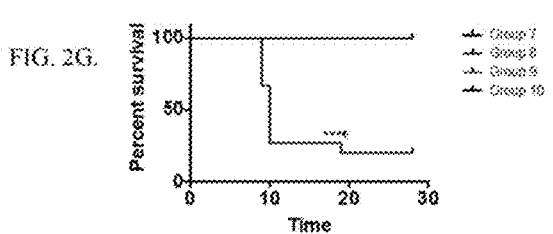

Overall, 12 of 15 HSV-2 infected treatment control mice succumbed to infection. Most of the infected control mice died by day 10 post infection (FIG. 2A). Of the infected control mice, group 8, that survived, mice 71 and 80 had no or low illness score and low vaginal scores. Mouse 72 did have illness and clinical scores but also survived to the end of the study.

Figure 3:
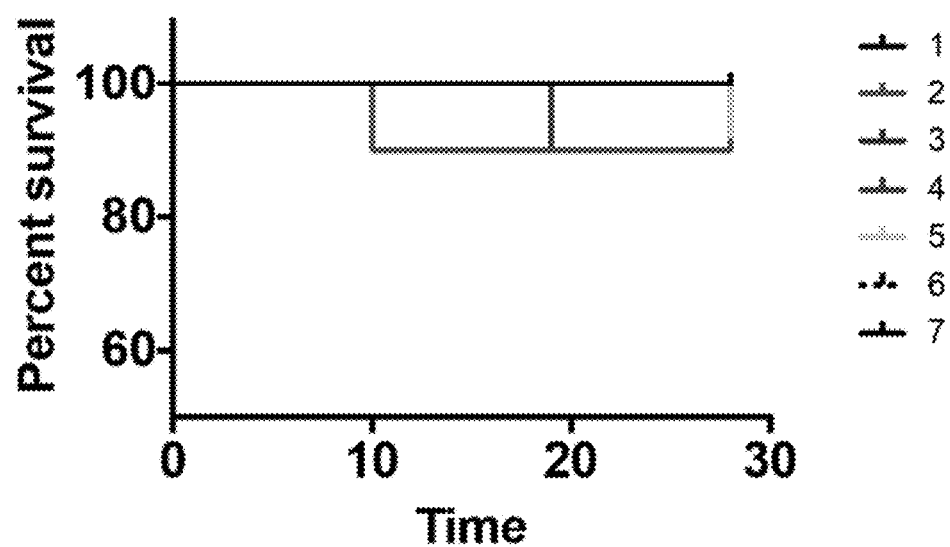
FIG. 3. Compound treated HSV-2 infected survival curve. Group 1-7 mice were treated daily with different doses and combinations of the drugs Valacyclovir and Famciclovir (table 1) by oral gavage beginning 7 days prior to infection. Mice were monitored daily for survival.

70 mice were treated with different doses of compounds A and B (Table 1) and infected with HSV-2. 1 mouse was removed from the study due to accidental asphyxiation during bleeding. Of the remaining 69 mice, 3 succumbed to the infection. The survival curve of all treated mice as compared to untreated infected control mice were significant (FIGS. 2A-2G). Although mice from groups 2, 4 and 5 had mice that died following infection, the survival curve in these groups was not significantly different than other treated groups of mice (FIG. 3).

Weight

Figure 4A:
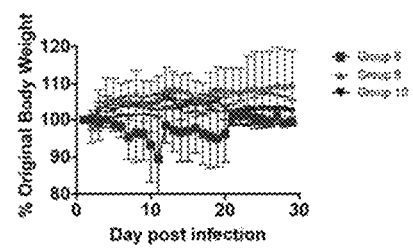
FIG. 4A-4H. Body weight is shown post infection as % of original body weight. Comparison is to group 8 control HSV-2 infected mice, group 9 control compound treated mice and group 10 control mock infected and mock treated mice. Mice were weighed daily during infection and the % original body weight calculated. (A) Group 1 mice were treated daily with 125 mg/kg of Valacyclovir by oral gavage beginning 7 days prior to infection. (B) Group 2 mice were treated daily with 63 mg/kg Famciclovir by oral gavage beginning 7 days prior to infection. (C) Group 3 mice were treated daily with 32 mg/kg Valacyclovir 16 mg/kg Famciclovir by oral gavage beginning 7 days prior to infection. (D) Group 4 mice were treated daily with 63 mg/kg Valacyclovir 32 mg/kg Famciclovir by oral gavage beginning 7 days prior to infection. (E) Group 4 mice were treated daily with 63 mg/kg Valacyclovir 32 mg/kg Famciclovir by oral gavage beginning 7 days prior to infection. (F) Group 5 mice were treated daily with 125 mg/kg Valacyclovir and 63 mg/kg Famciclovir by oral gavage beginning 7 days prior to infection. (G) Group 6 mice were treated daily with 250 mg/kg Valacyclovir and 125 mg/kg Famciclovir by oral gavage beginning 7 days prior to infection. (H) Group 7 mice were treated daily with 500 mg/kg Valacyclovir and 250 mg/kg Famciclovir by oral gavage beginning 7 days prior to infection.
Figure 4B:
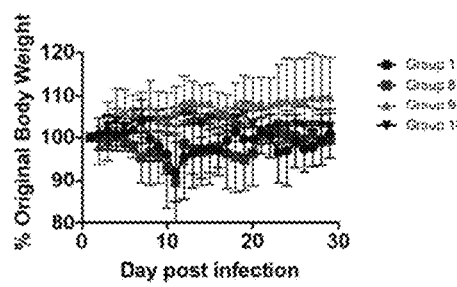
Figure 4C:
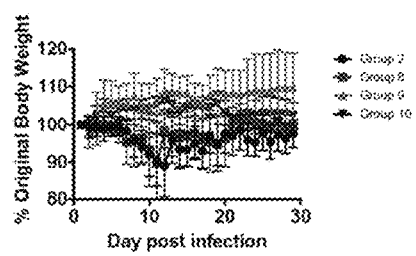
Figure 4D:
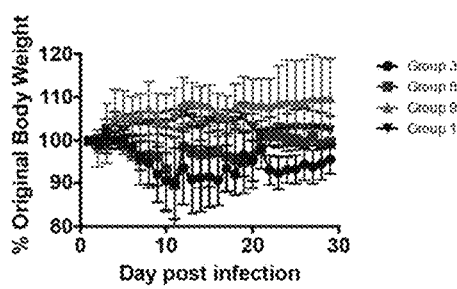
Figure 4E:
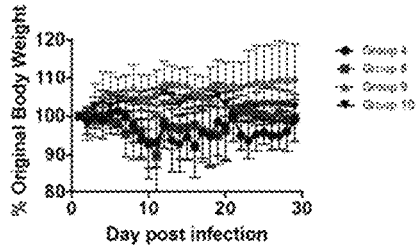
Figure 4F:
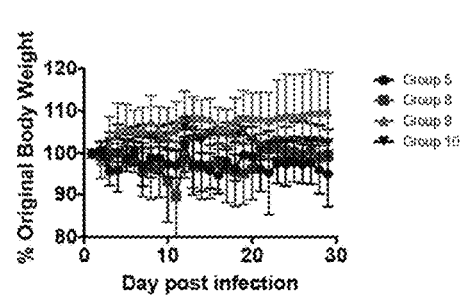
Figure 4G:
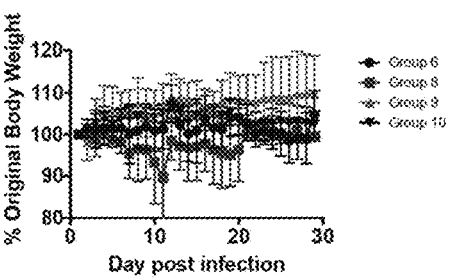
Figure 4H:
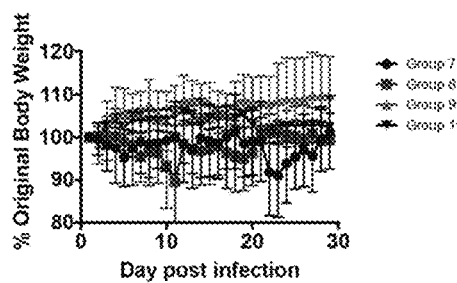
Figure 5A:
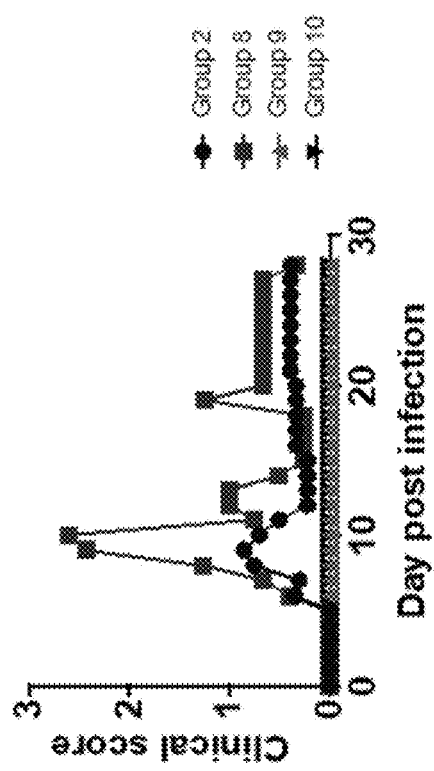
FIG. 5A-5D. Clinical scores of groups 1-4. Mice were monitored daily following infection for vaginal clinical scores using a 4-point system (Table 4): 0=no disease, 1+ redness or swelling (genital erythema), 2+a few small vesicles (moderate genital infection), 3+ purulent genital ulceration, hair loss, poor condition, and 4+ severe ulcerations with maceration, hind limb paralysis (leading to euthanasia). (A) Group 1 as compared to controls. (B) group 2 as compared to controls. (C) group 3 as compared to controls. (D) group 4 as compared to controls.
Figure 5B:
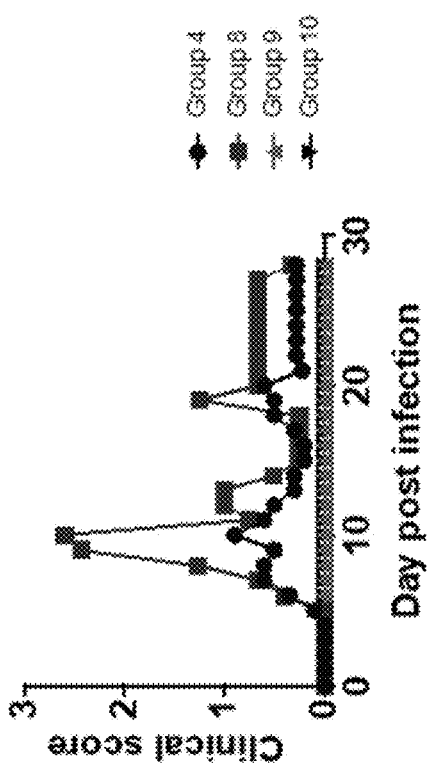
Figure 5C:
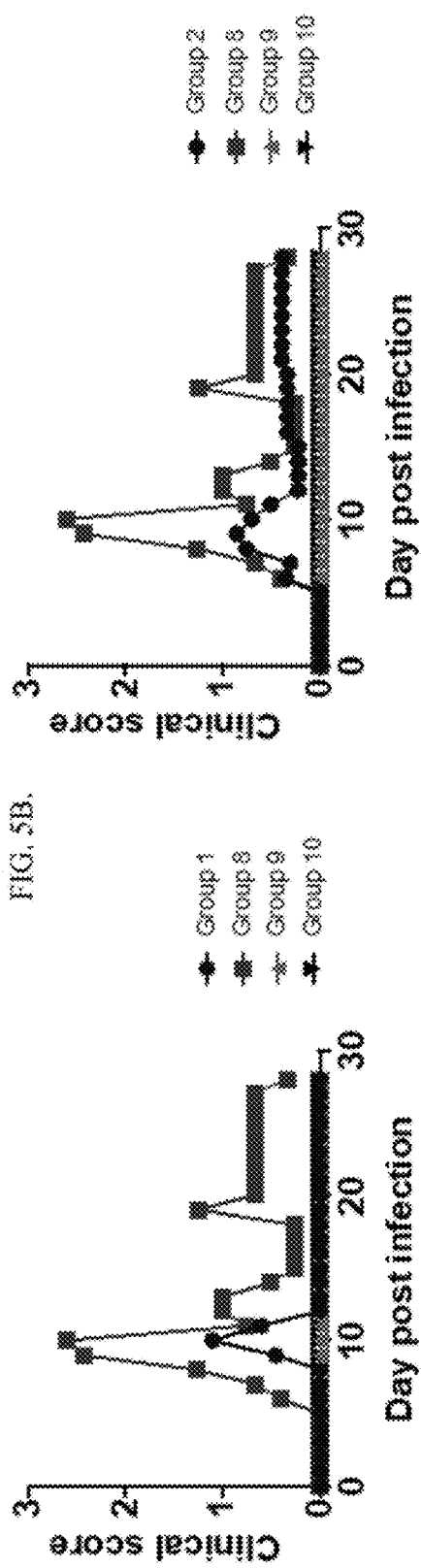
Figure 5D:
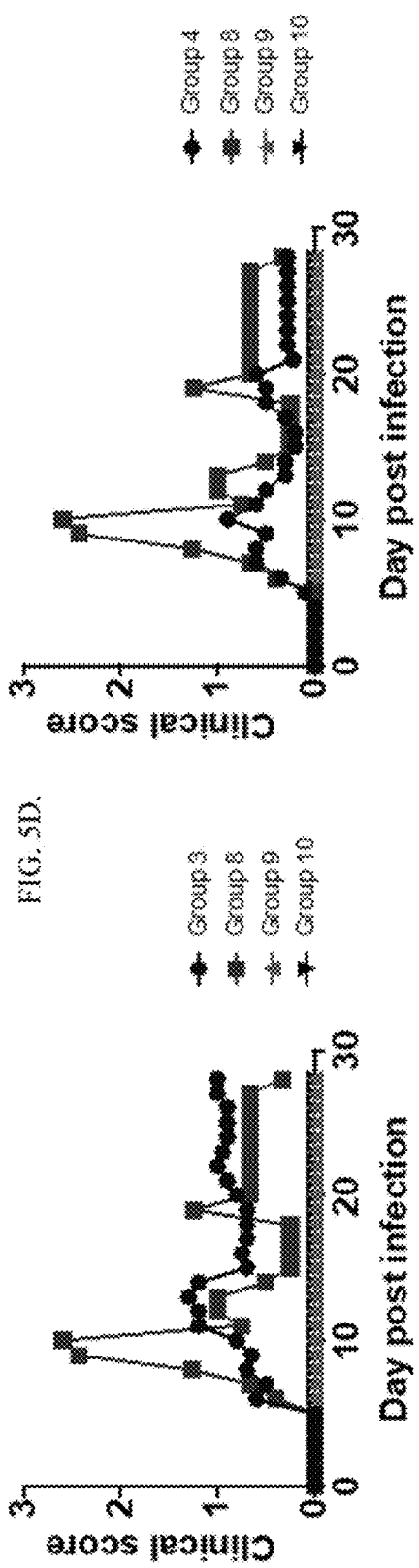

Group 10 mock treated and mock infected control mice and group 9 mock infected compound treated control mice maintained or gained body weight throughout the study (FIG. 4A, Table 3). HSV-2 infected mock treated control mice began to lose weight on day 7 (FIG. 4A, Table 3) through day 10, then as a group they recovered. It is important to point out that only 4 of 15 mice remained at day 11.

Mice infected with HSV-2 and treated with lower doses of compounds A and B (Groups 3 and 4) or compound A only (Group 1) or compound B only (Group 2) had a similar weight loss pattern as group 8 mice, HSV-2 infection control mice (Figure FIG. 4B-4E, Table 2 and 3).

Group 5 mice experienced some weight loss around day 15 but recovered. Mouse number 45 had a sudden loss of body weight starting on day 27. The mouse dropped from 20.4 g to 16.8 g in 2 days. The mouse died prior to euthanasia (FIG. 4F and Table 2).

Group 6 and 7 mice had minimal weight changes throughout the study (FIGS. 4G-4H and Table 2).

Vaginal Lesions and Clinical Scores.

The point system used for clinical scoring can be found in table 4. All HSV-2 infected untreated mice (Group 8) had detectable vaginal lesions at some point during the study except for mouse 71 and mouse 80, which is most likely the result of less virus entering the vaginal tissue during inoculation. Most mice had severe ulceration and paralysis leading to euthanasia (FIG. 5).

Mice infected with HSV-2 and treated with lower doses of compounds A and B (Groups 3 and 4) or compound A only (Group 1) or compound B only (Group 2) had a similar pattern of clinical score, although lower clinical scores overall (FIG. 5). Mice infected with HSV-2 and treated with higher doses of compounds A and B had no clinical scores and are described in Table 4 (FIG. 6).

Clinical scores of mice in group 3 were higher than all other groups of mice (FIG. 7). Group 3 mice were administered the lowest doses of both compound A and compound B. By 2-way ANOVA, group 3 clinical score was significantly different than all other groups of infected and treated mice ($p<0.0001$).

Hair Loss Score

Some mice had only hair loss without a clinical score. A hair loss scoring system was developed (Table 5). FIG. 8 represents hair loss scores. Only mice from group 7 did not have any clinical signs nor hair loss following HSV-2 infection.

Illness Score

The illness scoring system is described in Table 6. The most common illness was ruffled fur. In general, mice infected with HSV-2 and treated with lower doses of compounds A and B (Groups 3 and 4) or compound A only (Group 1) or compound B only (Group 2) had a similar pattern of illness score as control infected mice (FIG. 9). Group 5 treated and infected mice had an early illness score (ruffled fur) then recovered. Group 5 had a second round of illness score that correlated with group 9 treatment control mice. Group 6 and 7 had ruffled fur throughout the study including prior to infection (FIG. 10). Group 6 had mild ruffling whereas group 7 had major ruffling.

Overall mice that had a clinical score, hair loss and/or an illness score is summarized in table 7.

TABLE 7

Overview of Survival, Clinical, Hair Loss, and Illness Scores

| | Group | | | | | | | | | |
|---|---|---|---|---|---|---|---|---|---|---|
| | 1 | 2 | 3 | 4 | 5 | 6 | 7 | 8 | 9 | 10 |
| Survival | 10/10 | 9/10 | 10/10 | 9/10 | 9/10 | 10/10 | 10/10 | 3/15 | 10/10 | 10/10 |
| Clinical | 5/10 | 8/10 | 10/10 | 9/10 | 1/10 | 0/10 | 0/10 | 13/15 | 0/10 | 0/10 |

TABLE 7-continued

Overview of Survival, Clinical, Hair Loss, and Illness Scores

| | Group | | | | | | | | | |
|---|---|---|---|---|---|---|---|---|---|---|
| | 1 | 2 | 3 | 4 | 5 | 6 | 7 | 8 | 9 | 10 |
| Hair loss | 8/10 | 6/10 | 5/10 | 6/10 | 8/10 | 2/10 | 0/10 | 2/15[a] | 0/10 | 0/10 |
| Illness | 10/10 | 9/10 | 9/10 | 10/10 | 10/10 | 10/10 | 10/10v | 13/15 | 9/10 | 10/10 |

[a] most mice succumbed to infection before hair loss became evident. Of the 4 mice that survived beyond 10 days, 2 of the 4 had hair loss, clinical scores and illness scores.

Treatment Comparisons

Group 5 vs. Group 9.

Both Group 5 and group 9 mice were treated with the same dose of compound A and B (Table 1). Group 5 mice were infected with HSV-2 and group 9 mice were mock infected. Beginning at day 4 post infection, group 5 had a significant reduction of body weight as compared to group 9 and this difference remained throughout the remainder of the study (FIG. 4F).

Both group 5 and group 9 had ruffled fur towards the end of the study as well. (FIG. 10A). Neither group 5 or 9 had significant clinical scores.

Group 5 vs. Group 1 and 2.

Group 5 mice were treated with the same dose of compound A as group 1 mice. Group 5 mice were also treated with the same dose of compound B as group 2 mice. Group 1 mice were only treated with compound A and group 2 mice were only treated with compound B (Table 1).

Figure 11:
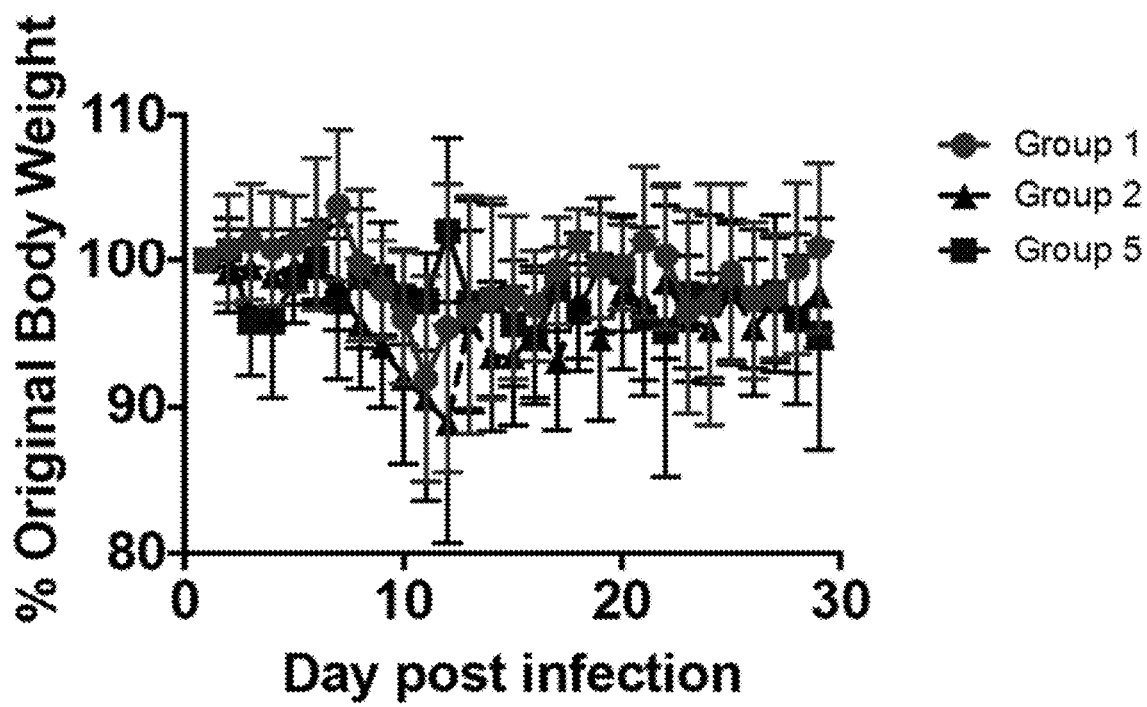
FIG. 11. Body weight is shown post infection as % of original body weight for groups 1 and 2 as compared to 5. Group 1 mice were treated daily with 125 mg/kg Valacyclovir. Group 2 mice were treated with 63 mg/kg of Famciclovir daily. Group 5 mice were treated with 125 mg/kg Valacyclovir and 63 mg/kg of Famciclovir daily. All drugs were administered by oral gavage beginning 7 days prior to HSV-2 infection. Mice were weighed daily during infection and the % original body weight calculated.
Figure 12:
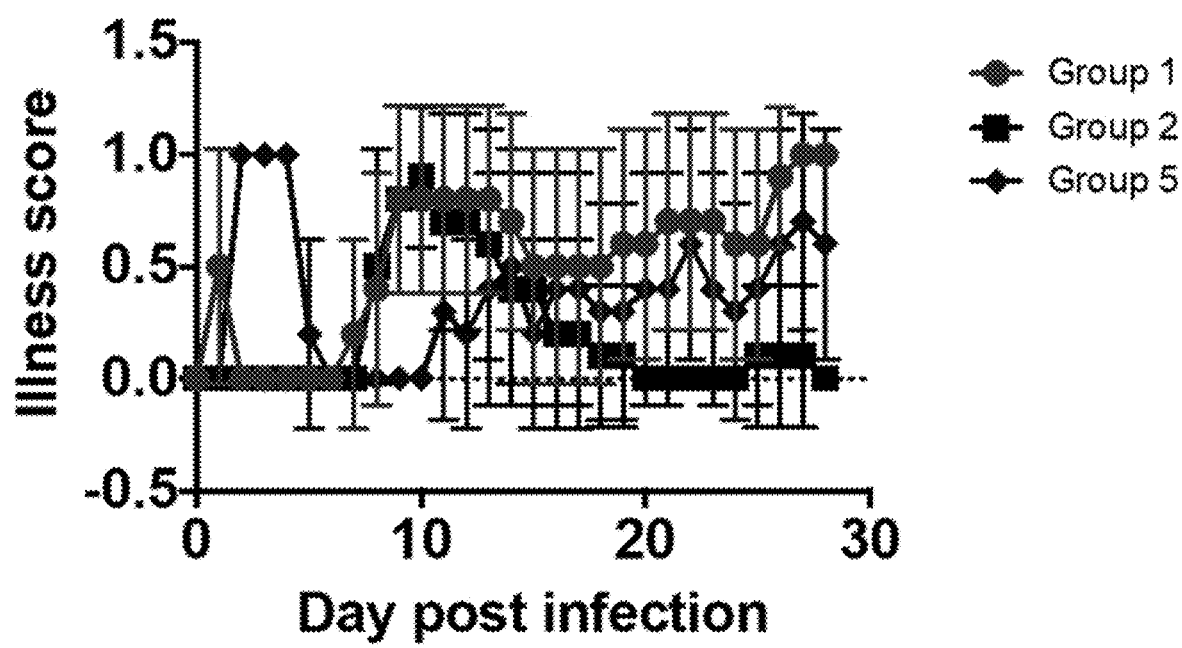
FIG. 12. Illness score following infection with HSV-2, groups 1, 2 and 5. Mice were treated with different doses of compound(s) and infected with HSV-2. Illness scores were recorded daily using a 4-point system (Table 6): 0=healthy, 1+ ruffled fur, 2+ arched back, 3+ lethargic to touch, and 4+ paralysis of one or both hind limbs.
Figure 13:
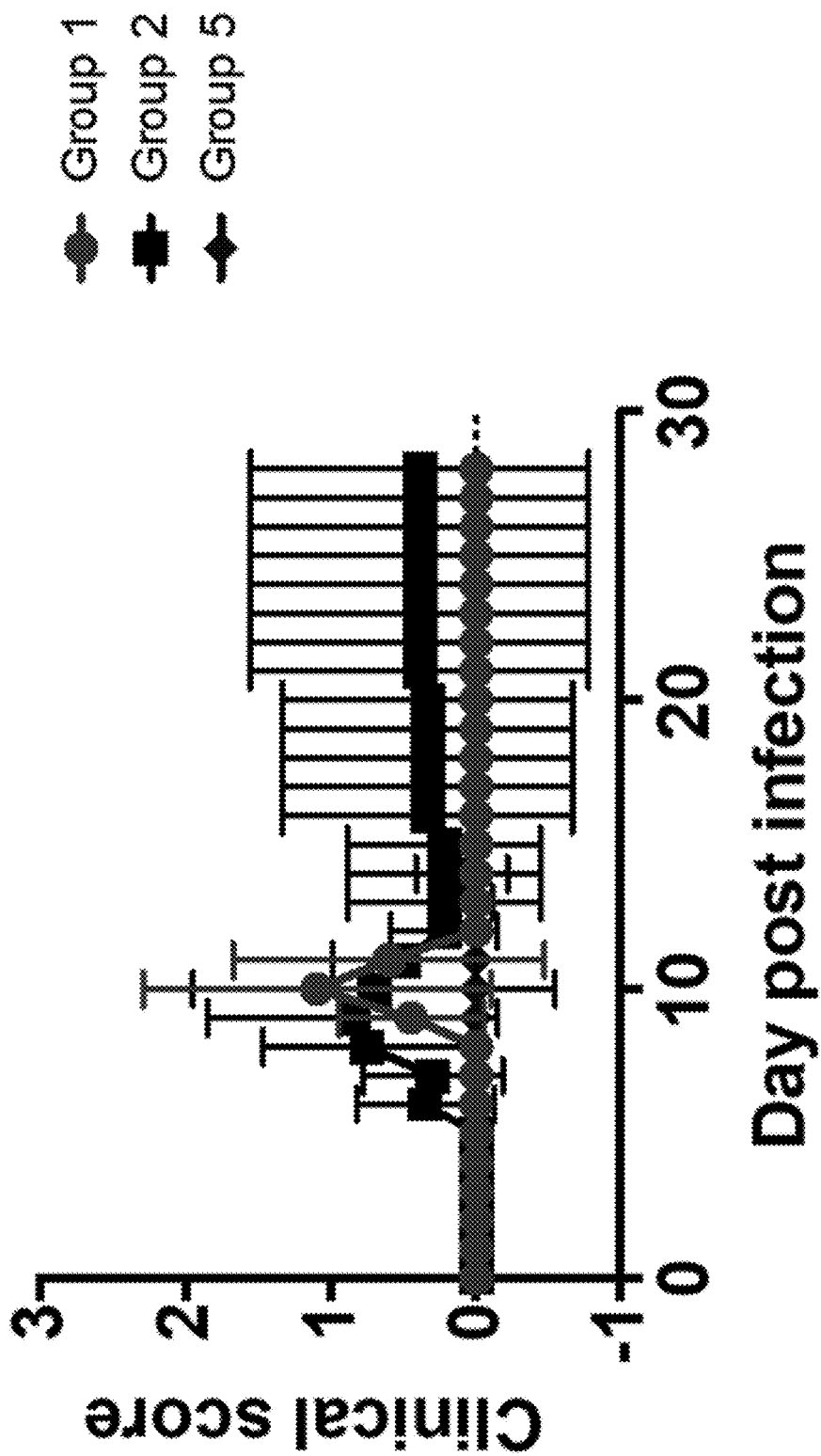
FIG. 13. Clinical score group 1, 2 and 5. Mice were monitored daily following infection for vaginal clinical scores using a 4-point system (table 2): 0=no disease, 1+ redness or swelling (genital erythema), 2+a few small vesicles (moderate genital infection), 3+ purulent genital ulceration, hair loss, poor condition, and 4+ severe ulcerations with maceration, hind limb paralysis (leading to euthanasia).

Overall, there was a significant increase in the body weight of group 5 as compared to group 2 (FIG. 11) between days 10-12 post infection ($p=0.0193$, $p=0.0151$ and $p=0.0009$ respectively, student t test). There was a significant increase in illness score in Group 5 mice as compared to Group 2 mice between days 10-13 post infection (FIG. 12, $p=0.00001$, $p=0.00001$, $p=0.02$ and $p=0.005$ respectively, student t test). There was a significant decrease in clinical score in Group 5 mice as compared to Group 1 mice between days 10-11 post infection (FIG. 13, $p=0.01$, $p=0.009$). There was a significant decrease in clinical score in Group 5 mice as compared to Group 1 mice between days 9, 10 and 12 post infection (FIG. 13, $p=0.003$ and $p=0.015$ and $p=0.006$ respectively, student t test).

EC50, EC90 Dose Response and Combination Index.

Figure 14A:
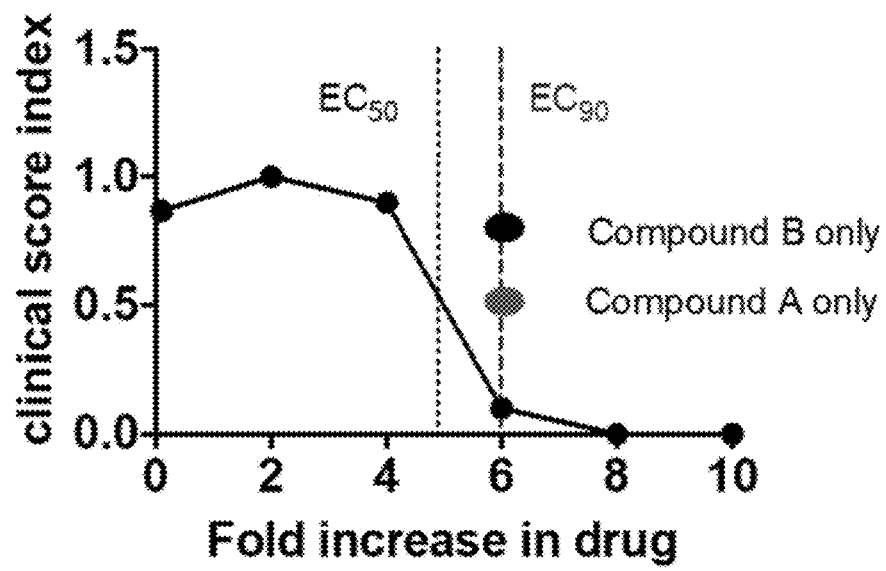
FIG. 14A-14B. EC50 and EC90 determination. (A) EC50 and EC90 clinical score calculation. Mice that were treated with 2-fold different dose combinations of drug A and B were analyzed as compared to mock treated controls (0). The EC50 was calculated to be 4.898 and the EC90 was 5.98-fold of drug. The black dot indicates the clinical score of group 2, compound B only at the 6-fold drug dose and the green dot indicates the clinical index of Group 1 treated with compound A drug only at the 6 fold drug dose. (B) EC50 and EC90 survival calculation. Mice that were treated with 2-fold different dose combinations of drug A and B were analyzed as compared to mock treated controls (0). The EC50 was calculated to be 0.7689 and the EC90 was 2.3-fold of drug.
Figure 14B:
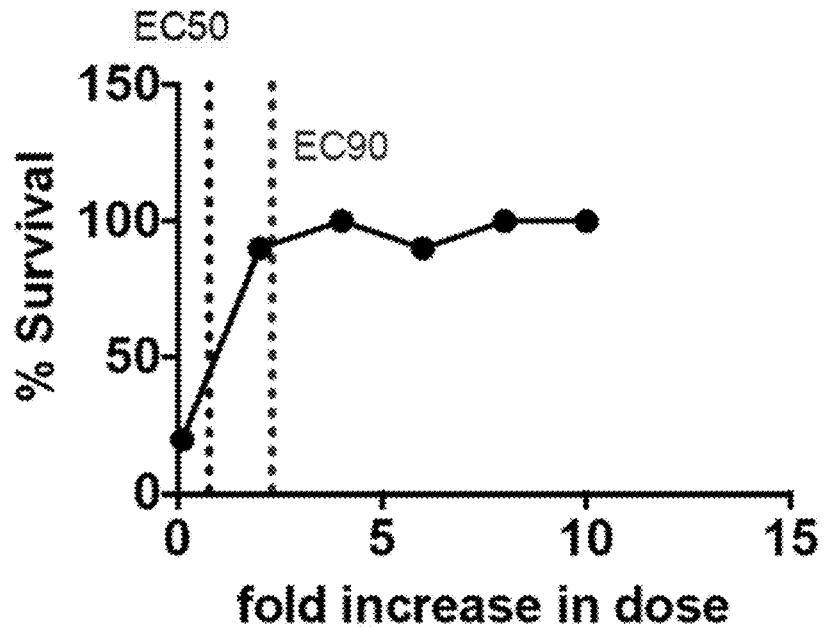

Clinical scores were used to determine the EC50, EC90 (FIG. 14A), and the dose response curve (FIG. 14B). The EC50 was calculated to be 4.898 and the EC90 5.98. These numbers correlate to the fold increase in compound A and compound B. In addition, the dose response curve comparing clinical score to dose is significant $p=0.0215$ (FIG. 14B). Finally, the combination index of Group 1 and 2 as compared to group 5 was 0.2 which is significant.

A clinical score index was generated for each group based on how many mice in each group had a clinical score throughout the study (table 7). The indexes for each group were as follows: Group 1 (A alone): 0.5; Group 2 (B alone): 0.8; Group 3 (0.25× A, 0.25× B): 1.0; Group 4 (0.5× A, 0.5× B): 0.9; Group 5 1× A, 1× B): 0.1; Group 6 (2× A, 2× B): 0; Group 7 (4× A, 4× B): 0; Group 8 (no treatment): 0.867; Group 9 (1× A, 1× B, uninfected): 0; Group 10 (untreated, uninfected): 0.

To calculate the EC50, the clinical score index was compared to the 2-fold increase in both compound A and compound B in groups 3 to 7 with group 8 being the no drug control (FIG. 14A). The dose increase of drug was transformed to the log scale and the clinical index was transformed. The EC50 was calculated using nonlinear regression (curve fit) with $\log(x)$ vs. normalized y and a variable slope and the extra sum of squares F test comparison method. The EC50 was determined to be 4.898 which means a 4.898-fold increase in drugs A and B (FIG. 14A). The EC90 was calculated using prism graphpad software calculator using the EC50 and its hill slope. The EC90 is 5.98.

The $EC_{50}$ and $EC_{90}$ of the group survival was also calculated. The percent survival of each group treated with both compound A and compound B were plotted and the $EC_{50}$ and CD90 were calculated as described above (FIG. 14B). The $EC_{50}$ is 0.7689 and the $EC_{90}$ is 2.3067.

Figure 15A:
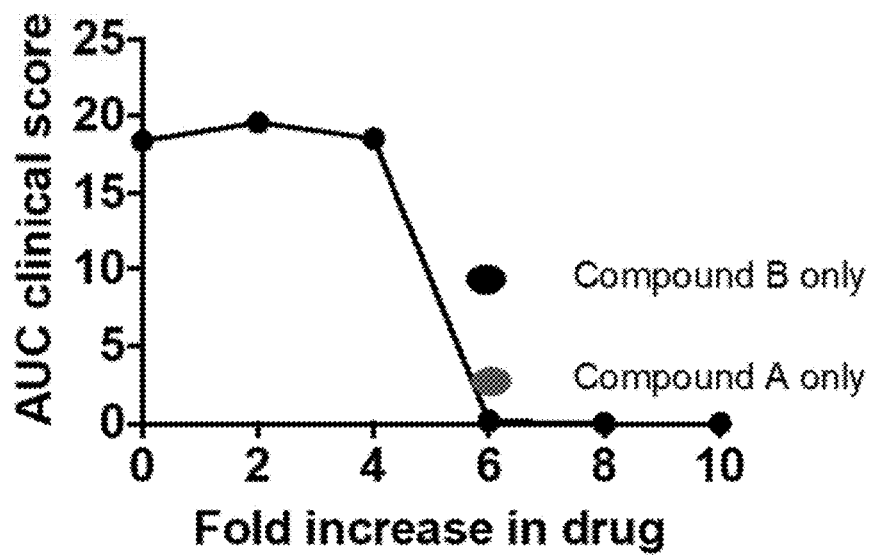
FIG. 15A-15B. Clinical score dose response. (A) Combinations of drug A and B. Mice that were treated with 2-fold different dose combinations of drug A and B were analyzed as compared to mock treated controls (0). The area under the curve for each group's clinical score was calculated then plotted. The black dot indicates the clinical score of group 2, compound B only at the 6-fold drug dose and the green dot indicates the clinical index of Group 1 treated with compound A drug only at the 6-fold drug dose. The correlation was significant between clinical score and drug dose $p=0.0215$. (B) Single drug as compared to drug combination. Mice were treated with either B, Famciclovir or A, Valacyclovir or both A and B. The area under the curve for each group clinical score was calculated then plotted.

To determine the clinical score dose response curve, the area under the curve was calculated for each treatment group and plotted (FIG. 14B). The correlation between clinical score and dose was significant ($p=0.0215$). The clinical score dose response for groups 1 (compound A only), group 2 (compound B only) or group 5 (both compound A and compound B) was not significant (FIG. 15A).

The Combination Index is defined as 1=additive, <1=synergy, >1 antagonistic. The combination index was measured by comparing group 1 and 2 with group 5 using the following formula:

$CI=AB/(A+B)$ where $A$ is drug $A$ compared to the control and $B$ is drug $B$ compared to the control and $AB$ is drug $AB$ as compared to the control.

$CI=(0.1/0.8667)/[(0.5/0.8670)\times(0.8/0.867)]$ $CI=0.2$

If the CDI is less than 1 then there is synergy between the drugs. Since the CDI is 0.2, the synergy is significant.

Therapeutic Index

Figure 15B:
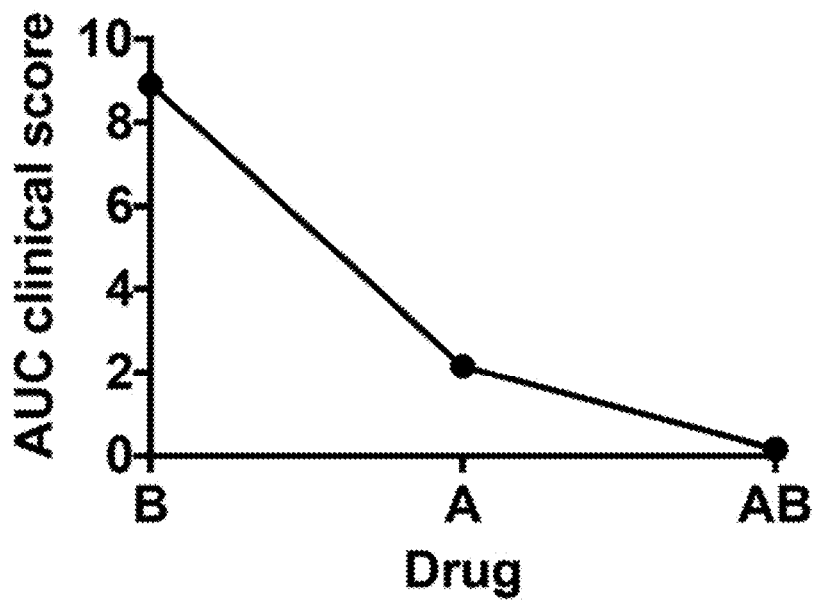
Figure 16:
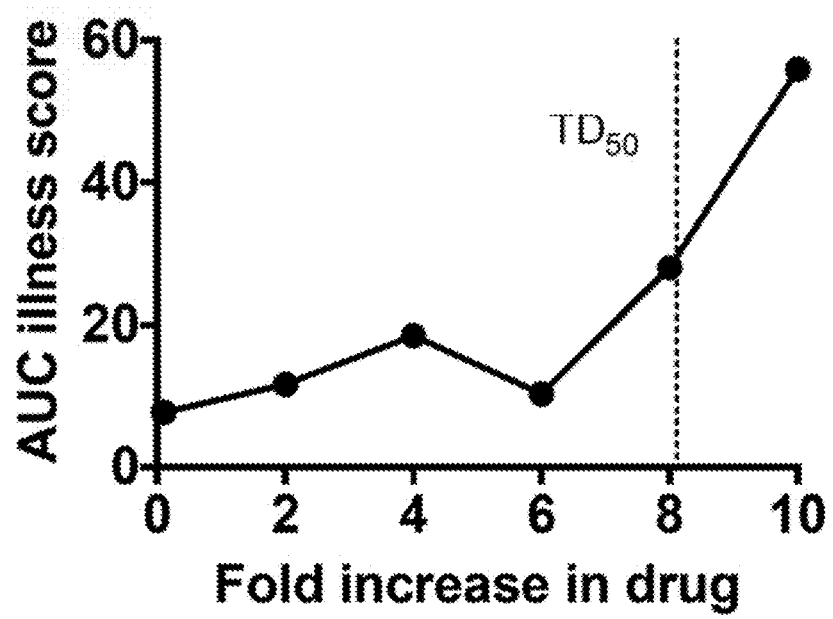
FIG. 16. Area under the curve (AUC) of illness score after infection. Mice that were treated with 2-fold different dose combinations of drug A and B were analyzed as compared to mock treated controls (0). The area under the curve for each group clinical score was calculated then plotted. The TD50 (toxic dose) was calculated to be 8.113.

Usually the therapeutic index in animal studies is calculated using the drug concentration that causes 50% of the animals to succumb to the toxic effects (lethal dose $LD_{50}$) to the effective dose ($ED_{50}$). In this study, the drug had no lethality. It did cause ruffled fur as an illness. Therefore, instead of the $LD_{50}$ we used the toxic dose 50 or $TD_{50}$ to calculate the therapeutic index (FIG. 15B). The $TD_{50}$ was found to be 8.113. This is the AUC illness score post infection. The $EC_{50}$ for clinical score was 4.898. The formula for therapeutic index is: $TI=TD_{50}/EC_{50}=8.113/4.898=1.659$. Note that the $TD_{50}$ prior to infection was calculate to be 8.0 meaning an 8-fold increase in the drug caused ruffling of the fur. The $EC_{50}$ for survival was 0.7689. Therefore the $TI=8.113/0.7689=10.55$.

Overall, antiviral treatment of HSV-2 infected mice according to the invention resulted in protection of mice from mortality (FIGS. 2 and 3). In addition, mice treated with high doses of drugs (group 5-7) had significantly reduced clinical scores. Mice treated with the highest dose of the drugs (group 7) had no clinical signs of disease, however, they did have ruffled fur throughout the study, including pre-infection suggesting a degree of drug toxicity (FIG. 10 and Table 7). Mice in group 6 also had some drug related toxicity (FIG. 10) and hair loss associated with the infection (FIG. 8 and Table 7). Mice in group 9 were treated with an intermediated dose of drug and not infected. The mice had some ruffling towards the end of the study suggesting possible drug toxicity build-up (FIG. 10 and Table 7). Group 5 mice that received the same dose of drug as group 9 but were infected with HSV-2 had only hair loss as a clinical endpoint and ruffled fur (FIGS. 8, 10 and Table 7). The mice treated with the lowest amount of drug, group 3, had the highest clinical score of all treated groups (FIG. 7). The clinical score of group 3 mice were higher than mice treated with compound A alone or compound B alone and this was significant.

The $EC_{50}$ for clinical score was 4.898 which correlates to 78.24 mg/kg A and 39.184 mg/kg B. The $EC_{90}$ was 5.98 which correlates to 95.68 mg/kg A and 47.84 mg/kg B. The $EC_{50}$ for survival was 0.7689 which correlates to 12 mg/kg A and 6.15 mg/kg of compound B. There was also synergy between compounds A and B in that the combination index of drug A and drug B alone as compared to a combination of drug A and drug B was significant at 0.2.

Since there was no drug induced mortality, the therapeutic index (TI) was calculated by comparing the area under the curve of the illness for each group to determine the toxic dose 50 ($TD_{50}$). The $TD_{50}/EC_{50}$ was 1.659 and is a low therapeutic index indicating that a small change in the drug led to ruffled fur in the mice. When using the survival $EC_{50}$, the TI was 10.55. Note however, that the usual calculation for TI includes an $LD_{50}$ comparison instead of the $TD_{50}$, however a dose that would cause lethality by the drug was not determined in this study.

Treatment of mice with antiviral compounds did not prevent infection in all groups of mice since some treated mice had a loss of body weight, an illness score, and clinical scores. However, treatment did successfully prevent mortality associated with HSV-2 infection. In addition, this study demonstrates that high doses of the compounds protected mice from mortality and clinical symptoms but had an effect on mouse illness symptoms; and low doses of the compounds protected mice from mortality but not all clinical and illness symptoms. There was synergy between compound A and compound B as measured by the combination index.

Example 2: HSV Viral Load

For mice that survived up to 28 days post infection, Dorsal Root Ganglia (DRG) were harvested and stored at −80 C until qPCR could be performed. (Table 2B). Mice were monitored daily by the point system described above (see Table 4). Table 8 shows an analysis of clinical scores.

TABLE 8

| | Clinical Scores | |
|---|---|---|
| Group | Overall Mean | Overall SD |
| Group 1 | 0.07413 | 0.379655802 |
| Group 2 | 0.3125 | 0.8283 |

TABLE 8-continued

| | Clinical Scores | |
|---|---|---|
| Group | Overall Mean | Overall SD |
| Group 3 | 0.71607 | 1.002 |
| Group 4 | 0.31914 | 0.7481 |
| Group 5 | 0.00517 | 0.0656 |
| Group 6 | 0 | 0 |
| Group 7 | 0 | 0 |
| Group 8 | 0.6121 | 1.089 |
| Group 9 | 0 | 0 |
| Group 10 | 0 | 0 |

Figure 17:
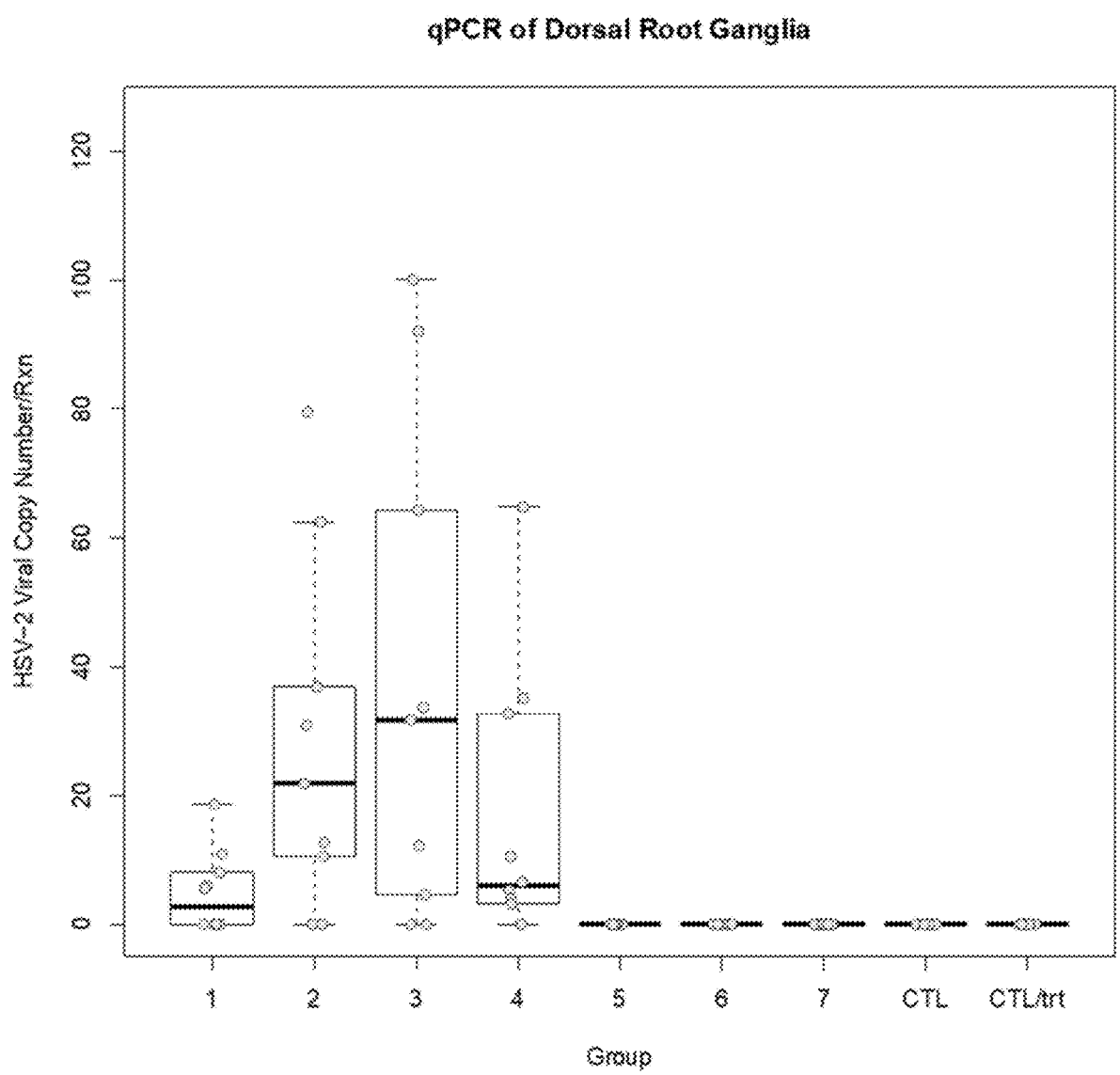
FIG. 17. Copy number of HSV DNA. HSV viral copy number/reaction for Groups 1-10. The lower limit for detection is 3 molecules.
Figure 18:
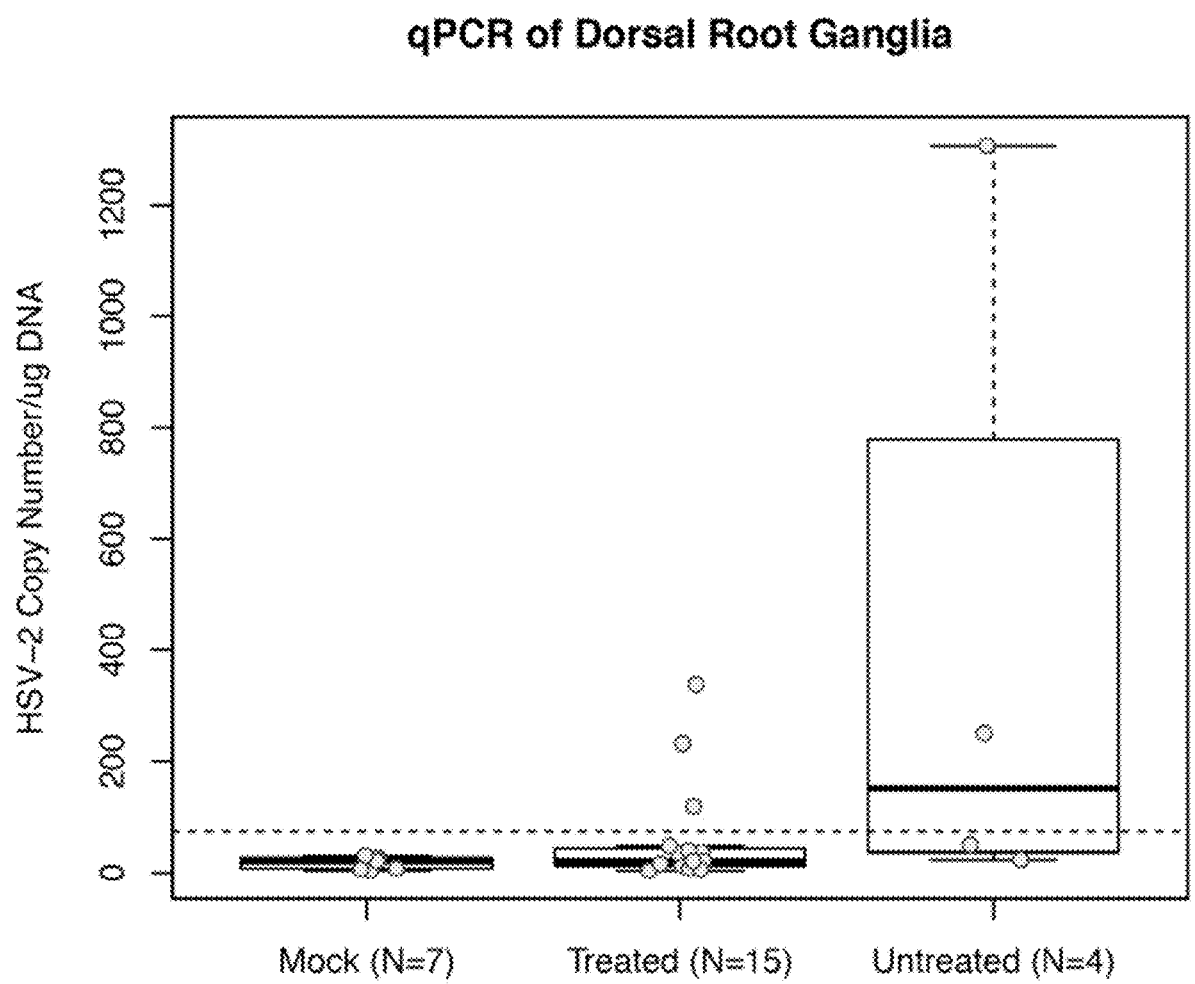
FIG. 18 Copy number of HSV DNA. HSV viral copy number/μg DNA for mock, treated, and untreated, infected animals.

Dorsal Root Ganglia (DRG) were analyzed by qPCR. Table 9 shows average copy number/rxn in the DRG. Group 1 was lower than Group 2, p=0.03 and Group 3, p=0.02. Group 2 was not significantly different than Groups 3 or 4. Groups 5, 6, and 7 were significantly lower than Group 1 or group 2 (P=0.03 for all comparisons). For groups 5-7, every data point was below the limit of detection. Results are plotted as HSV-2 Copy Number/μg DNA (FIG. 17) and HSV-2 Copy Number/rxn (FIG. 18).

TABLE 9

| | qPCR- Copy number/rxn | | |
|---|---|---|---|
| Group | Overall Mean | Overall SD | Number Undetectable <3 |
| Group 1 | 4.92 | 6.3 | 5 |
| Group 2 | 28.32 | 27.55 | 2 |
| Group 3 | 41.26 | 36.54 | 2 |
| Group 4 | 14.4 | 21.72 | 2 |
| Group 5 | 0 | 0 | 10 |
| Group 6 | 0 | 0 | 10 |
| Group 7 | 0 | 0 | 10 |
| Group 8 | ND | ND | ND |
| Group 9 | 0 | 0 | 10 |
| Group 10 | 0 | 0 | 10 |

Example 3: Pharmacokinetic Study of Valacyclovir and Famciclovir Following a Single Dose Administration to Female BALB/C Mice The objective of this study was to determine the plasma pharmacokinetics of Valacyclovir (VACV) and Famciclovir (FCV) in female BALB/c mice alone and in combination, administered by the intravenous (iv) and oral gavage (po) dose routes. Each animal received a single dose of either 1 test article or both at various combinations of dose levels. Animals were administered VACV by iv (Group 1; 125 mg/kg) and po (Groups 2, 4-8; 32-500 mg/kg) routes. Animals were administered FCV by iv (Group 1; 63 mg/kg) and po (Groups 3-8; 16-250 mg/kg) routes. Blood was collected from the treated mice (n=3 mice per group) at 5 (iv), 15, 30 min and 1, 2, 4, 8, 12 (po) and 24 hr post dose for processing to plasma. The 2:1 ratio of valacyclovir:famciclovir was selected as representative of advantageous combination amounts. Efficacious ratios include about 5:1, about 4:1, about 3:1, about 2:1, about 1:1, about 1:2, about 1:3, about 1:4, or about 1:5.

TABLE 10

Experimental Design
Pharmacokinetic Study of Valacyclovir and Famciclovir Following a Single Dose Admnistration to Female BALb/c Mice

| Group | Treatment [a] | Dose Level (mg/kg) [b] | Dose Route | Subgroup | No. of Animals [c] | Blood Collection (hr) [d] |
|---|---|---|---|---|---|---|
| 1 | A + B | 125 (A) + 63 (B) | iv | A | 3 | 0.083, 1 |
|   |       |                  |    | B | 3 | 0.25, 4 |
|   |       |                  |    | C | 3 | 0.5, 8 |
|   |       |                  |    | D | 3 | 2, 24 |
| 2 | A | 125 (A) | po | A | 3 | 1, 24 |
|   |   |         |    | B | 3 | 0.25, 4 |
|   |   |         |    | C | 3 | 0.5, 8 |
|   |   |         |    | D | 3 | 2, 12 |
| 3 | B | 63 (B) | po | A | 3 | 1, 24 |
|   |   |        |    | B | 3 | 0.25, 4 |
|   |   |        |    | C | 3 | 0.5, 8 |
|   |   |        |    | D | 3 | 2, 12 |
| 4 | A + B | 32 (A) + 16 (B) | po | A | 3 | 1, 24 |
|   |       |                 |    | B | 3 | 0.25, 4 |
|   |       |                 |    | C | 3 | 0.5, 8 |
|   |       |                 |    | D | 3 | 2, 12 |
| 5 | A + B | 63 (A) + 32 (B) | po | A | 3 | 1, 24 |
|   |       |                 |    | B | 3 | 0.25, 4 |
|   |       |                 |    | C | 3 | 0.5, 8 |
|   |       |                 |    | D | 3 | 2, 12 |
| 6 | A + B | 125 (A) + 63 (B) | po | A | 3 | 1, 24 |
|   |       |                  |    | B | 3 | 0.25, 4 |
|   |       |                  |    | C | 3 | 0.5, 8 |
|   |       |                  |    | D | 3 | 2, 12 |
| 7 | A + B | 250 (A) + 125 (B) | po | A | 3 | 1, 24 |
|   |       |                   |    | B | 3 | 0.25, 4 |
|   |       |                   |    | C | 3 | 0.5, 8 |
|   |       |                   |    | D | 3 | 2, 12 |
| 8 | A + B | 500 (A) + 225 (B) | po | A | 3 | 1, 24 |
|   |       |                   |    | B | 3 | 0.25, 4 |
|   |       |                   |    | C | 3 | 0.5, 8 |
|   |       |                   |    | D | 3 | 2, 12 |

[a] A = Valacyclovir (VACV); B = Famciclovir (FCV).
[b] The dose level and dose concentration were prepared using the free base molecular weight; VACV used a correction factor of 1.11.
[c] Plasma was collected from 3 additional untreated female mice for baseline control samples.
[d] Two blood samples were collected from each mouse.

Results

Clinical observations were performed immediately post-dose and prior to the last blood collection and are summarized in Table 11. At 63 mg/kg FCV (Group 3) one animal exhibited ruffled fur and another animal died during its first blood collection (animal was not replaced). At 63 mg/kg VACV/32 mg/kg FCV (Group 5), 2 animals were squinting on Day 1, and at 125 VACV/63 mg/kg FCV (Group 6) one mouse was squinting on Day 1. At 250 mg/kg VACV/125 mg/kg FCV (Group 7), one mouse showed ruffled fur on Day 2, and 2 mice were squinting on Day 1. At 500 mg/kg VACV/250 FCV (Group 8), one animal was hypoactive, one animal demonstrated shoveling, and 3 mice were squinting on Day 1. All other treated mice appeared normal throughout the study.

TABLE 11

Clinical Observations
Pharmacokinetic Study of Valacyclovir and Famciclovir Following a Single Dose Admnistration to Female BALb/c Mice

| Group | 1 | 2 | 3 | 4 | 5 | 6 | 7 | 8 |
|---|---|---|---|---|---|---|---|---|
| Treatment: | | | | | | | | |
| Valcyclovir (mg/kg) | 125 | 125 |    | 32 | 63 | 125 | 250 | 500 |
| Famcyclovir (mg/kg) | 63  |     | 63 | 16 | 32 | 63  | 125 | 200 |
| Dose Route | iv | po | po | po | po | po | po | po |
| Observations: | | | | | | | | |
| Normal | 12 | 12 | 12 | 12 | 12 | 11 | 10 | 10 |
| Hypoactivity | 0 | 0 | 0 | 0 | 0 | 0 | 0 | 1 |
| Ruffled Fur | 0 | 0 | 1 | 0 | 0 | 0 | 1 | 0 |
| Shoveling | 0 | 0 | 0 | 0 | 0 | 0 | 0 | 1 |

TABLE 11-continued

Clinical Observations
Pharmacokinetic Study of Valacyclovir
and Famciclovir Following a Single Dose
Admnistration to Female BALb/c Mice

| Group | 1 | 2 | 3 | 4 | 5 | 6 | 7 | 8 |
|---|---|---|---|---|---|---|---|---|
| Squinting | 0 | 0 | 0 | 0 | 2 | 1 | 2 | 3 |
| Dead | 0 | 0 | 1 | 0 | 0 | 0 | 0 | 0 |

Plasma Drug Levels

Figure 19:
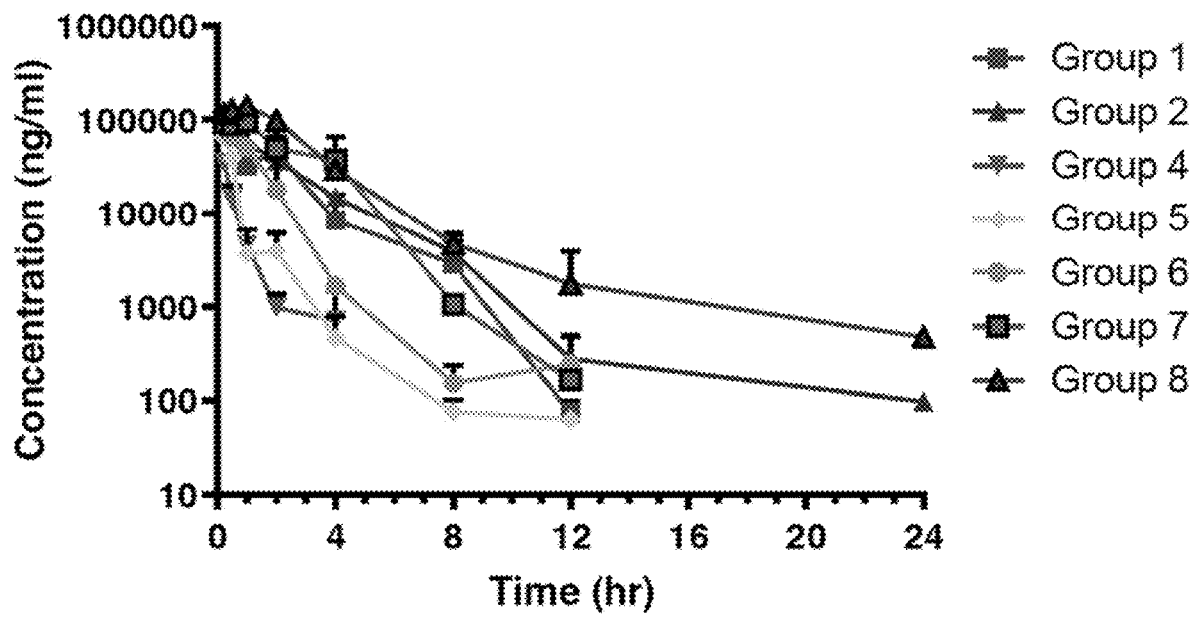
FIG. 19. Plasma concentrations of VACV-equiv in female BALB/c mice. Animals were administered VACV by iv (Group 1; 125 mg/kg) and po (Groups 2, 4-8; 32-500 mg/kg) routes. The quantity of VACV-equiv represents the total of VLAC plus the metabolite, ACV.
Figure 20:
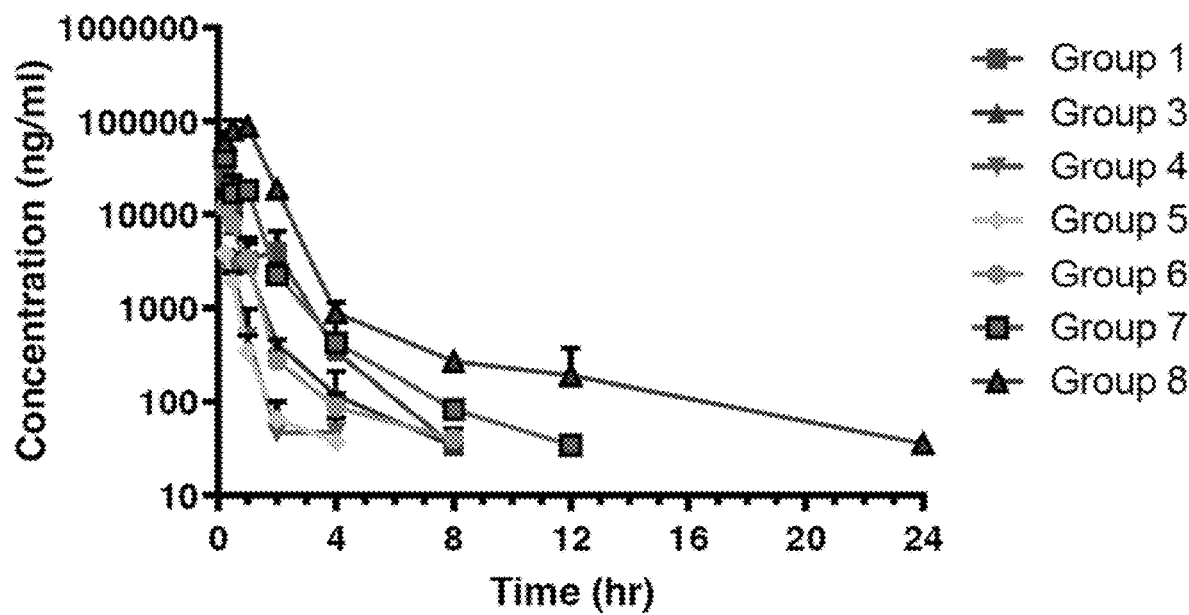
FIG. 20. Plasma concentrations of FCV-equiv in female BALB/c mice. Animals were administered FCV by iv (Group 1; 63 mg/kg) and po (Groups 3-8; 16-250 mg/kg) routes.
Figure 21:
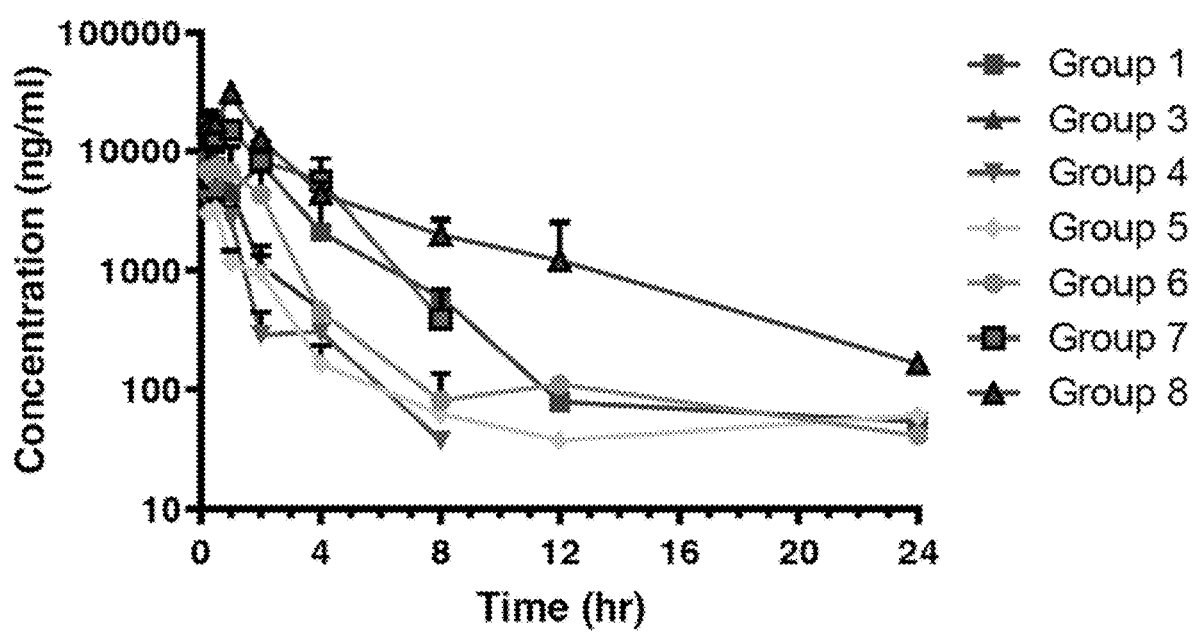
FIG. 21. Plasma concentrations of PCV in female BALB/c mice. Animals were administered FCV by iv (Group 1; 63 mg/kg) and po (Groups 3-8; 16-250 mg/kg) routes. PCV, a metabolite of FCV, was measured in plasma.

The plasma concentrations of VACV-equivalent (representing the total of VACV and ACV) are presented in FIG. 19. FIGS. 20 and 21 present the plasma concentrations of FCV-equivalent and PCV, respectively.

FIG. 19 shows that VACV-equivalent was measurable in plasma samples through 24 hr in Group 2 (VACV, 125 mg/kg po) and Group 8 (VACV, 500 mg/kg and FCV, 250 mg/kg). Group 3 had quantifiable concentrations of VACV-equivalent through 4 hr and the other groups had concentrations above the LLOQ through 12 hr. FIG. 20 shows that plasma concentrations of FCV-equivalent tended to increase with the dose administered. PCV (FIG. 21), a metabolite of FCV, was quantifiable in at least 1 of 3 mice through 24 hr in Groups 1, 5, and 8.

Pharmacokinetics Analysis

Table 12 summarizes the pharmacokinetic parameters for VACV-equivalent, FCV-equivalent, and PCV after administration of VACV or FCV, singly or in combination. Plasma concentrations of VACV-equivalents and FCV-equivalents were determined and the lower limit of quantitation (LLOQ) for the assays were 50 ng/ml for VACV-equivalents and penciclovir (PCV), and 25 mg/ml for FCV-equivalents. These data were used to calculate the pharmacokinetic parameters for VACV-equivalents, FVC-equivalents, and PCV. Group 1 was administered 125 mg/kg VACV and 63 mg/kg FCV by the iv route. The $t_{1/2}$ value for the combination of VACV-equivalent was 0.79 hr. The $t_{1/2}$ values for FCV-equivalent and its metabolite PCV were 0.49 and 1.29, respectively. The highest $C_{max}$ after iv administration was for VACV-equivalent (92267 ng/ml), followed by FCV-equivalent (25433 ng/ml) and PCV (8797 ng/ml). Systemic exposure to the test article and metabolites after iv administration, based on $AUC_{last}$ varied as follows: VACV-equivalent, 98626±17114 hr·ng/ml>PCV, 15055±2598 hr·ng/ml>FCV-equivalents, 11949±2007 hr·ng/ml.

The test articles were administered orally (po) in Group 2, 125 mg/kg VACV, and Group 3, 63 mg/kg FCV. In Group 2, VACV-equivalent reached peak plasma concentrations at the $T_{max}$ of 0.25 hr, with maximum plasma concentration ($C_{max}$) of 85000±3459 ng/ml. The elimination phase half-life ($t_{1/2}$) was 2.83 hr for VACV-equivalent. The area under the plasma concentration with time curve to the last time point ($AUC_{last}$) was 208370±22333 hr·ng/ml. The $T_{max}$ values for FCV-equivalent and PCV in Group 3 were 0.25 hr, with $C_{max}$ values of 12433±1671 ng/ml and 8120±565 ng/ml, respectively. $AUC_{last}$ values were slightly lower for FCV-equivalent than for its metabolite: PCV, 9257±704 hr·ng/ml (FCV) and 10609±727 hr·ng/ml (PCV). The $t_{1/2}$ was 1.72 hr for FCV-equivalent and 0.97 hr for PCV.

Mice in Groups 4-8 received the two test articles in combination. The doses ranged from 32 mg/kg to 500 mg/kg for VACV and from 16 mg/kg to 250 mg/kg for FCV. The $t_{1/2}$ values in these groups, except the highest dose group, were in the range of 1 to 3 hr. In Group 8, the $t_{1/2}$ values for FCV-equivalent and PCV were 4.59 hr and 4.30 hr, respectively. This longer $t_{1/2}$ suggests that at the higher dose of FCV, changes in absorption and possible saturation of mentalism to PCV may have impacted exposure to the test article, FCV and its metabolites.

Figure 22:
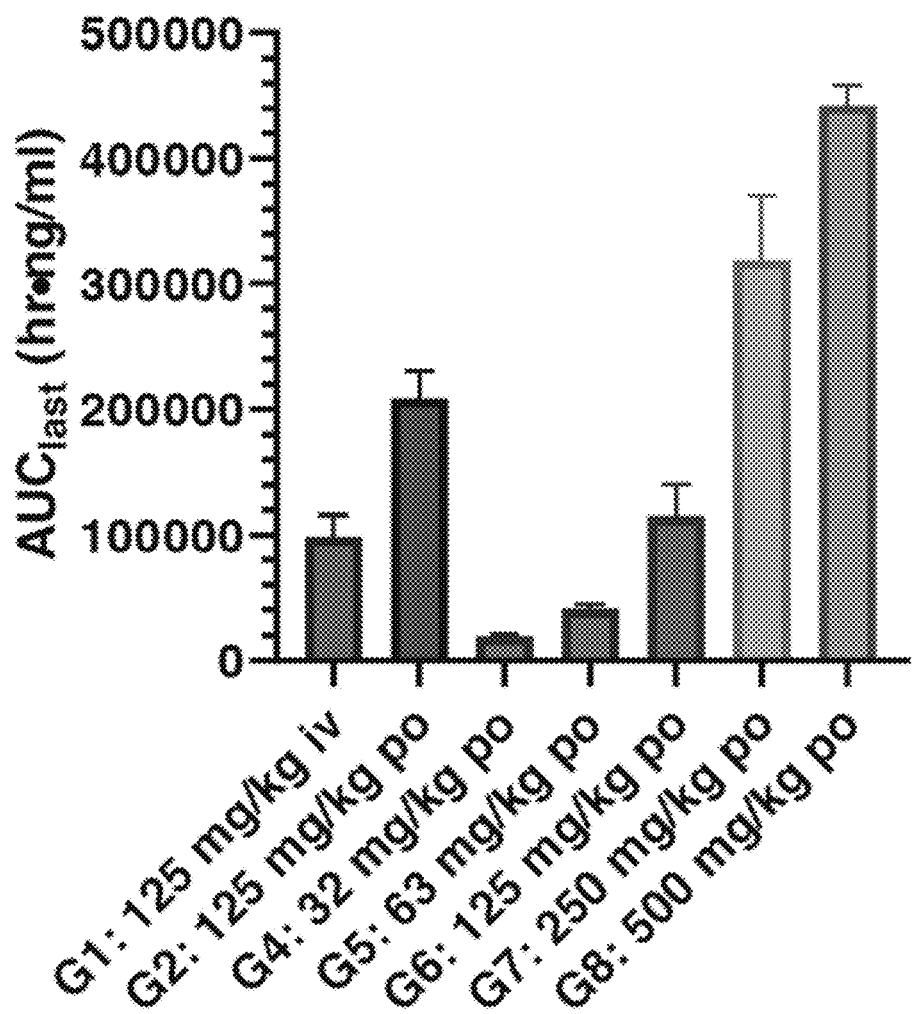
FIG. 22. $AUC_{last}$ values for VACV-equiv, representing the concentrations of both VACV and its metabolite ACV in female BALB/c mice. The doses of VACV administered to the mice in each group are indicated in the graph. For Group 1, VACV, 125 mg/kg, was co-administered with FCV by the iv route. Group 2 was administered VACV only by po route. Groups 4-8 were administered VACV and FCV in combination by the po route.
Figure 23:
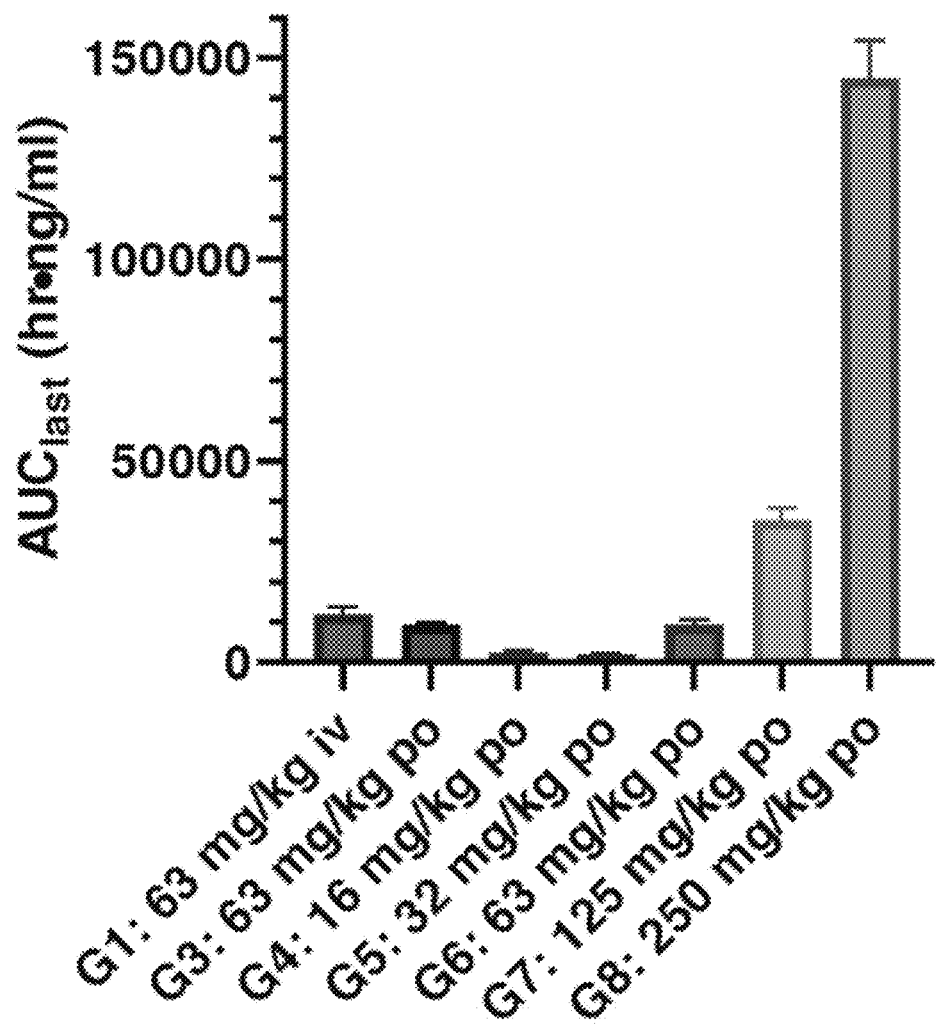
FIG. 23. $AUC_{last}$ values for FCV-equiv in female BALB/c mice. The doses of FCV administered to the mice in each group are indicated in the graph. For Group 1, FCV, 63 mg/kg, was co-administered with VACV by the iv route. Group 3 was administered FCV only by po route. Groups 4-8 were administered VACV and FCV in combination by the po route.
Figure 24:
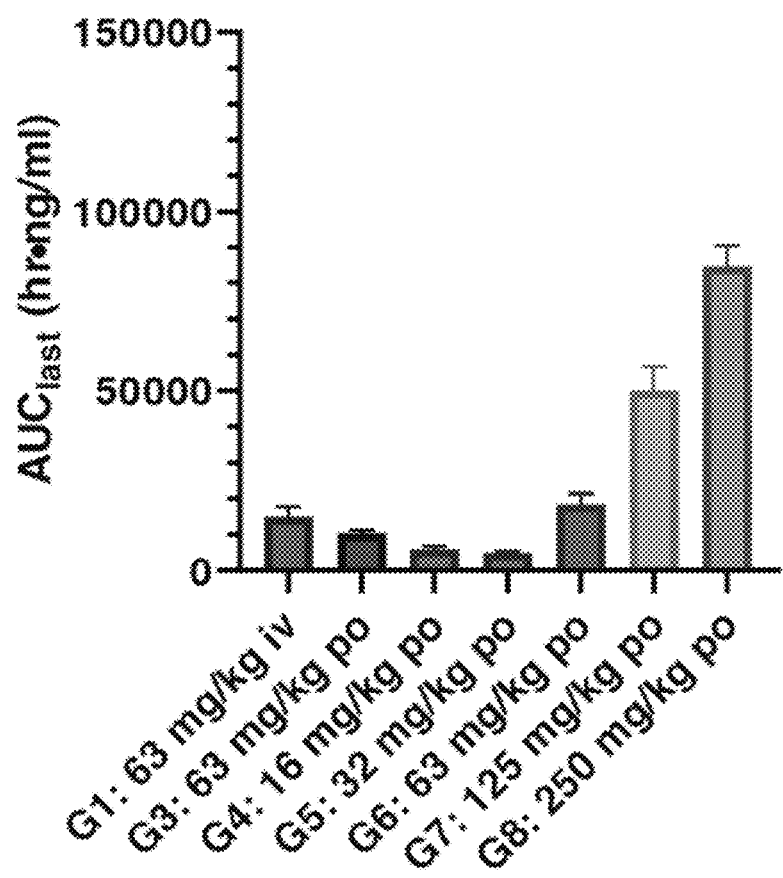
FIG. 24. $AUC_{last}$ values for PCV, the metabolite of FCV, in female BALB/c mice. The doses of FCV administered to the mice in each group are indicated in the graph. For Group 1, FCV, 63 mg/kg, was co-administered with VACV by the iv route. Group 3 was administered FCV only by po route. Groups 4-8 were administered VACV and FCV in combination by the po route.

Exposure, based on AUC values, generally increased with dose level in all groups. FIGS. 22, 23, and 24 show the $AUC_{last}$ values for each group allowing a visual comparison of the exposure to each analyte. The $C_{max}$ and AUC values tended to increase with dose level in Groups 4-8. The fold increase in $AUC_{last}$ for each higher dose ranging from 1.39-fold (VACV-equivalent, Group 8/Group 7) to 4.51-fold (FCV-equivalent, Group 6/Group 5). The AUC values for PCV were higher than for FCV-equivalent except in Groups 7 and 8.

TABLE 12

Pharmacokinetic Parameters for VACV-equivalents,
FCV-equivalents and PCV in Female BALB/c Mice

| Group | Analyte [a] | $t_{1/2}$ (hr) | $T_{max}$ (hr) | $C_{max}$ (ng/ml) Mean | SE | $AUC_{last}$ (hr · ng/ml) Mean | SE | $AUC_{inf}$ (hr · ng/ml) |
|---|---|---|---|---|---|---|---|---|
| 1 | VACV-equiv | 0.79 | 0.083 | 92267 | 11617 | 98626 | 17114 | 98711 |
| 1 | FCV-equiv | 0.49 | 0.083 | 25433 | 7507 | 11949 | 2007 | 11973 |
| 1 | PCV | 1.29 | 0.083 | 8797 | 2289 | 15055 | 2598 | 15202 |
| 2 | VACV-equiv | 2.83 | 0.25 | 85000 | 3459 | 208370 | 22333 | 208769 |
| 3 | FCV-equiv | 1.72 | 0.25 | 12533 | 1671 | 9257 | 704 | 9340 |
| 3 | PCV | 0.97 | 0.25 | 8120 | 565 | 10609 | 727 | 11259 |
| 4 | VACV-equiv | NC | 0.25 | 35400 | 3459 | 19707 | 1653 | NC |
| 4 | FCV-equiv | NC | 0.25 | 3170 | 575 | 2356 | 323 | NC |
| 4 | PCV | 1.89 | 0.5 | 4587 | 1076 | 6103 | 744 | 6205 |
| 5 | VACV-equiv | 2.78 | 0.25 | 64700 | 2554 | 41385 | 2958 | 41640 |
| 5 | FCV-equiv | NC | 0.25 | 3883 | 277 | 2074 | 156 | NC |
| 5 | PCV | 2.34 | 0.5 | 3147 | 400 | 5011 | 591 | 5137 |
| 6 | VACV-equiv | 2.89 | 0.25 | 76867 | 9198 | 115151 | 25063 | 116167 |
| 6 | FCV-equiv | 2.31 | 0.25 | 11940 | 2241 | 9353 | 1183 | 9486 |
| 6 | PCV | 2.34 | 0.5 | 7103 | 720 | 18427 | 3019 | 19212 |
| 7 | VACV-equiv | 1.12 | 1 | 94667 | 3820 | 318276 | 51755 | 318545 |
| 7 | FCV-equiv | 2.21 | 0.25 | 40833 | 5399 | 35411 | 2733 | 35521 |
| 7 | PCV | 1.31 | 0.25 | 16933 | 775 | 50196 | 6576 | 50929 |

TABLE 12-continued

Pharmacokinetic Parameters for VACV-equivalents,
FCV-equivalents and PCV in Female BALB/c Mice

| Group | Analyte [a] | $t_{1/2}$ (hr) | $T_{max}$ (hr) | $C_{max}$ (ng/ml) Mean | SE | $AUC_{last}$ (hr · ng/ml) Mean | SE | $AUC_{inf}$ (hr · ng/ml) |
|---|---|---|---|---|---|---|---|---|
| 8 | VACV-equiv | 1.72 | 1 | 141333 | 2848 | 442084 | 16596 | 446455 |
| 8 | FCV-equiv | 4.59 | 1 | 88433 | 8272 | 145111 | 9369 | 145346 |
| 8 | PCV | 4.30 | 1 | 31167 | 2635 | 84526 | 6326 | 85548 |

[a] Valacyclovir in plasma was all converted to acyclovir prior to analysis. Concentrations of acyclovir represent the total of valciclovir plus acyclovir and are termed VACV-equiv. Famciclovir was also converted to a metabolite formed by blood esterase that was measured and referred to as FCV-equiv. FCV metabolite, penciclovir (PCV), was measured in plasma separately.
[b] Calculated using $AUC_{last}$ Discussion and Conclusions Administration of VACV and FCV, alone or in combination, resulted in minimal clinical effects in female BALB/c mice that were dosed with as much as 500 mg/kg VACV plus 250 mg/kg FCV. Because plasma samples were collected without an esterase inhibitor, bioanalysis was performed to determine VACV-equivalent and FCV-equivalent. The hepatic metabolite of FCV, PCV was also measured in plasma samples. $C_{max}$ was achieved rapidly in all groups after oral dosing, the peak plasma concentration was observed at 0.25, 0.50 or 1.0 hr in Groups 2-8. The $t_{1/2}$ values for po groups ranged from 1.12 hr (VACV-equivalent, Group 7) to 4.59 hr (FCV-equivalent, Group 8). Doses in Group 4-8 increased 2-fold with each successive group while exposure based on $C_{max}$ and AUC values tended to increase with dose, though not in a consistently proportional manner.

Materials and Methods

Materials

Acetonitrile and methanol were purchased Avantor (Center Valley, Pa.). Acyclovir, dimethyl sulfoxide, formic acid, ganciclovir, and 2-propanol were purchased from Sigma-Aldrich (Milwaukee, Wis.). Female BALB/c mouse plasma was purchased from Bioreclamation, LLC (Hicksville, N.Y.). Chromatography was achieved with a Supelco® Discovery® HS F5 HPLC column (50×4.0 mm, 3 μm) purchased from Sigma-Aldrich (Milwaukee, Wis.).

Bioanalytical Method

Calibration Standards for Plasma Analysis. Acyclovir calibration standards (50, 500, 1000, 2000, 5000, and 8000 ng/ml) and Quality Control (QC) samples (100, 1500, and 7500 ng/ml) were prepared in female BALB/c mouse plasma. Famciclovir calibration standards (25, 100, 500, 1000, 2000, 5000, and 8000 ng/ml) and Quality Control (QC) samples (50, 1500, and 7500 ng/ml) were prepared in female BALB/c mouse plasma. Penciclovir calibration standards (50, 500, 1000, 2000, 5000, and 8000 ng/ml) and Quality Control (QC) samples (100, 1500, and 7500 ng/ml) were prepared in female BALB/c mouse plasma. Preparation of standards and QCs was as follows. A primary stock solution of 1 mg/ml FCV, penciclovir, or valaciclovir was prepared by accurately weighing out compound and adding dimethyl sulfoxide to achieve a concentration of 1 mg/ml in solution. The primary stock 1 mg/ml FCV, penciclovir, or acyclovir stock solution was used to prepare various spiking solutions by dilution with dimethyl sulfoxide. One volume of spiking solutions was added to 99 volumes of blank female BALB/c mouse plasma to attain nominal concentrations of standards with a final non-plasma matrix of 1.0%. These calibration standards and QCs were prepared fresh daily and stored at room temperature for 24 hours prior to assay to allow hydrolysis of VACV and FCV to go to completion. The calibration standards and QCs were subsequently analyzed in triplicate, respectively, on each day of study sample analysis.

Sample Preparation for Plasma Analysis. FCV and VAVC are intrinsically unstable in mouse plasma due to the presence of high levels of esterase activity in this matrix. The analytical strategy to address this problem was to thaw the study samples and allow them to sit at room temperature for a period of 24 hours, in which time the VACV is converted to acyclovir, and FCV is concerted to an esterase product that is detected in the mass spectrometer (see below). Both of these esterase products, as well as the penciclovir generated in vivo from FCV by hepatic metabolism, were all shown to be stable in mouse plasma during method development. Note that calibration standards and QCs were incubated at room temperature for 24 hours in parallel with the study samples.

Sample processing for the standards, QCs and study samples (sample volume 50 μl) entailed the addition of 200 μl of internal standard solution (400 ng/ml ganciclovir in acetonitrile). The mixtures were vortexed for 10 min on a multi-tube vortex mixer at maximal speed, and then the precipitate was sedimented by centrifugation (18000 g, 10 min). The supernatants were transferred to clean tubes, and the solvent was evaporated under vacuum. The dried residues were reconstituted with 60 μl of Milli-Q-Water containing 0.1% formic acid. The reconstituted samples were vortexed for 5 min on a multi-tube vortex mixer at one half speed, clarified by centrifugation (18000 g, 5 min), and then transferred to HPLC vials fitted with glass inserts for LC-MS/MS analysis. Study samples were quantitated using a set of calibration standards prepared in blank matrix that were processed in parallel.

LC-MS/MS Analysis. Samples were analyzed by LC-MS/MS and the details of the method are provided below.

LC Conditions:

HPLC Instrument: Waters 2795 Alliance Integrated System.

Autosampler Temp.: Room Temperature.

Column: Supelco® Discovery® HS F5 HPLC column (50×4.0 mm, 3 μm).

Column Temp.: Room Temperature.

Mobile phase: A=Milli-Q-Water with 0.1% formic acid; B=Acetonitrile with 0.1% formic acid.

Elution Mode: Gradient

TABLE 13

| Time (min) | % A | % B | Flow rate (ml/min) |
|---|---|---|---|
| 0 | 95 | 5 | 0.3 |
| 0.5 | 95 | 5 | 0.3 |
| 2.5 | 50 | 50 | 0.3 |
| 3.5 | 5 | 95 | 0.3 |
| 6.0 | 5 | 95 | 0.3 |
| 6.02 | 95 | 5 | 0.3 |
| 12.0 | 95 | 5 | 0.3 |

Flow Split: None
Flow Divert: None
Injection volume: 20 μl
Needle Wash: 75/25/0.1% (v/v/v) acetonitrile/2-propanol/formic acid
Purge Solution: 10%/90% (v/v) methanol/water
MS Conditions:
Instrument: Waters Micromass Quattro LC mass spectrometer.
Ionization: Electrospray ionization, positive ion mode.
Detection: Multiple Reaction Monitoring (MRM).

TABLE 14

| Analyte | MRM Transition (m/z) | Collision Energy | Retention Time (min) |
|---|---|---|---|
| Acyclovir | 225.60→151.80 | 12 eV | ~2.45 |
| Famciclovir* | 322.00→135.80 | 30 eV | ~3.06 |
| Penciclovir | 253.90→151.90 | 20 eV | ~2.55 |
| Ganciclovur (IS) | 256.00→151.70 | 15 eV | ~2.45 |

*Famciclovir is measured as its esterase product

Dwell Times: 0.25 sec
Resolution: Unit mass resolution at Q1 and Q3
Capillary Voltage: 3.50 kV
Cone Voltage: 20 V
Desolvation Temp.: 375° C.
Source Temp.: 115° C.
Quantitation: Integration and Quantitation by the Quanlynx portion of Masslynx Software 4.0 SP4.

Data Analysis. The calibration standard curves for acyclovir, FCV, and penciclovir were prepared by performing weighted (1/y) quadratic regression of the peak area ratio (PAR) of acyclovir, FCV, or penciclovir respectively to that of ganciclovir (internal standard) as the dependent variable (y-axis), and acyclovir, FCV, or penciclovir concentration as the independent variable (x-axis). The regression yields an equation of the form:

$$PAR = a[Analyte]^2 + b[Analyte] + c$$

where Analyte=FCV, acyclovir, or penciclovir.

To solve for the concentration of acyclovir, FCV, and penciclovir in the samples, the quadratic equation was first made equal to zero by subtracting y (peak area ratio of acyclovir, FCV, or penciclovir/IS) from both sides of the equation, which results in a new constant (c-y), and then solving the equation below:

$$\text{Concentration of Analyte}(x) = (-b \pm \sqrt{[b2 - 4a(c-y)]})/2a$$

These calculations are performed by the QuanLynx portion of the Masslynx software. The goodness of fit of this standard curve is indicated by the coefficient of determination ($r^2$) obtained from the quadratic regression, with perfect fit yielding an $r^2$ value of 1.000.

Lower Limit of Quantitation. For this study 50 ng/ml was set as the lowest concentration point on the acyclovir calibration curve. The back-calculated acyclovir concentration for plasma was 62.8±24.4 ng/ml (n=5), which corresponds to mean % CV of 38.9% with % Accuracy of 126%. For this study 25 ng/ml was set as the lowest concentration point on our FCV calibration curve. The back-calculated FCV concentration for plasma was 26.6±8.89 ng/ml (n=7), which corresponds to mean % CV of 33.4% with % Accuracy of 106%. For this study 50 ng/ml was set as the lowest concentration point on our penciclovir calibration curve. The back-calculated penciclovir concentration for plasma was 51.0±22.2 ng/ml (n=7), which corresponds to mean % CV of 43.6% with % Accuracy of 102%.

Analysis of Plasma Samples

Figure 25A:
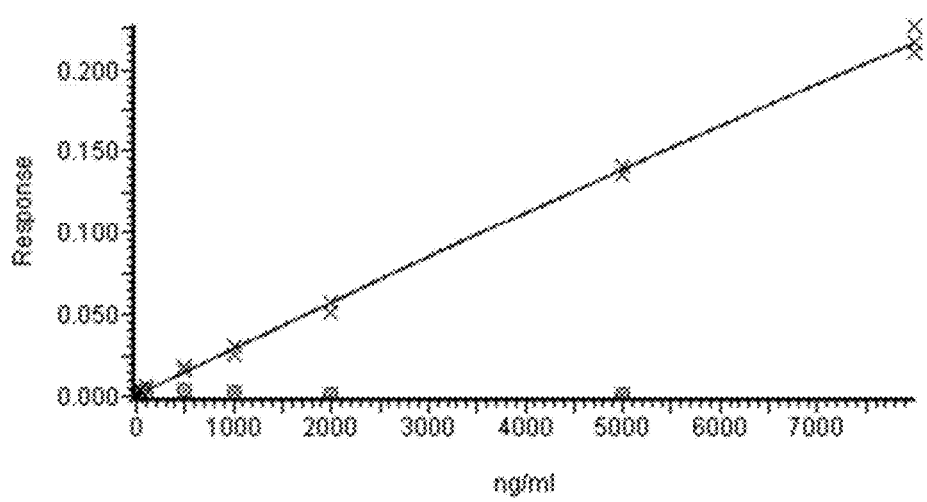
FIG. 25A-25C. Representative plasma standard curves for analysis of acyclovir (A), famciclovir (B) and penciclovir (C). (A) Acyclovir: Coefficient of Determination: $R^2=0.993363$; Calibration cure: $-2.34606e-010*x^2+2.88714e-005*x+0.000510796$; Response type:Internal Std (Ref2), Area*(IS Conc./IS Area); Curve type $2^{nd}$ Order, Origin: Exclude, Weighting: 1/y, Axis trans: None. (B) Famciclovir Esterase Product: Coefficient of Determination: $R^2=0.982788$; Calibration cure: $1.69416e-008*x^2+0.00017409*x+-0.000628661$; Response type:Internal Std (Ref2), Area*(IS Conc./IS Area); Curve type $2^{nd}$ Order, Origin: Exclude, Weighting: 1/y, Axis trans: None. (C) Penciclovir: Coefficient of Determination: $R^2=0.983086$; Calibration cure: $3.428e-011*x^2+1.4895e-005*x+-0.000210822$; Response type:Internal Std (Ref2), Area*(IS Conc./IS Area); Curve type $2^{nd}$ Order, Origin: Exclude, Weighting: 1/y, Axis trans: None.
Figure 25B:
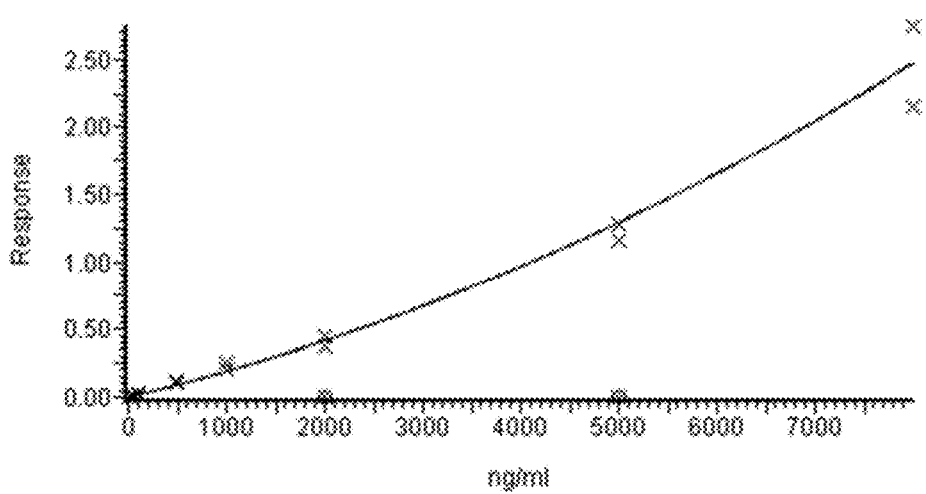
Figure 25C:
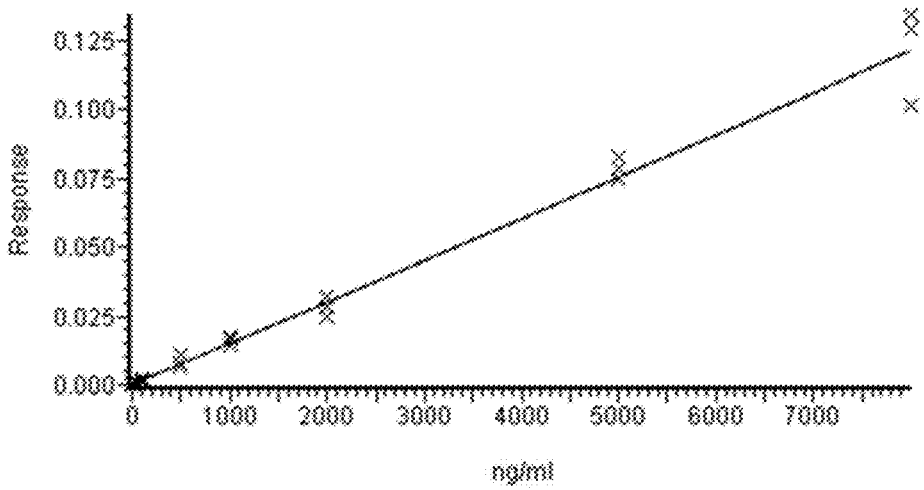

Representative standard curves for the sample assay are presented in FIG. 25A (acyclovir), 25B (FCV), 25C (penciclovir). Calibration curve data for all days of analysis are presented in Table D-1. Results of the QC samples over the course of the analytical runs in this study are summarized in Table D-2. The experimental samples from this study were analyzed with the bioanalytical method described, and the results of these analyses for the individual mouse at each of the plasma samples are presented in Table D-3 (acyclovir), Table D-4 (FCV), and Table D-5 (penciclovir).

Example 4: Pharmacodynamics Study of Valacyclovir and Famciclovir Following a HSV Vaginal Infection in Female Guinea Pigs This study focuses on pharmacodynamics of valacyclovir and famciclovir in combination for the prevention in an HSV-2 strain MS infection of guinea pigs. The 2:1 ratio of valacyclovir:famciclovir is selected as representative of advantageous combination amounts. Efficacious ratios include about 5:1, about 4:1, about 3:1, about 2:1, about 1:1, about 1:2, about 1:3, about 1:4, or about 1:5. Treatment begins 7 days before infection. Groups are treated for 14 days post infection. All groups are then monitored for 14 days for recurrence of infection. All treated groups are monitored for recurrent phase until day 28. At day 28 all guinea pigs are sacrificed and DRG's collected.

Experimental Design

Species and Strain: Guinea Pig and Hartley
Route of Administration: PO—after training to take the drug willingly.
Frequency: Daily
Dosing Volume: PO—TBD
HSV Infection: $10^6$ pfu of HSV-2 MS strain intravaginal inoculation
Duration of In-life Phase: 28 days+7 for pre-treatment

TABLE 15

Experimental Setup

| Group | Test Compound[a] | Dose (mg/kg)[a] | Route/Dose[c] | | No. of animals[b] | Infection |
|---|---|---|---|---|---|---|
| 1 | Water | N/A | PO | | 15 | HSV |
| 2 | A + B (low) | A - 29 | PO | A | 15 | HSV |
| | | B - 12 | | B | | |
| 3 | A + B (med) | A - 48 | PO | A | 15 | HSV |
| | | B - 24 | | B | | |
| 4 | A + B (high) | A - 96 | PO | A | 15 | HSV |
| | | B - 48 | | B | | |

[a]A = Valacyclovir (VACV); B = Famciclovir (FCV)
[b]Serum and swabs are collected from each guinea pig
[c]PO = per os, i.e. orally Materials and Methods
A. Test and Control Articles
1. Test Article 1: Valacyclovir (Valacyclovir Hydrochloride; VACV)
   Manufacturer: Sigma Aldrich
   Lot Number: XXX
   Physical Description: white powder
   Storage Conditions: Refrigerated, 2 to 8° C.
2. Test Article 2: Famciclovir
   Manufacturer: Sigma Aldrich
   Lot Number: XXXX
   Physical Description: white powder
   Storage Conditions: Refrigerated, 2 to 8° C.
3. Vehicle Control: Water
   Supplier: N/A
   Manufacturer: N/A
   Lot Number: N/A
   Physical Description: N/A
   Storage Conditions: N/A
   Preparation of Dose Formulations:
      Dose formulation will be prepared by using the free base molecular weight; VACV will use a correction factor of 1.11.
      Dose formulations will be prepared by combining the appropriate amount of test article in the vehicle to achieve the target concentration. The formulations will be mixed will using a vortex mixer and/or sterile stir bar and/or sonication. Visual inspection o each formulation will be documented. Details of dose preparation will be included in the final report. Formulations (diluted) will be prepared within 2 h of use.
   Disposition:
      Partially used test article vials, remaining vehicle control, and residual dose formulations will be discarded after the dose administration phase of the study is complete.
   Method for Assuring Correct Dosing:
      The administration of each dose formulation will be properly documented and amount administered recorded
B. Test System
Species: Guinea Pig
Strain: Hartley
Supplier: Charles River Laboratories or other reputable supplier
Number of Animals: 60
Sex: female
Age at First Dose:
Weight Range at First Dose: 250-350 g female (weight appropriate to age)
Animal Care: General procedures for animal care and housing will be in accordance with the current Association for Assessment and Accreditation of Laboratory Animal Care (AAALAC) recommendations, current requirements stated in the *Guide for the Care and Use of Laboratory Animals* (National Research Council), and current requirements as stated by the U.S. Department of Agriculture through the Animal Welfare Act and Animal Welfare Regulations (November 2013).
Quarantine/Acclimation: At least 2 days
Housing: 2 per cage (Is this good or too few?)
Cages: Standard,
Light Cycle: 12 h light/12 h dark
Temperature: 68-79° F.
Humidity: 30-70%. Brief excursions outside this range may occur; excursions of less than 4 h/day will not be considered deviations from the protocol.
Ventilation: At least 10 room volumes per hour, with no recirculation of air.
Food: Food will be provided ad libitum.
Water: Water will be provided ad libitum. Based on previous reports, no contaminants that could interfere with and affect the results of the study are expected to be present in the water
Assignment of Animals to Study
Day: No more than 3 days before initiation of treatment
Randomization: Animals will be randomly assigned to treatment groups.
Identification: Animals will be individually identified by a unique ear punch or by another approved method.
Welfare of the Animals: Every effort will be made to minimize, if not eliminate, pain and suffering in all animals in this study. Moribund animals and animals experiencing undue pain and suffering will be euthanized. The DRG will be harvested after euthanization.
C. Experimental Procedure (In-Life Evaluations)
1. Infection Dose Treatment: Day 0: Guinea pig will be administered $10^6$ pfu of HSV-2 MS strain intravaginally.
2. Mortality/Morbidity: After the infection, animals will be checked at least once daily.
3. Clinical Observations: After infection, recorded once daily to the end of study. Animals with findings, defined in the early remove criteria, that are observed to be moderate-to-extreme will have a second observation conducted that same day in the afternoon at least 6 hours apart from the morning observation. Animals will be examined for any altered clinical signs, including gross motor and behavioral activity, and observable changes in appearance. For vaginal disease a 4-point scale will be used:
   0, no apparent infection
   1, genital erythema
   2, moderate genital infection
   3, purulent genital ulceration and hair loss, poor condition
   4, severe ulceration of genital and surrounding tissue, hind limb paralysis (leading to euthanasia)
4. Criteria for Early Removal: IACUC endpoints will be followed. If an animal has either lost more than 25% of their body weight or has a clinical illness score (described below) of at least 3 they will be euthanized and DRG collected for future analysis, or a vaginal score of 4 (as described above).
   % Change in body weight: Calculated using the animal's pre-dose (Day 0, baseline) body weight. Clinical illness score: each of the following conditions will be scored one point. If an animal illness score is a 3 or greater the animal will be euthanized
      Abnormal posture (hunched)
      Abnormal appearance (ruffled)
      Ambulatory to the site
      Ambulatory to the touch
      Excoriation/self-mutilation
      Paralysis
D. Survival Euthanasia
Interval: Day 28 for any surviving animals after completing morning clinical observations. Terminal bleed, DRG collected.
Euthanasia: Best practice
E. Evaluation of Data Parameters
Proposed Statistical Tests: Body weight mean and standard deviations will be calculated and evaluated by one-way analysis of variance (ANOVA), followed by Dunnett's test if ANOVA is significant.

Kaplan-Meier survival curves will be used to evaluate mortality data. A power analysis with log-ranked test followed by a Cox Regression analysis will be conducted to estimate hazard ration relative to the vehicle control.

Viremia from swabs and the DRG will be assessed and evaluated by one-way analysis of variance (ANOVA), followed by Dunnett's test if ANOVA is significant.

Criteria for Null Hypothesis Rejection: p≤0.05
Samples collected for future analysis
Viral Swabs: Guinea pigs will be swabbed for virus at day 3, 5, 7, 9, 11, 14, 21, and 28
Blood Draws: Treated Guinea Pigs will be bled on day 1, day 7, day 14 and serum collected and stored at −80.
End of study: Guinea Pigs will be bled and serum collected and stored at −80.
Dorsal Root Ganglia will be collected from all animals and stored at −80.

Example 5: In Vitro Study of Human Fibroblasts

Cells and viruses. In vitro studies are performed using human foreskin fibroblast (HFF), Vero cells ME-180-cells. Strains of HSV-1 used to assess antiviral activity include the wild-type (wt) F and strain as well as ACV-resistant isolates. The wt HSV-2 strain G as well as ACV resistant isolates are to evaluate the activity of the compounds against HSV-2 and resistant strains.

Standard plaque reduction assays are performed with monolayers of confluent HFF, vero and ME-180 cells in 6-well plates. Briefly, virus suspensions are used to infect triplicate monolayers of cells (HFF, Vero or ME-180) in 6-well plates. After adsorption of the virus, the medium is replaced with growth medium containing 6 different concentrations of the compounds. After a 3-day incubation, cell monolayers are stained with crystal violet and plaques are enumerated. Compound concentrations sufficient to reduce plaque numbers by 50% (EC50) are interpolated from the experimental data.

Combined efficacy is also assessed using the Chou Talalay approach for two drug groups and using the following fixed dose ratios: 0.25 EC50, 0.5 EC50, EC50, 2 EC50, 4 EC50. Four replicate plates are infected with either strain E-377 or MS at a multiplicity of infection (MOI) of 0.01 PFU/cell. At 3 days after infection, genome copy number is quantified by real-time PCR to provide absolute quantification. Synergy is demonstrated using the Chou Talalay approach.

Efficacy is also demonstrated by EC50 and EC90 against HSV-1 and HSV-2 virus as well as in ACV resistant strains. The experiment will be performed in triplicate.

Example 6: Effectiveness of HSV Pre-Exposure Treatment in the Prevention of HSV Infection in Seronegatives in Discordant Relationships Purpose: The purpose of the study is to assess the effectiveness of oral administration of valacyclovir and famciclovir in preventing HSV-2 infection in HSV seronegative partner in a monogamous sexual relationship with an HSV seropositive partner. The study confirms that efficacy of the combination therapy at a dose below 1 g of drug substance is superior to valacyclovir alone. The study can be expanded to demonstrate efficacy of valacyclovir and famciclovir in larger or smaller amounts and in ratios other than 2:1 valacyclovir:famciclovir such as about 5:1, about 4:1, about 3:1, about 2:1, about 1:1, about 1:2, about 1:3, about 1:4, or about 1:5. The ratio of about 2:1 valacyclovir:famciclovir may be preferred. The drug substance amounts provide about 10 mg/kg valacyclovir and 5 mg/kg famciclovir for a 65 kg subject.

Intervention:
Arm 1: Seronegative participants are administered 650 mg of valacyclovir and 325 mg of famciclovir, or a placebo once daily.
Arm 2: Seronegative participants are administered 650 mg of valacyclovir and 325 mg of famciclovir, or a placebo once daily. Seropositive partners are administered 650 mg of valacyclovir and 325 mg of famciclovir, or once daily.

Description: Seronegative participants are administered 650 mg of valacyclovir and 325 mg of famciclovir, or a placebo once daily for at least seven days prior to coitus. In the second arm, HSV seropositive participants are administered 650 mg of valacyclovir and 325 mg of famciclovir once daily beginning at least seven days prior to coitus and for the duration of the study. Treatment of symptomatic episodes in the HSV seropositive participants during the duration of the study optionally involve increasing the dosage of valacyclovir to 650 mg of valacyclovir and 325 mg of famciclovir bid×3 days.

HSV seronegative and seropositive participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV immediately stop using the ring and are referred to local health facilities for care and treatment, with an option to enroll in a follow-up study to assess the impact of prophylactic treatment with valacyclovir, if any, on HSV or HIV treatment outcomes.

Eligibility and Inclusion Criteria:
HSV seronegative subjects in a monogamous sexual relationship with an HSV seropositive partner.

Use of an effective method of contraception at enrollment and continued use of the effective method for the duration of study participation. Effective methods include physical barriers such as condoms and diaphragms, hormonal methods, intrauterine device inserted at least 28 days prior to enrollment, and sterilized (self or partner).

Seropositive partner does not have a history of frequent symptomatic episodes (>9 episodes/year).

Exclusion Criteria:
Patients with a psychiatric disorder that might cause difficulty in obtaining informed consent or in conducting the trial.

Pregnant or nursing.
HIV seropositive.
Pre-exposure prophylaxis for HSV or HIV prevention within the 6 months prior to enrollment.
Post-exposure prophylaxis for HSV or HIV prevention within the 6 months prior to enrollment.
Treatment with antivirals within the 6 months prior to enrollment.

Primary Outcome Measures:
Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who adhered to the treatment regimen as monitored by self-reporting and/or measurement of valacyclovir drug in the subjects' system during treatment.

Percentage of subjects infected with HSV who adhered to the treatment regimen and had partners who took the valacyclovir as directed.

Percentage of subjects infected with HSV who adhered to the treatment regimen and had partners who did not take the valacyclovir as directed.

Percentage of subjects infected with HSV who had detectable levels of drug in their system during treatment.

Secondary Outcome Measures:
Safety and tolerability by adverse event assessment.
HSV incidence after study completion.
Pharmacokinetics: assessment of concentration of active agents in plasma before, during and after trial period.
Adherence to the protocol-specific product regimen as determined by self-reported questionnaires.
Incidence of sexually transmitted disease.
Incidence of pregnancy.
Viral shedding of at least a subset of partners with daily swabs for study duration.

Example 7: Effectiveness of HSV Pre-Exposure Treatment in the Prevention of HSV Infection in Seronegatives in Discordant Relationships Purpose: The purpose of the study is to assess the effectiveness of oral administration of valacyclovir and famciclovir in preventing HSV-2 infection in HSV seronegative partner in a monogamous sexual relationship with an HSV seropositive partner. The drug substance amounts coincide with EC90 in animal studies. The study confirms that efficacy of the combination therapy using an EC90 dosage is superior to valacyclovir alone at a higher dose.

Intervention:
Arm 1: Seronegative participants are administered 800 mg of valacyclovir and 400 mg of famciclovir, or a placebo once daily.
Arm 2: Seronegative participants are administered 800 mg of valacyclovir and 400 mg of famciclovir, or a placebo once daily. Seropositive partners are administered 800 mg of valacyclovir and 400 mg of famciclovir, or once daily.

Description: Seronegative participants are administered 800 mg of valacyclovir and 400 mg of famciclovir, or a placebo once daily for at least seven days prior to coitus. In the second arm, HSV seropositive participants are administered 800 mg of valacyclovir and 400 mg of famciclovir once daily beginning at least seven days prior to coitus and for the duration of the study. Treatment of symptomatic episodes in the HSV seropositive participants during the duration of the study optionally involve increasing the dosage of valacyclovir to 800 mg of valacyclovir and 400 mg of famciclovir bid×3 days.

Example 8: Effectiveness of HSV Pre-Exposure Treatment in the Prevention of HSV Infection in Seronegatives at Risk for Exposure to HSV Purpose: The purpose of the study is to assess the effectiveness of oral administration of valacyclovir in preventing HSV-2 infection in HSV seronegatives at risk for sexual contact with a partner who is HSV seropositive or has an unknown HSV sero-status for the duration of the study. Sexual contact includes one or more incidents of sexual contact with one or more partners.

Intervention: Participants are administered 650 mg of valacyclovir or a placebo once daily.

Description: Participants are instructed to begin administration of 650 mg of valacyclovir and 325 mg famciclovir, or placebo at least seven days prior to coitus with any partner. Participants attend study visits during the course of enrollment. Study visits include behavioral assessments, adherence assessments, physical examinations, blood collection, urine collection, and pelvic specimen collection. Women receive initial and ongoing HSV and sexually transmitted disease risk-reduction counseling, male condoms, diagnosis and treatment of sexually transmitted infections, pregnancy testing and family planning services, and treatment or referrals for medical conditions. Women who test positive for HSV or HIV immediately stop using the drug and are referred to local health facilities for care and treatment, with an option to enroll in a follow-up study to assess the drugs impact, if any, on HSV or HIV treatment outcomes.

Eligibility and Inclusion Criteria:
HSV seronegative female subjects who were female at birth that are 18 years to 45 years of age and expect to have at least one incident of sexual contact with a partner with HSV seropositive status or unknown HSV sero-status.

Use of an effective method of contraception at enrollment and continued use of the effective method for the duration of study participation. Effective methods include physical barriers such as condoms or diaphragms, hormonal methods, intrauterine device inserted at least 28 days prior to enrollment, and sterilized (self or partner).

Exclusion Criteria:
Patients with a psychiatric disorder that might cause difficulty in obtaining informed consent or in conducting the trial.
Pregnant or nursing.
HIV or HSV seropositive.
Pre-exposure prophylaxis for HSV or HIV prevention within the 6 months prior to enrollment.
Post-exposure prophylaxis for HSV or HIV prevention within the 6 months prior to enrollment.
Treatment with antivirals within the 6 months prior to enrollment.

Primary Outcome Measures:
Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2

Western blot in a subject with a previously negative Western blot result for the corresponding HSV type.

Efficacy as determined by HSV seroconversion rate per person-months of product use, measured at the end of the investigational product use period.

Percentage of subjects infected with HSV who took the prophylaxis treatment as directed.

Percentage of subjects infected with HSV who had detectable levels of drug in their system during treatment.

Secondary Outcome Measures:

Safety and tolerability by adverse event assessment.

HSV incidence after completion of a dosing regimen of valacyclovir or placebo.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Number of sexual contact incidents during study duration.

Number of sexual partners during study duration.

HSV sero-status of sexual partners during study duration as reported by study participant. HSV sero-status of partners reported include: known HSV seropositive, unknown HSV sero-status, and known HSV seronegative.

Example 9: HSV Treatment Kit

An HSV prophylaxis kit for treatment of HSV. The kit has an oral formulation comprising a low dosage of valacyclovir (650 mg or less) and a low dosage of famciclovir (325 mg or less) and instructions having information on how to administer the composition. The instructions include dosing information useful for administration of the composition to an HSV seronegative subject to prevent HSV infection prior to HSV exposure. The HSV prophylaxis kit also includes dosing information and instructions for administration of the composition to an HSV seropositive subject to suppress HSV activation and viral shedding. The packing of the kit is designed to market to both HSV seronegative and HSV seropositive subjects.

Example 10: HSV Treatment Kit Comprising an Antiviral Transdermal Patch

An HSV prophylaxis kit for treatment of HSV using a transdermal patch. The kit has a composition comprising valacyclovir and famciclovir within a transdermal patch for sustained drug release, and instructions having information on how to affix the transdermal patch onto the skin of the subject. The kit is designed to maintain a plasma concentration similar to 650 mg valacyclovir and 325 mg famciclovir administered once per day to a 65 kg subject. In various embodiments, the kit contains a patch adjusted in size or agent concentration to maintain higher or lower plasma concentrations of valacyclovir and famciclovir in ratios of about 5:1, about 4:1, about 3:1, about 2:1, about 1:1, about 1:2, about 1:3, about 1:4, or about 1:5. The instructions include dosing information useful for application of the patch to an HSV seronegative subject to prevent HSV infection prior to HSV exposure. The HSV prophylaxis kit optionally includes dosing information and instructions for application of the patch to an HSV seropositive subject to suppress HSV activation and viral shedding. The packing of the kit is optionally designed to market to both HSV seronegative and HSV seropositive subjects.

Example 11: Effectiveness of HSV Post-Exposure Treatment in the Prevention of HSV Infection in Seronegatives Exposed to HSV Purpose: The purpose of the study is to assess the effectiveness of oral administration of valacyclovir and famciclovir in preventing HSV-2 infection in HSV seronegatives exposed to HSV.

Intervention: Participants are administered 800 mg of valacyclovir and 400 mg of famciclovir, or a placebo twice daily for ten days, with the first dose administered within 24 hours of exposure to HSV, ideally within several hours.

Description: Participants are instructed to take 800 mg of valacyclovir and 400 mg of famciclovir twice daily for 10 days starting within 24 hours of exposure to HSV. Participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Women who test positive for HSV or HIV are referred to local health facilities for care and treatment, with an option to enroll in a follow-up study to assess the impact of treatment, if any, on HSV or HIV treatment outcomes.

Eligibility and Inclusion Criteria:

HSV seronegative subjects who expect to have at least one incident of sexual contact with a partner with HSV seropositive status during the study duration. The partner can be a monogamous partner or not a monogamous partner. The sexual contact can include any number of sexual occasions with any number of sexual partners for the study duration.

Use of an effective method of contraception at enrollment and continued use of the effective method for the duration of study participation. Effective methods include hormonal methods, intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

HIV or HSV seropositive.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Renal insufficiency defined as CrCl<50 mL/min

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate at the end of the investigational product use period.

Percentage of subjects infected with HSV who following the treatment regimen after exposure to HSV. Treatment adherence is monitored by patient self-reporting and/or measurement of valacyclovir drug in their system during treatment.

Percentage of subjects infected with HSV who had detectable levels of drug in their system during treatment.

Secondary Outcome Measures:

Safety and tolerability by adverse event assessment.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Incidence of pregnancy.

Number of sexual contact incidents during study duration.

Number of sexual partners during study duration.

Number of HSV exposures during study duration.

Example 12: Effectiveness of Antiviral Combination Pre-Exposure Treatment in the Prevention of HSV and HIV Infection in HSV/HIV Seronegatives in Discordant Relationships Purpose: The purpose of the study is to assess the safety and effectiveness of oral administration of valacyclovir and famciclovir with tenofovir in preventing HSV or HIV infection in HSV and HIV seronegative women in a monogamous sexual relationship with an HSV seropositive partner or an HIV seropositive partner.

Intervention:

Arm 1: Seronegative participants are administered 650 mg valacyclovir and 325 mg famciclovir, HSV seropositive partners are administered 650 mg valacyclovir and 325 mg famciclovir. HIV seropositive partners continue on their usual prescribed anti-HIV regimen.

Arm 2: Seronegative participants are administered tenofovir and emtricitabine. HIV seropositive partners continue on their usual prescribed anti-HIV regimen.

Arm 3: Seronegative participants are administered valacyclovir, famciclovir, tenofovir, and emtricitabine, HSV seropositive partners are administered 650 mg valacyclovir and 325 mg famciclovir. HIV seropositive partners continue on their usual prescribed anti-HIV regimen.

Arm 4: Seronegative participants are administered a placebo. HIV seropositive partners continue on their usual prescribed anti-HIV regimen.

Description: Seronegative participants are administered 650 mg of valacyclovir and 325 mg famciclovir, HSV seropositive subjects are offered 650 mg valacyclovir and 325 mg famciclovir once daily at least seven days prior to coitus in the first arm. HIV seropositive participants continue on their usual standard of care anti-HIV regimen. In the second arm, HSV seronegative participants are administered tenofovir and emtricitabine. HIV seropositive partners continue on their usual prescribed anti-HIV regimen. In the third arm, HSV seronegatives are administered valacyclovir, tenofovir, and emtricitabine, HSV seropositive partners are administered 500 mg valacyclovir. HIV seropositive partners continue on their usual prescribed anti-HIV regimen. In the fourth arm, Seronegative participants are administered a placebo. HIV seropositive partners continue on their usual prescribed anti-HIV regimen. Treatment of symptomatic episodes in the HSV seropositive participants during the duration of the study optionally involve increasing the dosage of valacyclovir to 500 mg bid×5 days.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV are referred to local health facilities for care and treatment, with an option to enroll in a follow-up study to assess the impact of prophylactic treatment, if any, on HSV or HIV treatment outcomes.

Eligibility and Inclusion Criteria:

HSV and HIV seronegatives who are in a monogamous sexual relationship with an HSV or HIV seropositive partner.

Use of an effective method of contraception at enrollment and continued use of the effective method for the duration of study participation. Effective methods include physical barriers such as condoms or diaphragms, hormonal methods, intrauterine device inserted at least 28 days prior to enrollment, and sterilized (self or partner).

HSV Seropositive partner does not have a history of frequent symptomatic episodes (>9 episodes/year).

Exclusion Criteria:

Patients with a psychiatric disorder that might cause difficulty in obtaining informed consent or in conducting the trial.

Pregnant or nursing.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Drug resistance to any of the treatment antivirals.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who adhered to study guidelines as monitored by patient self-reporting and/or measurement of drug(s) in their system during treatment.

Percentage of subjects infected with HSV who adhered to study guidelines and had partners who took the valacyclovir as directed.

Percentage of subjects infected with HSV who adhered to study guidelines and had partners who did not take the valacyclovir as directed.

Percentage of subjects infected with HSV who had detectable levels of drug(s) in their system during treatment.

Efficacy as determined by HIV-1 seroconversion rate per person-months of product use, measured at the end of the investigational product use period. The primary endpoint is HIV-1 seroconversion measured by immunoassay-based HIV blood tests. Endpoint confirmation of HIV infection is by Western blot.

Percentage of subjects infected with HIV who adhered to study guidelines as monitored by patient self-reporting and/or measurement of drug(s) in their system during treatment.

Percentage of subjects infected with HIV who adhered to study guidelines and had partners who took their anti-HIV medications as directed.

Percentage of subjects infected with HIV who adhered to study guidelines and had partners who did not take their anti-HIV medications as directed.

Percentage of subjects infected with HIV who had detectable levels of drug(s) in their system during treatment.

Secondary Outcome Measures:

Safety as determined by grade 3 and 4 adverse events, clinically significant grade 2 laboratory findings (based on DADS grading) and all serious adverse events.

HSV incidence after completion of course of antivirals.

HIV incidence after completion of course of antivirals.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Example 13: Effectiveness of Antiviral Combination Pre-Exposure Treatment in the Prevention of HSV and HIV Infection in Seronegatives at Risk for Exposure to HSV and HIV Purpose: The purpose of the study is to assess the safety and effectiveness of oral administration of valacyclovir, tenofovir, and emtricitabine in preventing HSV-2 and/or HIV infection in HSV and HIV seronegatives at risk for sexual contact with a partner who is HSV or HIV seropositive or has unknown HSV or HIV sero-status during study duration. Sexual contact includes one or more incidents of sexual contact with one or more partners.

Intervention: Seronegative participants are administered valacyclovir, tenofovir/emtricitabine, valacyclovir and tenofovir/emtricitabine, or a placebo.

Description: Seronegative participants are administered 650 mg of valacyclovir and 325 mg famciclovir, 300 mg of tenofovir and 200 mg of emtricitabine per day, 500 mg of valacyclovir, 250 mg famciclovir, 300 mg of tenofovir and 200 mg of emtricitabine, or a placebo once daily starting at least seven days prior to coitus.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV are referred to local health facilities for care and treatment, with an option to enroll in a follow-up study to assess treatment impact, if any, on HSV or HIV outcomes.

Eligibility and Inclusion Criteria:

HSV and HIV seronegative female subjects who were female at birth that are 18 years to 45 years of age and expect to have at least one incident of sexual contact with a partner with HSV or HIV seropositive status, or unknown HSV or HIV sero-status.

Use of an effective method of contraception at enrollment and continued use of the effective method for the duration of study participation. Effective methods include physical barriers such as condoms or diaphragms, hormonal methods, intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

Pre-exposure prophylaxis for HSV or HIV prevention within the 6 months prior to enrollment.

Post-exposure prophylaxis for HSV or HIV prevention within the 6 months prior to enrollment.

Treatment with HSV antivirals within the 6 months prior to enrollment.

Drug Resistance to one or more agents in the HIV treatment arms

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who adhered to study guidelines as monitored by patient self-reporting and/or measurement of drug(s) in their system during treatment.

Percentage of subjects infected with HSV who had detectable levels of drug(s) in their system during treatment.

Efficacy as determined by HIV-1 seroconversion rate per person-months of product use, measured at the end of the investigational product use period. The primary endpoint is HIV-1 seroconversion measured by immunoassay-based HIV blood tests. Endpoint confirmation of HIV infection is by Western blot.

Percentage of subjects infected with HIV who adhered to study guidelines as monitored by patient self-reporting and/or measurement of drug(s) in their system during treatment.

Percentage of subjects infected with HIV who had detectable levels of drug(s) in their system during treatment.

Secondary Outcome Measures:

Safety as determined by grade 3 and 4 adverse events, clinically significant grade 2 laboratory findings (based on DADS grading) and all serious adverse events.

HSV incidence after completion of course of antivirals.

HIV incidence after completion of course of antivirals.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Example 14: HSV and HIV Treatment Kit

An HSV and HIV prophylaxis kit for treatment of HSV and HIV. The kit has an oral formulation comprising a low dosage of valacyclovir and famciclovir (650 mg or less valacyclovir, 325 mg or less famciclovir), a standard dosage of tenofovir (300 mg), a standard dosage of emtricitabine (200 mg), and instructions having information on how to administer the composition. The instructions include dosing information useful for administration of the composition to an HSV and HIV seronegative subject to prevent HSV and/or HIV infection prior to HSV and/or HIV exposure. The HSV and HIV prophylaxis kit optionally includes dosing information and instructions for administration of the composition to an HSV seropositive subject to suppress HSV activation and viral shedding. The packing of the kit is optionally designed to market to HIV seronegative, HSV seronegative, and HSV seropositive subjects.

Example 15: HSV and HIV Treatment Kit Comprising an Antiviral Transdermal Patch An HSV and HIV prophylaxis kit for treatment of HSV and HIV using a transdermal patch. The kit has a composition comprising valacyclovir and tenofovir within a transdermal patch and instructions having information on how to affix the transdermal patch onto the skin of the subject. The transdermal patch is designed to provide plasma concentrations of valacyclovir and famciclovir equivalent to a 650 mg valacyclovir, 325 mg famciclovir, and a standard dosage of tenofovir (300 mg) once per day. The instructions include dosing information useful for application of the patch to an HSV and HIV seronegative subject to prevent HSV and/or HIV infection prior to HSV and/or HIV exposure. The HSV and HIV prophylaxis kit optionally includes dosing information and instructions for application of the patch to an HSV seropositive subject to suppress HSV activation and viral shedding. The packing of the kit is optionally designed to market to HSV seronegative, HIV seronegative, and HSV seropositive subjects.

Example 16: HSV and HIV Treatment Kit Comprising an Antiviral Intravaginal Ring An HSV and HIV prophylaxis kit for treatment of HSV and HIV using an intravaginal ring. The kit has a composition comprising valacyclovir and famciclovir and tenofovir/emtricitabine within an intravaginal ring and instructions having information on how to insert the intravaginal ring into the vagina of a subject. The instructions include dosing and application information useful for the prevention of HSV and/or HIV infection in a seronegative subject. The HSV and HIV prophylaxis kit optionally includes instructions on how to suppress HSV activation and viral shedding in an HSV seropositive subject using the intravaginal ring. The packing of the kit is optionally designed to market to HSV seronegative, HIV seronegative, and HSV seropositive subjects.

Example 17: HSV and HIV Treatment Kit for Post-Viral Exposure Administration An HSV and HIV prophylaxis kit for treatment of HSV and HIV. The kit has an oral formulation comprising valacyclovir (800 mg) and famciclovir (400 mg) in a twice daily dosing regimen), tenofovir (300 mg/day), emtricitabine (200 mg/day) and raltegravir (400 mg twice per day); and instructions having information on how to administer the composition. The instructions include dosing information useful for administration of the composition to an HSV and HIV seronegative subject to prevent HSV and/or HIV infection after possible HSV and/or HIV exposure, but within 72 hours after possible exposure. The HSV and HIV prophylaxis kit optionally includes dosing information and instructions for administration of the composition to an HSV seropositive subject after an outbreak of genital herpes or cold sore. The packing of the kit is optionally designed to market to HSV seronegative, HIV seronegative, and HSV seropositive subjects.

Example 18: HSV and HIV Treatment Kit Comprising a Transdermal Patch for Post-Viral Exposure Administration An HSV and HIV prophylaxis kit for treatment of HSV and HIV using a transdermal patch. The kit has a transdermal patch that releases sustained high doses of valacyclovir and famciclovir, tenofovir, emtricitabine, and raltegravir and instructions having information on how to affix the transdermal patch onto the skin of a subject. The instructions include dosing information useful for application of the patch to an HSV and HIV seronegative subject after HSV and/or HIV exposure to prevent HSV and/or HIV infection. The HSV prophylaxis kit optionally includes dosing information and instructions for application of the patch to an HSV seropositive subject after an outbreak of genital herpes or cold sore. The packing of the kit is optionally designed to market to HSV seronegative, HIV seronegative, and HSV seropositive subjects.

Example 19: HSV and HIV Treatment Kit Comprising an Intravaginal Ring for Post-Viral Exposure Administration An HSV and HIV prophylaxis kit for treatment of HSV and HIV using an intravaginal ring. The kit has a composition comprising valacyclovir, famciclovir, and tenofovir within an intravaginal ring, wherein the valacyclovir, famciclovir, tenofovir, emtricitabine and raltegravir active agents are released at sustained high doses in use, and instructions having information on how to insert the intravaginal ring into the vagina of a subject. The instructions include dosing and application information useful for the prevention of HSV and/or HIV infection in a seronegative subject after HSV and/or within 72 hours of HIV exposure. The HSV and HIV prophylaxis kit optionally includes instructions on how to treat an outbreak of genital herpes or cold sores in an HSV seropositive subject using the intravaginal ring. The packing of the kit is optionally designed to market to HSV seronegative, HIV seronegative, and HSV seropositive subjects.

Example 20: Intravaginal Rings for Contraception and Prevention of HSV Infection Intravaginal rings are produced from ethylene vinylacetate copolymers and magnesium stearate and contain the active drugs etonogestrel (11.7 mg), ethinyl estradiol (2.7 mg), and the drugs valacyclovir and famciclovir in amounts to provide plasma concentrations equivalent to oral administration of about 650 mg valacyclovir and 325 mg famciclovir once daily. The amount of drugs released each day over a period of at least 14 days is measured in vitro. In vitro daily release profiles are determined using experimental conditions in vitro that effectively simulate the active drug diffusion that occurs in vivo.

Vaginal rings releasing ethinyl estradiol/etonogestrel and low doses of valacyclovir are selected as candidates for clinical trials for the prevention of pregnancy and HSV infection in seronegative subjects at risk for exposure to HSV. Optionally, vaginal rings releasing ethinyl estradiol/etonogestrel and high doses of valacyclovir are selected as candidates for clinical trials for the prevention of pregnancy and HSV in seronegative subjects exposed to HSV. The vaginal ring will comprise silicone.

The invention is further described by the following numbered paragraphs:

1. A pharmaceutical composition for treatment of herpes simplex virus (HSV) infection, prophylaxis, or pre-exposure prophylaxis against HSV infection in a subject in need thereof comprising: a therapeutically effective amount of (a) valacyclovir or a salt or solvate thereof and (b) famciclovir or a salt or solvate thereof; and pharmaceutically acceptable excipient(s), diluent(s), carrier(s) and/or adjuvant(s).
2. The pharmaceutical composition of numbered paragraph 1, comprising 0.5 mg/kg body weight to about 1000 mg/kg body weight of (a) and 0.5 mg/kg body weight to about 1000 mg/kg body weight of (b).
3. The pharmaceutical composition of numbered paragraph 2, comprising about 5 mg/kg body weight to about 50 mg/kg body weight of (a).
4. The pharmaceutical composition of numbered paragraph 2, comprising about 25 mg/kg body weight to about 100 mg/kg body weight of (a).
5. The pharmaceutical composition of numbered paragraph 2, comprising about 50 mg/kg body weight to about 250 mg/kg body weight of (a).
6. The pharmaceutical composition of numbered paragraph 2, comprising about 100 mg/kg body weight to about 500 mg/kg body weight of (a).
7. The pharmaceutical composition of any one of numbered paragraphs 2 to 6, comprising about 5 mg/kg body weight to about 50 mg/kg body weight of (b).
8. The pharmaceutical composition of any one of numbered paragraphs 2 to 6, comprising about 25 mg/kg body weight to about 100 mg/kg body weight of (b).
9. The pharmaceutical composition of any one of numbered paragraphs 2 to 6, comprising about 50 mg/kg body weight to about 250 mg/kg body weight of (b).
10. The pharmaceutical composition of any one of numbered paragraphs 2 to 6, comprising about 100 mg/kg body weight to about 500 mg/kg body weight of (b).
11. The pharmaceutical composition of numbered paragraph 2, comprising (a) and (b) in a dose ratio in mg/kg of about 5:1, about 4:1, about 3:1, about 2:1, about 1:1, about 1:2, about 1:3, about 1:4, or about 1:5.
12. The pharmaceutical composition of numbered paragraph 2, comprising about 5 mg/kg body weight to about 15 mg/kg body weight of (a) and about 2.5 mg/kg body weight to about 7.5 mg/kg body weight of (b).
13. The pharmaceutical composition of numbered paragraph 2, comprising about 10 mg/kg body weight to about 50 mg/kg body weight of (a) and about 5 mg/kg body weight to about 25 mg/kg body weight of (b).
14. The pharmaceutical composition of numbered paragraph 2, comprising about 50 mg/kg body weight to about 150 mg/kg body weight of (a) and about 20 mg/kg body weight to about 50 mg/kg body weight of (b).
15. The pharmaceutical composition of numbered paragraph 2, comprising about 100 mg/kg body weight to about 150 mg/kg body weight of (a) and about 50 mg/kg body weight to about 100 mg/kg body weight of (b).
16. The pharmaceutical composition of numbered paragraph 2, comprising about 150 mg/kg body weight to about 500 mg/kg body weight of (a) and about 100 mg/kg body weight to about 250 mg/kg body weight of (b).
17. The pharmaceutical composition of numbered paragraph 2, comprising about 250 mg/kg body weight to about 1000 mg/kg body weight of (a) and about 150 mg/kg body weight to about 500 mg/kg body weight of (b).
18. The pharmaceutical composition of numbered paragraph 2, comprising from greater than 100 mg/kg to about 700 mg/kg body weight of valacyclovir and from greater than 100 mg/kg to about 500 mg/kg body weight of famciclovir.
19. The pharmaceutical composition of any one of numbered paragraphs 1 to 18, comprising about 1 mg to about 8000 mg of valacyclovir or a salt or solvate thereof and about 1 mg to about 8000 mg famciclovir or a salt or solvate thereof.
20. The pharmaceutical composition of any one of numbered paragraphs 1 to 18, comprising about 125 mg to about 2000 mg of valacyclovir or a salt or solvate thereof and about 60 mg to about 1000 mg famciclovir or a salt or solvate thereof.
21. The pharmaceutical composition of any one of numbered paragraphs 1 to 20, formulated for oral administration.
22. The pharmaceutical composition of numbered paragraph 21, comprising an oral tablet, oral capsule, or oral solution.
23. The pharmaceutical composition of any one of numbered paragraphs 1 to 20, formulated for administration once daily or twice daily.
24. The pharmaceutical composition of any one of numbered paragraphs 1 to 20, formulated in sustained-release form.
25. The pharmaceutical composition of any one of numbered paragraphs 1 to 20, formulated in parenteral administration form.
26. The pharmaceutical composition of any one of numbered paragraphs 1 to 20, additionally comprising a therapeutically effective amount of an HIV antiviral agent.
27. The pharmaceutical composition of any one of numbered paragraphs 1 to 20, formulated for a female and additionally comprising a therapeutically effective amount of a contraceptive.
28. The pharmaceutical composition of any one of numbered paragraphs 1 to 20, additionally comprising a therapeutically effective amount of an additional antiviral agent.
29. The pharmaceutical composition of numbered paragraph 28, wherein the additional antiviral agent comprises a helicase-primase inhibitor, amenamevir, N-methancocarbathymidine (N-MCT), tenofovir, emtricitabine, lamivudine, interfereon, ribavirin, boceprevir, telaprevir, simeprevir, sofosbuvir, ledipasvir, tenofovir, ombitasvir, paritaprevir, penciclovir, pritelivir, brincidofovir, cidofovir, ganciclovir, valganciclovir, valomaciclovir, or ritonavir.
30. The pharmaceutical composition of any one of numbered paragraphs 1 to 20, wherein the HSV is HSV-1, HSV-2, varicella-zoster virus (VZV), Epstein-Barr virus (human herpes virus 4), cytomegalovirus (human herpes virus 5), roseolovirus (human herpes virus 6 and 7), or Karposi's sarcoma-associated herpes virus (human herpes virus 8).
31. The pharmaceutical composition of numbered paragraph 30, wherein the HSV is HSV-2.
32. The pharmaceutical composition of numbered paragraph 30, wherein the HSV is VZV.
33. A pharmaceutical composition for treatment of herpes simplex virus (HSV) infection, prophylaxis, or pre-exposure prophylaxis against HSV infection in a subject in need thereof comprising: a therapeutically effective amount of greater than 100 mg/kg body weight of an antiviral agent comprising acyclovir or a salt or solvate thereof, or valacyclovir or a salt or solvate thereof, or famciclovir or a salt or solvate thereof, or combinations thereof, whereby the risk of HSV infection in the subject is reduced.

34. The pharmaceutical composition of numbered paragraph 33, wherein the amount of the antiviral agent is from greater than 100 mg/kg to about 1000 mg/kg body weight.

35. The pharmaceutical composition of numbered paragraph 33, wherein the amount of the antiviral agent is from greater than 100 mg/kg to about 700 mg/kg body weight.

36. The pharmaceutical composition of numbered paragraph 33, wherein the amount of the antiviral agent is from greater than 100 mg/kg to about 500 mg/kg body weight.

37. The pharmaceutical composition of numbered paragraph 33, wherein the amount of the antiviral agent is from greater than 100 mg/kg to about 250 mg/kg body weight.

38. The pharmaceutical composition of numbered paragraph 33, wherein the amount of the antiviral agent is from about 125 mg/kg to about 500 mg/kg body weight.

39. The pharmaceutical composition of numbered paragraph 33, wherein the antiviral agent comprises valacyclovir or a salt or solvate thereof.

40. The pharmaceutical composition of numbered paragraph 33, wherein the antiviral agent comprises famciclovir or a salt or solvate thereof.

41. The pharmaceutical composition of numbered paragraph 33, wherein the antiviral agent comprises acyclovir or a salt or solvate thereof.

42. The pharmaceutical composition of numbered paragraph 33, which comprises 0.5 mg/kg to about 1000 mg/kg body weight of a second antiviral agent.

43. The pharmaceutical composition of numbered paragraph 33, which comprises 0.5 mg/kg to about 700 mg/kg body weight of a second antiviral agent.

44. The pharmaceutical composition of numbered paragraph 33, which comprises 0.5 mg/kg to about 500 mg/kg body weight of a second antiviral agent.

45. The pharmaceutical composition of numbered paragraph 33, which comprises greater than about 100 mg/kg body weight of a second antiviral agent.

46. The pharmaceutical composition of numbered paragraph 33, which comprises valacyclovir or a salt or solvate thereof and famciclovir or a salt or solvate thereof.

47. The pharmaceutical composition of numbered paragraph 33, which comprises valacyclovir or a salt or solvate thereof and acyclovir or a salt or solvate thereof.

48. The pharmaceutical composition of numbered paragraph 46, which comprises greater than 100 mg/kg body weight of valacyclovir and greater than 100 mg/kg body weight of famciclovir.

49. The pharmaceutical composition of numbered paragraph 46, which comprises from greater than 100 mg/kg to about 700 mg/kg body weight of valacyclovir and from greater than 100 mg/kg to about 500 mg/kg body weight of famciclovir.

50. The pharmaceutical composition of numbered paragraph 48, comprising about 1 mg to about 8000 mg of valacyclovir or a salt or solvate thereof and about 1 mg to about 8000 mg famciclovir or a salt or solvate thereof.

51. The pharmaceutical composition of numbered paragraph 48, comprising about 125 mg to about 2000 mg of valacyclovir or a salt or solvate thereof and about 60 mg to about 1000 mg famciclovir or a salt or solvate thereof.

52. The pharmaceutical composition of numbered paragraph 46, formulated for oral administration.

53. The pharmaceutical composition of numbered paragraph 52, comprising an oral tablet, oral capsule, or oral solution.

54. The pharmaceutical composition of numbered paragraph 46, formulated for administration once daily or twice daily.

55. The pharmaceutical composition of numbered paragraph 46, formulated in sustained-release form.

56. The pharmaceutical composition of numbered paragraph 46, formulated in parenteral administration form.

57. The pharmaceutical composition of numbered paragraph 46, additionally comprising a therapeutically effective amount of an HIV antiviral agent.

58. The pharmaceutical composition of numbered paragraph 46, formulated for a female and additionally comprising a therapeutically effective amount of a contraceptive.

59. The pharmaceutical composition of numbered paragraph 46, additionally comprising a therapeutically effective amount of an additional antiviral agent.

60. The pharmaceutical composition of numbered paragraph 59, wherein the additional antiviral agent comprises a helicase-primase inhibitor, amenamevir, N-methancocarbathymidine (N-MCT), tenofovir, emtricitabine, lamivudine, interfereon, ribavirin, boceprevir, telaprevir, simeprevir, sofosbuvir, ledipasvir, tenofovir, ombitasvir, paritaprevir, penciclovir, pritelivir, brincidofovir, cidofovir, ganciclovir, valganciclovir, valomaciclovir, or ritonavir.

61. The pharmaceutical composition of numbered paragraph 33, wherein the HSV is HSV-1, HSV-2, varicella-zoster (VZV), Epstein-Barr virus (human herpes virus 4), cytomegalovirus (human herpes virus 5), roseolovirus (human herpes virus 6 and 7), or Karposi's sarcoma-associated herpes virus (human herpes virus 8).

62. The pharmaceutical composition of numbered paragraph 61, wherein the HSV is HSV-2.

63. A method of pre-exposure prophylaxis against HSV infection in an HSV seronegative subject in need thereof, or a method of treating an HSV infection, or a method of suppressing an HSV infection, or a method of treatment or prophylactic treatment of a disease or condition associated with HSV infection, the method comprising administering to the subject daily a therapeutically effective amount of (a) valacyclovir or a salt or solvate thereof and (b) famciclovir or a salt or solvate thereof; and pharmaceutically acceptable excipient(s), diluent(s), carrier(s) and/or adjuvant(s).

64. The method of numbered paragraph 63, wherein the therapeutically effective amount comprises 0.5 mg/kg body weight to about 1000 mg/kg body weight of (a) and 0.5 mg/kg body weight to about 1000 mg/kg body weight of (b).

65. The method of numbered paragraph 64, wherein the therapeutically effective amount comprises about 5 mg/kg body weight to about 50 mg/kg body weight of (a).

66. The method of numbered paragraph 64, wherein the therapeutically effective amount comprises about 25 mg/kg body weight to about 100 mg/kg body weight of (a).

67. The method of numbered paragraph 64, wherein the therapeutically effective amount comprises about 50 mg/kg body weight to about 250 mg/kg body weight of (a).

68. The method of numbered paragraph 64, wherein the therapeutically effective amount comprises about 100 mg/kg body weight to about 500 mg/kg body weight of (a).

69. The method of any one of numbered paragraphs 64 to 68, wherein the therapeutically effective amount comprises about 5 mg/kg body weight to about 50 mg/kg body weight of (b).

70. The method of any one of numbered paragraphs 64 to 68, wherein the therapeutically effective amount comprises about 25 mg/kg body weight to about 100 mg/kg body weight of (b).

71. The method of any one of numbered paragraphs 64 to 68, wherein the therapeutically effective amount comprises about 50 mg/kg body weight to about 250 mg/kg body weight of (b).

72. The method of any one of numbered paragraphs 64 to 68, wherein the therapeutically effective amount comprises about 100 mg/kg body weight to about 500 mg/kg body weight of (b).

73. The method of numbered paragraph 64, wherein the therapeutically effective amount comprises (a) and (b) in a dose ratio in mg/kg of about 5:1, about 4:1, about 3:1, about 2:1, about 1:1, about 1:2, about 1:3, about 1:4, or about 1:5.

74. The method of numbered paragraph 64, wherein the therapeutically effective amount about 50 mg/kg body weight to about 150 mg/kg body weight of (a) and about 20 mg/kg body weight to about 50 mg/kg body weight of (b).

75. The method of numbered paragraph 64, wherein the therapeutically effective amount about 100 mg/kg body weight to about 150 mg/kg body weight of (a) and about 50 mg/kg body weight to about 100 mg/kg body weight of (b).

76. The method of numbered paragraph 64, wherein the therapeutically effective amount about 150 mg/kg body weight to about 500 mg/kg body weight of (a) and about 100 mg/kg body weight to about 250 mg/kg body weight of (b).

77. The method of numbered paragraph 64, wherein the therapeutically effective amount about 250 mg/kg body weight to about 1000 mg/kg body weight of (a) and about 150 mg/kg body weight to about 500 mg/kg body weight of (b).

78. The method of numbered paragraph 64, wherein the HSV infection is a neonatal infection.

79. The method of numbered paragraph 64, wherein the disease or infection associated with HSV infection is Alzheimer's disease.

80. A method of pre-exposure prophylaxis against herpes simplex virus (HSV) infection in an HSV seronegative subject in need thereof, or a method of treating an HSV infection, or a method of suppressing an HSV infection, or a method of treatment or prophylactic treatment of a disease or condition associated with HSV infection, the method comprising administering to the subject daily a therapeutically effective amount of greater than 100 mg/kg body weight of an antiviral agent comprising acyclovir or a salt or solvate thereof, or valacyclovir or a salt or solvate thereof, or famciclovir or a salt or solvate thereof, or combinations thereof, whereby the risk of HSV infection in the subject is reduced.

81. The method of numbered paragraph 80, wherein the amount of the antiviral agent is from greater than 100 mg/kg to about 1000 mg/kg body weight.

82. The method of numbered paragraph 80, wherein the amount of the antiviral agent is from greater than 100 mg/kg to about 700 mg/kg body weight.

83. The method of numbered paragraph 80, wherein the amount of the antiviral agent is from greater than 100 mg/kg to about 500 mg/kg body weight.

84. The method of numbered paragraph 80, wherein the amount of the antiviral agent is from greater than 100 mg/kg to about 250 mg/kg body weight.

85. The method of numbered paragraph 80, wherein the amount of the antiviral agent is from about 125 mg/kg to about 500 mg/kg body weight.

86. The method of numbered paragraph 80, wherein the antiviral agent comprises valacyclovir or a salt or solvate thereof.

87. The method of numbered paragraph 80, wherein the antiviral agent comprises famciclovir or a salt or solvate thereof.

88. The method of numbered paragraph 80, wherein the antiviral agent comprises acyclovir or a salt or solvate thereof.

89. The method of numbered paragraph 80, which comprises administering 0.5 mg/kg to about 1000 mg/kg body weight of a second antiviral agent.

90. The method of numbered paragraph 80, which comprises administering 0.5 mg/kg to about 700 mg/kg body weight of a second antiviral agent.

91. The method of numbered paragraph 80, which comprises administering 0.5 mg/kg to about 500 mg/kg body weight of a second antiviral agent.

92. The method of numbered paragraph 80, which comprises administering greater than about 100 mg/kg body weight of a second antiviral agent.

93. The method of numbered paragraph 80, wherein the antiviral agent comprises valacyclovir or a salt or solvate thereof and famciclovir or a salt or solvate thereof.

94. The method of numbered paragraph 80, wherein the antiviral agent comprises valacyclovir or a salt or solvate thereof and acyclovir or a salt or solvate thereof.

95. The method of numbered paragraph 93, wherein the antiviral agent comprises greater than 100 mg/kg body weight of valacyclovir and greater than 100 mg/kg weight of famciclovir.

96. The method of numbered paragraph 93, wherein the antiviral agent comprises greater than 100 mg/kg to about 700 mg/kg body weight of valacyclovir and greater than 100 mg/kg to about 500 mg/kg body weight of famciclovir.

97. The method of numbered paragraph 93, which comprises administering about 1 mg to about 8000 mg of valacyclovir or a salt or solvate thereof and about 1 mg to about 8000 mg of famciclovir or a salt or solvate thereof.

98. The method of numbered paragraph 93, which comprises administering about 125 mg to about 2000 mg of valacyclovir or a salt or solvate thereof and about 60 mg to about 1000 mg of famciclovir or a salt or solvate thereof.

99. The method of numbered paragraph 80, wherein the administering is oral or intravenous.

100. The method of numbered paragraph 80, wherein the administering is once daily or twice daily.

101. The method of numbered paragraph 80, wherein the administering begins after physical contact with a partner who is seropositive for HSV.

102. The method of numbered paragraph 80, wherein the administering begins prior to physical contact with the HSV seropositive partner.

103. The method of numbered paragraph 80, comprising administering the composition to the HSV seropositive partner.

104. The method of numbered paragraph 80, wherein the HSV is HSV-1, HSV-2, varicella-zoster virus (VZV), Epstein-Barr virus (human herpes virus 4), cytomegalovirus (human herpes virus 5), roseolovirus (human herpes virus 6 and 7), or Karposi's sarcoma-associated herpes virus (human herpes virus 8).

105. The method of numbered paragraph 104, wherein the HSV is HSV-2.

106. The method of numbered paragraph 104, wherein the HSV is VZV.

107. The method of numbered paragraph 80, wherein the HSV infection is a neonatal infection.

108. The method of numbered paragraph 80, wherein the disease or infection associated with HSV infection is Alzheimer's disease.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A pharmaceutical composition for treatment of herpes simplex virus (HSV) infection, prophylaxis, or pre-exposure prophylaxis against HSV infection in a subject in need thereof comprising: a therapeutically effective amount of (a) valacyclovir or a salt or solvate thereof and (b) famciclovir or a salt or solvate thereof; and pharmaceutically acceptable excipient(s), diluent(s), carrier(s) and/or adjuvant(s).

2. The pharmaceutical composition of claim 1, comprising about 1 mg to about 8000 mg of valacyclovir or a salt or solvate thereof and about 1 mg to about 8000 mg famciclovir or a salt or solvate thereof, or comprising about 125 mg to about 2000 mg of valacyclovir or a salt or solvate thereof and about 60 mg to about 1000 mg famciclovir or a salt or solvate thereof.

3. The pharmaceutical composition of claim 1, formulated for oral administration, or comprising an oral tablet, oral capsule, or oral solution, or formulated for administration once daily or twice daily, or formulated in sustained-release form, or formulated in parenteral administration form.

4. The pharmaceutical composition of claim 1, additionally comprising a therapeutically effective amount of an additional antiviral agent or an HIV antiviral agent, or formulated for a female and additionally comprising a therapeutically effective amount of a contraceptive.

5. The pharmaceutical composition of claim 4, wherein the additional antiviral agent comprises a helicase-primase inhibitor, amenamevir, N-methancocarbathymidine (N-MCT), tenofovir, emtricitabine, lamivudine, interfereon, ribavirin, boceprevir, telaprevir, simeprevir, sofosbuvir, ledipasvir, tenofovir, ombitasvir, paritaprevir, penciclovir, pritelivir, brincidofovir, cidofovir, ganciclovir, valganciclovir, valomaciclovir, or ritonavir.

6. A method of pre-exposure prophylaxis against HSV infection in an HSV seronegative subject in need thereof, or a method of treating an HSV infection, or a method of suppressing an HSV infection, or a method of treatment or prophylactic treatment of a disease or condition associated with HSV infection, the method comprising administering to the subject daily a therapeutically effective amount of (a) valacyclovir or a salt or solvate thereof and (b) famciclovir or a salt or solvate thereof; and pharmaceutically acceptable excipient(s), diluent(s), carrier(s) and/or adjuvant(s).

7. The method of claim 6, wherein the therapeutically effective amount comprises 0.5 mg/kg body weight to about 1000 mg/kg body weight of (a) or about 5 mg/kg body weight to about 50 mg/kg body weight of (a) or about 25 mg/kg body weight to about 100 mg/kg body weight of (a) or about 50 mg/kg body weight to about 250 mg/kg body weight of (a) or about 100 mg/kg body weight to about 500 mg/kg body weight of (a) and 0.5 mg/kg body weight to about 1000 mg/kg body weight of (b) or about 5 mg/kg body weight to about 50 mg/kg body weight of (b) or about 25 mg/kg body weight to about 100 mg/kg body weight of (b) or about 50 mg/kg body weight to about 250 mg/kg body weight of (b) or about 100 mg/kg body weight to about 500 mg/kg body weight of (b).

8. The method of claim 7, wherein the therapeutically effective amount comprises (a) and (b) in a dose ratio in mg/kg of about 5:1, about 4:1, about 3:1, about 2:1, about 1:1, about 1:2, about 1:3, about 1:4, or about 1:5.

9. The method of claim 7, wherein the therapeutically effective amount comprises about 50 mg/kg body weight to about 150 mg/kg body weight of (a) and about 20 mg/kg body weight to about 50 mg/kg body weight of (b), or about 100 mg/kg body weight to about 150 mg/kg body weight of (a) and about 50 mg/kg body weight to about 100 mg/kg body weight of (b), or about 250 mg/kg body weight to about 1000 mg/kg body weight of (a) and about 150 mg/kg body weight to about 500 mg/kg body weight of (b).

10. The method of claim 7, wherein the HSV infection is comprises a neonatal infection, or wherein the disease or infection associated with HSV infection comprises Alzheimer's disease.

11. A method of pre-exposure prophylaxis against herpes simplex virus (HSV) infection in an HSV seronegative subject in need thereof, or a method of treating an HSV infection, or a method of suppressing an HSV infection, or a method of treatment or prophylactic treatment of a disease or condition associated with HSV infection, the method comprising administering to the subject daily a therapeutically effective amount of greater than 100 mg/kg body weight of an antiviral agent comprising acyclovir or a salt or solvate thereof, or valacyclovir or a salt or solvate thereof, or famciclovir or a salt or solvate thereof, or combinations thereof, whereby the risk of HSV infection in the subject is reduced.

12. The method of claim 11, wherein the amount of the antiviral agent is from greater than 100 mg/kg to about 1000 mg/kg body weight, or from greater than 100 mg/kg to about 700 mg/kg body weight, or from greater than 100 mg/kg to about 500 mg/kg body weight, or from greater than 100 mg/kg to about 250 mg/kg body weight, or from about 125 mg/kg to about 500 mg/kg body weight.

13. The method of claim 11, which comprises administering 0.5 mg/kg to about 1000 mg/kg body weight, or 0.5 mg/kg to about 700 mg/kg body weight, or 0.5 mg/kg to about 500 mg/kg body weight, or greater than about 100 mg/kg body weight of a second antiviral agent.

14. The method of claim 11, wherein the antiviral agent comprises greater than 100 mg/kg body weight of valacyclovir and greater than 100 mg/kg body weight of famciclovir, or comprises greater than 100 mg/kg to about 700 mg/kg body weight of valacyclovir and greater than 100 mg/kg to about 500 mg/kg body weight of famciclovir.

15. The method of claim 11, which comprises administering about 1 mg to about 8000 mg of valacyclovir or a salt or solvate thereof and about 1 mg to about 8000 mg of famciclovir or a salt or solvate thereof, or comprises administering about 125 mg to about 2000 mg of valacyclovir or a salt or solvate thereof and about 60 mg to about 1000 mg of famciclovir or a salt or solvate thereof.

16. The method of claim 11, which comprises oral or intravenous administration, or comprises once daily or twice daily administration.

17. The method of claim 11, wherein the administering begins after physical contact with a partner who is seropositive for HSV, or wherein the administering begins prior to physical contact with the HSV seropositive partner, and optionally comprises administering the composition to the HSV seropositive partner.

18. The method of claim 11, wherein the HSV is HSV-1, HSV-2, varicella-zoster virus (VZV), Epstein-Barr virus (human herpes virus 4), cytomegalovirus (human herpes virus 5), roseolovirus (human herpes virus 6 and 7), or Karposi's sarcoma-associated herpes virus (human herpes virus 8).

19. The method of claim 11, wherein the HSV infection comprises a neonatal infection, or wherein the disease or infection associated with HSV infection comprises Alzheimer's disease.

20. The pharmaceutical composition of claim 1, comprising about 125 mg to about 2000 mg of valacyclovir or a salt or solvate thereof and about 60 mg to about 1000 mg famciclovir or a salt or solvate thereof.

21. The pharmaceutical composition of claim 1, comprising about 1 mg to about 8000 mg of valacyclovir or a salt or solvate thereof and about 1 mg to about 8000 mg famciclovir or a salt or solvate thereof.

22. The method of claim 6, wherein the therapeutically effective amount comprises 0.5 mg/kg body weight to about 1000 mg/kg body weight of (a) and 0.5 mg/kg body weight to about 1000 mg/kg body weight of (b).

23. The method of claim 22, wherein the therapeutically effective amount comprises about 5 mg/kg body weight to about 50 mg/kg body weight of (a).

24. The method of claim 22, wherein the therapeutically effective amount comprises about 25 mg/kg body weight to about 100 mg/kg body weight of (a).

25. The method of claim 22, wherein the therapeutically effective amount comprises about 50 mg/kg body weight to about 250 mg/kg body weight of (a).

26. The method of claim 22, wherein the therapeutically effective amount comprises or about 100 mg/kg body weight to about 500 mg/kg body weight of (a).

27. The method of claim 22, wherein the therapeutically effective amount comprises about 5 mg/kg body weight to about 50 mg/kg body weight of (b).

28. The method of claim 22, wherein the therapeutically effective amount comprises or about 25 mg/kg body weight to about 100 mg/kg body weight of (b).

29. The method of claim 22, wherein the therapeutically effective amount comprises or about 50 mg/kg body weight to about 250 mg/kg body weight of (b).

30. The method of claim 22, wherein the therapeutically effective amount comprises about 100 mg/kg body weight to about 500 mg/kg body weight of (b).

31. The method of claim 7, wherein the therapeutically effective amount comprises about 50 mg/kg body weight to about 150 mg/kg body weight of (a) and about 20 mg/kg body weight to about 50 mg/kg body weight of (b).

32. The method of claim 7, wherein the therapeutically effective amount comprises about 100 mg/kg body weight to about 150 mg/kg body weight of (a) and about 50 mg/kg body weight to about 100 mg/kg body weight of (b).

33. The method of claim 7, wherein the therapeutically effective amount comprises about 250 mg/kg body weight to about 1000 mg/kg body weight of (a) and about 150 mg/kg body weight to about 500 mg/kg body weight of (b).

34. The method of claim 11, wherein the amount of the antiviral agent is from greater than 100 mg/kg to about 1000 mg/kg body weight.

35. The method of claim 11, wherein the amount of the antiviral agent is from greater than 100 mg/kg to about 700 mg/kg body weight.

36. The method of claim 11, wherein the amount of the antiviral agent is from greater than 100 mg/kg to about 500 mg/kg body weight.

37. The method of claim 11, wherein the amount of the antiviral agent is from greater than 100 mg/kg to about 250 mg/kg body weight.

38. The method of claim 11, wherein the amount of the antiviral agent is from about 125 mg/kg to about 500 mg/kg body weight.

39. The method of claim 11, which comprises administering 0.5 mg/kg to about 1000 mg/kg body weight of a second antiviral agent.

40. The method of claim 11, which comprises administering 0.5 mg/kg to about 700 mg/kg body weight of a second antiviral agent.

41. The method of claim 11, which comprises administering 0.5 mg/kg to about 500 mg/kg body weight of a second antiviral agent.

42. The method of claim 11, which comprises administering greater than about 100 mg/kg body weight of a second antiviral agent.

43. The method of claim 11, wherein the antiviral agent comprises greater than 100 mg/kg body weight of valacyclovir and greater than 100 mg/kg body weight of famciclovir.

44. The method of claim 11, which the antiviral agent comprises greater than 100 mg/kg to about 700 mg/kg body weight of valacyclovir and greater than 100 mg/kg to about 500 mg/kg body weight of famciclovir.

45. The method of claim 11, which comprises administering about 1 mg to about 8000 mg of valacyclovir or a salt or solvate thereof and about 1 mg to about 8000 mg of famciclovir or a salt or solvate thereof.

46. The method of claim 11, which comprises administering about 125 mg to about 2000 mg of valacyclovir or a salt or solvate thereof and about 60 mg to about 1000 mg of famciclovir or a salt or solvate thereof.

* * * * *